(12) United States Patent
McGurk et al.

(10) Patent No.: US 11,730,725 B2
(45) Date of Patent: Aug. 22, 2023

(54) NIRAPARIB FORMULATIONS

(71) Applicant: Tesaro, Inc., Waltham, MA (US)

(72) Inventors: Simon McGurk, Falmouth, ME (US); Padma Narayan, Brookline, MA (US); Aleksandar Rajlic, Brookline, MA (US)

(73) Assignee: Tesaro, Inc., Wilmington, DE (US)

( * ) Notice: Subject to any disclaimer, the term of this patent is extended or adjusted under 35 U.S.C. 154(b) by 100 days.

(21) Appl. No.: 16/650,948

(22) PCT Filed: Sep. 26, 2018

(86) PCT No.: PCT/US2018/052979
§ 371 (c)(1),
(2) Date: Mar. 26, 2020

(87) PCT Pub. No.: WO2019/067634
PCT Pub. Date: Apr. 4, 2019

(65) Prior Publication Data
US 2020/0289494 A1 Sep. 17, 2020

Related U.S. Application Data

(60) Provisional application No. 62/563,535, filed on Sep. 26, 2017.

(51) Int. Cl.
| | |
|---|---|
| *A61K 31/454* | (2006.01) |
| *A61K 9/16* | (2006.01) |
| *A61K 9/50* | (2006.01) |
| *A61K 47/02* | (2006.01) |
| *A61K 47/12* | (2006.01) |
| *A61K 47/26* | (2006.01) |
| *A61K 47/32* | (2006.01) |

(52) U.S. Cl.
CPC .......... *A61K 31/454* (2013.01); *A61K 9/1652* (2013.01); *A61K 9/5026* (2013.01); *A61K 47/02* (2013.01); *A61K 47/12* (2013.01); *A61K 47/26* (2013.01); *A61K 47/32* (2013.01)

(58) Field of Classification Search
CPC .. A61K 31/454; A61K 9/1652; A61K 9/5026; A61K 47/02; A61K 47/12; A61K 47/26; A61K 47/32; A61K 9/2095; A61K 9/2077; A61K 9/2009; A61K 9/2013; A61K 9/2018; A61K 9/2027; A61K 9/2054; A61P 35/00
See application file for complete search history.

(56) References Cited

U.S. PATENT DOCUMENTS

| | | | |
|---|---|---|---|
| 6,065,330 A | 5/2000 | Freeman et al. | |
| 8,071,623 B2 | 12/2011 | Jones et al. | |
| 8,436,185 B2 | 5/2013 | Foley et al. | |
| 11,091,459 B2 | 8/2021 | Wu et al. | |
| 2004/0186179 A1 | 9/2004 | Gimona et al. | |
| 2006/0167012 A1 | 7/2006 | Noble et al. | |
| 2008/0176946 A1 | 7/2008 | Ossovskaya et al. | |
| 2010/0278921 A1 | 11/2010 | Fischer et al. | |
| 2010/0286157 A1 | 11/2010 | Quiqley et al. | |
| 2010/0297194 A1 | 11/2010 | Catron et al. | |
| 2012/0214998 A1 | 8/2012 | Bierlmaier et al. | |
| 2015/0029916 A1 | 1/2015 | Vukadinovic et al. | |
| 2015/0110869 A1 | 4/2015 | Philip et al. | |
| 2015/0299219 A1 | 10/2015 | Xi et al. | |
| 2016/0045502 A1* | 2/2016 | Brown | A61K 31/513 544/309 |
| 2016/0051561 A1* | 2/2016 | Etter | A61K 9/2009 514/212.06 |
| 2016/0287594 A1 | 10/2016 | Gupta et al. | |
| 2016/0339124 A1* | 11/2016 | Mach | A61B 6/037 |
| 2017/0029428 A1 | 2/2017 | Blatter et al. | |
| 2018/0311224 A1 | 11/2018 | Hedley et al. | |
| 2019/0290629 A1 | 9/2019 | Gan et al. | |
| 2020/0016142 A1 | 1/2020 | McGurk et al. | |
| 2020/0017462 A1 | 1/2020 | Wu et al. | |
| 2021/0030735 A1 | 2/2021 | McGurk et al. | |
| 2021/0403448 A1 | 12/2021 | Wu et al. | |

FOREIGN PATENT DOCUMENTS

| | | |
|---|---|---|
| CN | 101415686 | 4/2009 |
| CN | 101578279 | 11/2009 |
| CN | 104363896 | 2/2015 |
| CN | 106496187 | 3/2017 |
| CN | 106831708 | 6/2017 |
| CN | 106854176 | 6/2017 |
| CN | 108530425 | 9/2018 |
| EP | 2007733 | 12/2008 |

(Continued)

OTHER PUBLICATIONS

Huang PARP-1 suppresses adiponectin, p. 98, Sep. 2009.*
Opadry II Feb., 2016 (Year: 2016).*
U.S. Appl. No. 62/489,415, filed Apr. 24, 2017, Stewart et al.
Blumenthal et al., "Pembrolizumab: first experience with recurrent primary central nervous system (CNS) tumors," J Neurooncol., 2016, 129(3):453-460.
Chornenkyy, "Poly-ADP-Ribose Polymerase as a Therapeutic Target in Pediatric Diffuse Intrinsic Pontine Glioma and Pediatric High-Grade Astrocytoma," Mol. Cancer Ther., 2015, 14(11):2560-2568.
Chung et al., "Process Development of C—N Cross-Coupling and Enantioselective Biocatalytic Reactions for the Asymmetric Synthesis of Niraparib," Org. Process Res. Dev., 2014, 18:215-27.

(Continued)

*Primary Examiner* — Matthew P Coughlin
*Assistant Examiner* — Thurman Wheeler
(74) *Attorney, Agent, or Firm* — Fish & Richardson P.C.

(57) ABSTRACT

The present invention relates to pharmaceutical tablet compositions comprising the compound niraparib as an active pharmaceutical ingredient, suitable for oral administration as well as to methods for their preparation. Also described herein are tablet compositions containing niraparib formed by the disclosed methods, and therapeutic uses of such tablet compositions for treating various disorders and conditions.

15 Claims, 9 Drawing Sheets

(56) References Cited

FOREIGN PATENT DOCUMENTS

| | | | | |
|---|---|---|---|---|
| JP | 2017-516784 | 6/2017 | | |
| WO | WO 2007/113596 | 10/2007 | | |
| WO | WO-2008043024 A2 * | 4/2008 | ........... | A61K 9/4866 |
| WO | WO 2008/084261 | 7/2008 | | |
| WO | WO 2009/087381 | 7/2009 | | |
| WO | WO 2014/088983 | 6/2014 | | |
| WO | WO 2014/088984 | 6/2014 | | |
| WO | WO 2014/179664 | 11/2014 | | |
| WO | WO 2015/164586 | 10/2015 | | |
| WO | WO 2015/184145 | 12/2015 | | |
| WO | WO 2016/028689 | 2/2016 | | |
| WO | WO 2016/094391 | 6/2016 | | |
| WO | WO 2016/126858 | 8/2016 | | |
| WO | WO 2016/141068 | 9/2016 | | |
| WO | WO 2016/161270 | 10/2016 | | |
| WO | WO 2017/023753 | 2/2017 | | |
| WO | WO 2017/125423 | 7/2017 | | |
| WO | WO 2017/210608 | 12/2017 | | |
| WO | WO 2018/005818 | 1/2018 | | |
| WO | WO 2018/085468 | 5/2018 | | |
| WO | WO 2018/085469 | 5/2018 | | |
| WO | WO 2018/108160 | 6/2018 | | |
| WO | WO 2018/122168 | 7/2018 | | |
| WO | WO 2018/129553 | 7/2018 | | |
| WO | WO 2018/129559 | 7/2018 | | |
| WO | WO 2018/183349 | 10/2018 | | |
| WO | WO 2018/183354 | 10/2018 | | |
| WO | WO 2018/200517 | 11/2018 | | |
| WO | WO 2018/201096 | 11/2018 | | |
| WO | WO 2018/208968 | 11/2018 | | |
| WO | WO 2018/213732 | 11/2018 | | |
| WO | WO 2019/067634 | 4/2019 | | |
| WO | WO 2019/067978 | 4/2019 | | |
| WO | WO 2019/071123 | 4/2019 | | |
| WO | WO 2019/133697 | 7/2019 | | |
| WO | WO 2019/152989 | 8/2019 | | |

OTHER PUBLICATIONS

Colgan et al., "The application of science and risk based concepts to drug substance stability strategies," J. Pharm. Innov., 2012, 7:205-213.

Emmanuel et al. "Small Volume Dissolution Testing as a Powerful Method during Pharmaceutical Development", Pharmaceutics, 2010, 2:351-63.

Globalnewswire.com [online], "TESARO Announces Availability of Zejula™ (Niraparib) for Patients With Recurrent Ovarian Cancer in the U.S.", Apr. 19, 2017, retrieved on Jun. 6, 2020, retrieved from URL <https://www.globenewswire.com/newsrelease/2017/04/19/962337/0/en/TESARO-Announces-Availability-of-Zejula-Niraparib-for-Patients-With-Recurrent-Ovarian-Cancer-in-the-U-S.html >, 7 pages.

Hughes, D. L., "Patent review of manufacturing routes to recently approved PARP inhibitors: olaparib, rucaparib, and niraparib." Organic Process Research & Development 21.9 (2017): 1227-1244.

Jones et al., "Discovery of 2-{4-[(3S)-piperidin-3-yl]phenyl}-2H-indazole-7-carboxamide (MK-4827): a novel oral poly(ADP-ribose)polymerase (PARP) inhibitor efficacious in BRCA-1 and -2 mutant tumors ," Journal Medicinal Chemistry, 2009, 52:7170-7185.

Kim et al., "PD-L1 expression on immune cells, but not on tumor cells, is a favorable prognostic factor for head and neck cancer patients," Sci Rep., 2016, 6:36956.

Konstantinopoulus, "Dose-finding combination study of niraparib and pembrolizumab in patients (pts) with metastatic triple-negative breast cancer (TNBC) or recurrent platinum resistant epithelial ovarian Cancer (OC)," Annals of Oncology, Sep. 1, 2017, 28(Suppl 5):1143PD.

PCT International Preliminary Report on Patentability for International Application No. PCT/US2018/024597, dated Oct. 1, 2019, 11 pages.

PCT International Preliminary Report on Patentability in International Application No. PCT/US2018/024603, dated Jul. 20, 2018, 10 pages.

PCT International Preliminary Report on Patentability in International Application No. PCT/US2019/016648, dated Aug. 11, 2020, 8 pages.

PCT International Search Report and Written Opinion in International Application No. PCT/US2019/016648, dated Apr. 5, 2019, 12 pages.

PCT International Search Report and Written Opinion in International Application No. PCT/US2018/024603, dated Jul. 20, 2018, 13 pages.

PCT International Search Report and Written Opinion in International Application No. PCT/US2018/024597, dated Jul. 27, 2018, 14 pages.

Rom-Jurek et al., "Regulation of Programmed Death Ligand 1 (PD-L1) Expression in Breast Cancer Cell Lines In Vitro and in Immunodeficient and Humanized Tumor Mice," Int J Mol Sci., 2018, 19:563.

Shukuya et al., "Predictive Markers for the Efficacy of Anti-PD-1/PD-L1 Antibodies in Lung Cancer," Journal of Thoracic Oncology, 2016, 11(7):976-988.

TESARO: "A phase III, randomized, open label, multicenter, controlled trial of niraparib versus physician's choice in previously-treated, HER2 negative, germline BRCA mutation-positive breast cancer patients", ClinicalTrials.gov [online], NCT01905592 Study Protocol, Jan. 2017, <https://clinicaltrials.gov/ProvidedDocs/92/NCT01905592/Prot_001.pdf>.

TESARO: "Phase 1/2 Clinical Study of Niraparib in Combination with Pemobrolizumab in Patients with Advanced or Metastatic Triple-Negative Breast Cancer and in Patients with Recurrent Ovarian Cancer" Clinical Study Protocol 3000-PN162-01-001 Amendment 2, Mar. 1, 2017, [online] <https://clinicaltrials.gov/ProvidedDocs/89/NCT02657889/Prot_000.pdf>, [retrieved online Sep. 1, 2020].

Test 711 ""Dissolution"", the United States Pharmacopoeia. 37th revision: United States Pharmacopoeia, Convention, Inc., Rockville, Md., 2014 (""USP 711""), 10 pages.

Vormoor et al., ,"Poly(ADP-ribose) polymerase inhibitors in Ewing sarcoma," Curr Opin Oncol., Jul. 1, 2014, 26(4):428-433.

Wallace et al., "Development of a Fit-for-Purpose Large-Scale Synthesis of an Oral PARP Inhibitor," Org. Process Res. Dev., 2011, 15:831-840.

Wilcoxen, "Abstract A258: The PARP inhibitor niraparib demonstrates synergy with chemotherapy in treatment of patient derived Ewing's sarcoma tumor Graft models," Molecular Cancer Therapeutics, 2013, 12(11):A258.

Zejula Patient Information approved by the U.S. Food and Drug Administration, Mar. 2017.

[No Author Listed], "Tablet Friability," The United States Pharmacopea, May 1, 2009, 1:6 pages.

Antonis et al., "The Application of Science and Risk Based Concepts to Drug Substance Stability Strategies," J. Pharm. Innov., 2012, 7:205-213.

Colgan et al., "Opportunities for Lean Stability Strategies," J. Pharm. Innov., 2014, 9:259-271.

European Pharmacopoeia, Supplement 6.6; Friability of Uncoated Tablets, Jun. 2009, 2.9.7., 1 page.

International Preliminary Report on Patentability in International Appln. No. PCT/US2018/052979, dated Mar. 31, 2020, 8 pages.

International Search Report and Written Opinion in International Appln. No. PCT/US2018/052979, dated Jan. 2, 2019, 10 pages.

Waterman et al.. "Improved protocol and data analysis for accelerated shelf-life estimation of solid dosage forms," Pharm Res., 2007, 24(4):780-90.

www.std.pmda.go [online], "The Ministry of Health, Labour and Welfare Ministerial Notification No. 285," Nov. 5, 2008, retrieved on Jul. 7, 2020, retrieved from URL<http://www.assaabloy.com/en/com/Press- News/News/2011/NFC-enabled-mobile-access-in-a-physicalaccess-control-world/, 16 pages.

Cerrato et al., "Use of poly ADP-ribose polymerase [PARP] inhibitors in cancer cells bearing DDR defects: the rationale for their inclusion in the clinic", Journal of Experimental & Clinical Cancer Research, Nov. 2016, 35(1): 179-191.

(56) References Cited

OTHER PUBLICATIONS

Frolova et al., "PARP inhibitors in the treatment of metastatic breast cancer patients with germline BRCA1/2 mutations. Experience of treatment with talazoparib in clinical practice," Meditsinskiy Sovet, Jul. 2020, 9:57-61 (with English Abstract).
Hao et al., "A new oral polybosphate adenosine ribose polymerase inhibitor-niraparib", Clinical Medication Journal, 2017, 15(6): 13-17 (with English abstract).
Kojima, "Targeting for Efficiency in Selecting Crystalline Form in Development of Medicine", Pharmacy, Sep. 2008, 68(5): 344-349, 22 pages (with machine translation).
Maruzen, "Pharmaceutical Crystallization Method and Diastereomer salt formation method for optical resolution Crystallization in place—Methods and applications—", Handbook of Preparation of Organic Compound Crystals—Principle and Know-How—, Jul. 2008, p. 57-84, 37 pages (with machine translation).
Ministry of Health, Labor, and Welfare, Commissioner of Pharmaceutical Safety Evaluation Division, "Residual Solvent Guidelines for Pharmaceutical Products", Pharmaceutical Evaluation, No. 307, 1998, pp. 1-11, 24 pages (with machine translation).
Ruhua, "Industrial Pharmacy", China Medical Science and Technology Press, Sep. 1998, pp. 334-335 (English translation only).
Takada, "Active Pharmaceutical Ingredient Form Screening and Selection in Drug Discovery Stage", Pharm Stage, Jan. 2007, 6(10):20-25, 22 pages (with machine translation).
wikipedia.org [online], "Carr index," Aug. 17, 2021, retrieved on Mar. 28, 2022, retrieved from URL <https://en.wikipedia.org/w/index.php?title=Carr_index&oldid=1039190201>, 2 pages.
Immunotherapy of Cancer, 2017, 28(Supplement 5), 420, 1185P.
Immunotherapy of Cancer, 2017, 28(Supplement 5), 406-407, 1143PD.
Mariappan et al., "Emerging treatment options for ovarian cancer focus on rucaparib," International Journal of Women's Health, 2017, 9:913-924.
Ohmoto et al., "Current status of poly(ADP-ribose) polymerase inhibitors and future directions," Onco Targets and Therapy, 2017, (10):5195-5208.
Technical News, Technical Journal of Okinawa Industrial Technology Center, 2012, 15(2):6, 4 pages (partial translation).

* cited by examiner

| STORAGE CONDITION: | 25°C/60%RH | | | | | | | | | |
|---|---|---|---|---|---|---|---|---|---|---|
| | | STORAGE TIME (MONTHS) | | | | | | | | |
| TEST/PROCEDURE | ACCEPTANCE CRITERIA | INITIAL | 1 | 3 | 6 | 9 | 12 | 18 | 24 | 36 |
| ASSAY | 90-110% LC | CONFORMS | CONFORMS | CONFORMS | CONFORMS | " | " | " | " | " |
| DEGRADATION PRODUCTS: TOTAL | NMT 1.0% w/w | <0.2% | N.C. | N.C. | N.C. | " | " | " | " | " |
| WATER CONTENT | REPORT RESULTS | <10% | N.C. | N.C. | N.C. | " | " | " | " | " |

N.C. = NO CHANGE

FIG. 6

| STORAGE CONDITION: | 40°C/75%RH | STORAGE TIME (MONTHS) | | | |
|---|---|---|---|---|---|
| TEST/PROCEDURE | ACCEPTANCE CRITERIA | INITIAL | 1 | 3 | 6 |
| ASSAY | 90-110% LC | CONFORMS | CONFORMS | CONFORMS | CONFORMS |
| DEGRADATION PRODUCTS: TOTAL | NMT 1.0% w/w | <0.2% | n.c. | n.c. | n.c. |
| WATER CONTENT | REPORT RESULTS | <10% | n.c. | n.c. | n.c. |

N.C. = NO CHANGE

| STORAGE CONDITION: | 25°C/60%RH | | | | | | | | | |
|---|---|---|---|---|---|---|---|---|---|---|
| | | | TIME IN MONTHS | | | | | | | |
| TEST/PROCEDURE | ACCEPTANCE CRITERIA | INITIAL | 1 | 3 | 6 | 9 | 12 | 18 | 24 | 36 |
| ASSAY | 90-110% LC | CONFORMS | CONFORMS | CONFORMS | CONFORMS | " | " | " | " | " |
| DEGRADATION PRODUCTS: TOTAL | NMT 1.0% w/w | <0.2% | n.c. | n.c. | n.c. | " | " | " | " | " |
| WATER CONTENT | REPORT RESULTS | <10% | n.c. | n.c. | n.c. | " | " | " | " | " |

N.C. = NO CHANGE

| STORAGE CONDITION: | 40°C/75%RH | | | | |
|---|---|---|---|---|---|
| | | STORAGE TIME (MONTHS) | | | |
| TEST/PROCEDURE | ACCEPTANCE CRITERIA | INITIAL | 1 | 3 | 6 |
| ASSAY | 90-110% LC | CONFORMS | CONFORMS | CONFORMS | CONFORMS |
| DEGRADATION PRODUCTS: TOTAL | NMT 1.0% w/w | <0.2% | n.c. | n.c. | n.c. |
| WATER CONTENT | REPORT RESULTS | <10% | n.c. | n.c. | n.c. |

N.C. = NO CHANGE

FIG. 9

NIRAPARIB FORMULATIONS

CROSS-REFERENCE TO RELATED APPLICATIONS

The present application is a 35 U.S.C. § 371 National Stage Application of International Application No. PCT/US2018/052979, filed on Sep. 26, 2018, which claims benefit of U.S. Provisional Application No. 62/563,535, filed Sep. 26, 2017, each of which is hereby incorporated by reference in its entirety.

SUMMARY OF THE INVENTION

Niraparib is an orally active and potent poly (ADP-ribose) polymerase, or PARP, inhibitor. Niraparib and pharmaceutically acceptable salts thereof, are disclosed in International Publication No. WO2007/113596 and European Patent No. EP2007733B1; International Publication No. WO2008/084261 and U.S. Pat. No. 8,071,623; and International Publication No. WO2009/087381 and U.S. Pat. No. 8,436, 185. Methods of making niraparib and pharmaceutically acceptable salts thereof are disclosed in International Publication Nos. WO2014/088983 and WO2014/088984. Methods to treat cancer with niraparib and pharmaceutically acceptable salts thereof are disclosed in U.S. Provisional Patent Application Nos. 62/356,461 and 62/402,427, as well as in International Publication No. WO 2018/005818. The contents of each of the foregoing references are incorporated herein by reference in their entirety.

PARP is a family of proteins involved in many functions in a cell, including DNA repair, gene expression, cell cycle control, intracellular trafficking and energy metabolism. PARP proteins play key roles in single strand break repair through the base excision repair pathway. PARP inhibitors have shown activity as a monotherapy against tumors with existing DNA repair defects, such as BRCA1 and BRCA2, and as a combination therapy when administered together with anti-cancer agents that induce DNA damage.

Despite several advances in treatment of ovarian cancer, most patients eventually relapse, and subsequent responses to additional treatment are often limited in duration. Women with germline BRCA1 or BRCA2 mutations have an increased risk for developing high grade serous ovarian cancer (HGSOC), and their tumors appear to be particularly sensitive to treatment with a PARP inhibitor. In addition, published scientific literature indicates that patients with platinum sensitive HGSOC who do not have germline BRCA1 or BRCA2 mutations may also experience clinical benefit from treatment with a PARP inhibitor.

It is estimated that 5% to 10% of women who are diagnosed with breast cancer, or more than 15,000 women each year, carry a germline mutation in either their BRCA1 or BRCA2 genes. The development of cancer in these women involves the dysfunction of a key DNA repair pathway known as homologous recombination. While cancer cells can maintain viability despite disruption of the homologous recombination pathway, they become particularly vulnerable to chemotherapy if an alternative DNA repair pathway is disrupted. This is known as synthetic lethality—a situation where the individual loss of either repair pathway is compatible with cell viability; but the simultaneous loss of both pathways results in cancer cell deaths. Since PARP inhibitors block DNA repair, in the context of cancer cells with the BRCA mutation, PARP inhibition results in synthetic lethality. For this reason, patients with germline mutations in a BRCA gene show marked clinical benefit that follows treatment with a PARP inhibitor.

It has surprisingly been found that the solid dosage forms according to the present invention have desirable properties that demonstrate excellent storage stability, potency, and disintegration profiles. Thus, such dosage forms can be beneficial for use in the treatment of subjects having diseases such as cancer. In some embodiments, the solid dosage forms disclosed herein allow for tablet manufacturability, which includes reducing the stickiness of the active pharmaceutical ingredient during manufacturing process.

Accordingly, in one aspect, the invention features a composition comprising an effective amount of niraparib to inhibit polyadenosine diphosphate ribose polymerase (PARP) when administered to a subject in need thereof, wherein the composition is a pharmaceutical composition formulated as a tablet.

Provided in one aspect is a composition (e.g., a pharmaceutical composition formulated as a tablet) comprising:
  an effective amount of niraparib to inhibit polyadenosine diphosphate ribose polymerase (PARP) when administered to a subject in need thereof;
    wherein the tablet is characterized by at least one of the following features:
    (a) the tablet comprises less than about 0.2% by weight of any single niraparib degradation product;
    (b) the tablet comprises less than about 0.2% by weight of any single niraparib degradation product after storage for about 1 month at about 40° C. and about 75% relative humidity (RH); and
    (c) the tablet comprises less than about 0.2% by weight of any single niraparib degradation product after storage for about 2 months at about 40° C. and about 75% relative humidity (RH).

In embodiments, the tablet comprises less than about 0.2% by weight of any single niraparib degradation product. In embodiments, the tablet comprises less than about 0.2% by weight of any single niraparib degradation product after storage for about 1 month at about 40° C. and about 75% relative humidity (RH). In embodiments, the tablet comprises less than about 0.2% by weight of any single niraparib degradation product after storage for about 2 months at about 40° C. and about 75% relative humidity (RH).

In some embodiments, the tablet comprises less than about 0.2%, 0.1%, 0.09%, 0.08%, 0.07%, 0.06%, 0.05%, 0.04%, 0.03%, 0.02%, 0.01%, 0.005%, or 0.001% by weight of any single niraparib degradation product. In some embodiments, the tablet comprises less than about 0.2%, 0.1%, 0.09%, 0.08%, 0.07%, 0.06%, 0.05%, 0.04%, 0.03%, 0.02%, 0.01%, 0.005%, or 0.001% by weight of any single niraparib degradation product after storage for about 1 month at about 40° C. and about 75% relative humidity (RH). In some embodiments, the tablet comprises less than about 0.2%, 0.1%, 0.09%, 0.08%, 0.07%, 0.06%, 0.05%, 0.04%, 0.03%, 0.02%, 0.01%, 0.005%, or 0.001% by weight of any single niraparib degradation product after storage for about 2 months at about 40° C. and about 75% relative humidity (RH).

Impurities or degradation products resulting from a chemical change in the drug substance brought about during manufacture and/or storage of the drug product by the effect of light, temperature, moisture or by reaction with an excipient are specifically quantitatively determined using techniques and equipment available and known to those having ordinary skill in the art. Exemplary methods include chromatographic methods such as high performance liquid chromatography (HPLC) (e.g., chiral chromatography, ion-exchange chromatography, ion-pair/affinity chromatography, reversed phase chromatography, and size-exclusion chromatography); gas chromatography (GC); and thin-layer chromatography (TLC). For example, a suitable method can be a validated, stability indicating gradient reverse-phased HPLC method with UV detection and using an external standard method. Mass spectrometry (MS) can be used alone or in tandem with chromatographic methods (e.g., HPLC-MS or GC-MS). Spectrophotometry (e.g., UV-Vis spectrophotometry) can also be used. The impurity levels in the drug product are reported and controlled per the requirements of International Conference on Harmonization (ICH) Q3B guidelines.

Provided in another aspect is a composition (e.g., a pharmaceutical composition formulated as a tablet) comprising:
an effective amount of niraparib to inhibit polyadenosine diphosphate ribose polymerase (PARP) when administered to a subject in need thereof;
wherein the tablet has at least one of the following:
(a) a weight of at least about 200, 300, 400, 500, 600, 700, 800, 900, 1000, 1100, or 1200 mg;
(b) a thickness of at least about 4.0 mm; and
(c) a friability of less than about 2%;
wherein the effective amount of niraparib is from about 50 mg to about 350 mg based on the niraparib free base.

In embodiments, the tablet has a weight of at least about 200, 300, 400, 500, 600, 700, 800, 900, 1000, 1100, or 1200 mg. In embodiments, the tablet has a weight of at least about 200, 500, or 800 mg.

In embodiments, the tablet has a thickness of at least about 4.0 mm.

In embodiments, the tablet has a friability of less than about 2%.

In some embodiments, the effective amount of niraparib is from about 75 mg to about 125 mg based on the niraparib free base. In some embodiments, the effective amount of niraparib is about 50 mg, about 100 mg, or about 150 mg based on the niraparib free base. In some embodiments, the effective amount of niraparib is about 100 mg based on the niraparib free base. In some embodiments, the niraparib comprises niraparib free base or a pharmaceutically acceptable salt thereof. In some embodiments, the pharmaceutically acceptable salt of niraparib is niraparib tosylate. In some embodiments, the tablet has a net weight of at least about 200 mg, at least about 210 mg, at least about about 220 mg, at least about 230 mg, at least about 240 mg, at least about 250 mg, at least about 260 mg, at least about 270 mg, at least about 280 mg, at least about 290 mg, about 300 mg, at least about 310 mg, at least about 320 mg, at least about 330 mg, at least about 340 mg, at least about 350 mg, at least about 360 mg, at least about 370 mg, at least about 380 mg, at least about 390 mg, at least about 400 mg, at least about 410 mg, at least about 420 mg, at least about 430 mg, at least about 440 mg, at least about 450 mg, at least about 460 mg, at least about 470 mg, at least about 480 mg, at least about 490 mg, or at least about 500 mg. In some embodiments, the tablet has a net weight of at least about 300 mg. In embodiments, the tablet has a net weight of about 300 mg to about 450 mg. In embodiments, the tablet has a net weight of about 300 mg to about 350 mg, about 350 mg to about 400 mg, or about 400 mg to about 450 mg. In embodiments, the tablet has a net weight of about 300 mg to about 350 mg. In embodiments, the tablet has a net weight of about 350 mg to about 400 mg. In embodiments, the tablet has a net weight of about 400 mg to about 450 mg.

In some embodiments, the effective amount of niraparib is from about 175 mg to about 225 mg based on the niraparib free base. In some embodiments, the effective amount of niraparib is about 150 mg, about 200 mg, or about 250 mg based on the niraparib free base. In some embodiments, the effective amount of niraparib is about 200 mg based on the niraparib free base. In some embodiments, the niraparib comprises niraparib free base or a pharmaceutically acceptable salt thereof. In some embodiments, the pharmaceutically acceptable salt of niraparib is niraparib tosylate. In some embodiments, the tablet has a net weight of at least about 500 mg, at least about 510 mg, at least about 520 mg, at least about 530 mg, at least about 540 mg, at least about 550 mg, at least about 560 mg, at least about 570 mg, at least about 580 mg, at least about 590 mg, at least about 600 mg, at least about 610 mg, at least about 620 mg, at least about 630 mg, at least about 640 mg, at least about 650 mg, at least about 660 mg, at least about 670 mg, at least about 680 mg, at least about 690 mg, at least about 700 mg, at least about 710 mg, at least about 720 mg, at least about 730 mg, at least about 740 mg, at least about 750 mg, at least about 760 mg, at least about 770 mg, at least about 780 mg, at least about 790 mg, or at least about 800 mg. In some embodiments, the tablet has a net weight of at least about 600 mg. In embodiments, the tablet has a net weight of about 600 mg to about 750 mg. In embodiments, the tablet has a net weight of about 600 mg to about 650 mg, about 650 mg to about 700 mg, or about 700 mg to about 750 mg. In embodiments, the tablet has a net weight of about 600 mg to about 650 mg. In embodiments, the tablet has a net weight of about 650 mg to about 700 mg. In embodiments, the tablet has a net weight of about 700 mg to about 750 mg.

In some embodiments, the effective amount of niraparib is from about 275 mg to about 325 mg based on the niraparib free base. In some embodiments, the effective amount of niraparib is about 250 mg, about 300 mg, or about 350 mg based on the niraparib free base. In some embodiments, the effective amount of niraparib is about 300 mg based on the niraparib free base. In some embodiments, the niraparib comprises niraparib free base or a pharmaceutically acceptable salt thereof. In some embodiments, the pharmaceutically acceptable salt of niraparib is niraparib tosylate. In some embodiments, the tablet has a net weight of at least about 800 mg, at least about 810 mg, at least about 820 mg, at least about 830 mg, at least about 840 mg, at least about 850 mg, at least about 860 mg, at least about 870 mg, at least about 880 mg, at least about 890 mg, at least about 900 mg, at least about 910 mg, at least about 920 mg, at least about 930 mg, at least about 940 mg, at least about 950 mg, at least about 960 mg, at least about 970 mg, at least about 980 mg, at least about 990 mg, at least about 1000 mg, at least about 1010 mg, at least about 1020 mg, at least about 1030 mg, at least about 1040 mg, at least about 1050 mg, at least about 1060 mg, at least about 1070 mg, at least about 1080 mg, at least about 1090 mg, at least about 1100 mg, at least about 1110 mg, at least about 1120 mg, at least about 1130 mg, at least about 1140 mg, at least about 1150 mg, at least about 1160 mg, at least about 1170 mg, at least about 1180 mg, at least about 1190 mg, or at least about 1200 mg. In some embodiments, the tablet has a net weight of at least about 1000 mg. In embodiments, the tablet has a net weight of about 1000 mg to about 1150 mg. In embodiments, the tablet has a net weight of about 1000 mg to about 1050 mg, of about 1050 mg to about 1100 mg, or about 1100 mg to about 1150 mg. In embodiments, the tablet has a net weight of about 1000 mg to about 1050 mg. In embodiments, the tablet has a net weight of about 1050 mg to about 1100 mg. In embodiments, the tablet has a net weight of about 1100 mg to about 1150 mg.

In some embodiments, the tablet has a thickness of at least 4.0 mm, at least 4.1 mm, at least 4.2 mm, at least 4.3 mm, at least 4.4, at least 4.5 mm, at least 4.6 mm, at least 4.7 mm, at least 4.8 mm, at least 4.9 mm, at least 5.0 mm, at least 5.1 mm, at least 5.2 mm, at least 5.3 mm, at least 5.4 mm, at least 5.5 mm, at least 5.6 mm, at least 5.7 mm, at least 5.8 mm, at least 5.9 mm, at least 6.0 mm, at least 6.1 mm, at least 6.2 mm, at least 6.3 mm, at least 6.4 mm, at least 6.5 mm, at least 6.6 mm, at least 6.7 mm, at least 6.8, at least 6.9 mm, at least 7.0 mm, at least 7.1 mm, at least 7.2 mm, at least 7.3 mm, at least 7.4 mm, at least 7.5 mm, at least 7.6 mm, at least 7.7 mm, at least 7.8 mm, at least 7.9 mm, at least 8.0 mm, at least 8.5 mm, at least 9.0 mm, at least 9.5 mm, or at least 10 mm.

In some embodiments, the tablet has a friability of less than 2%, less than 1.9%, less than 1.8%, less than 1.7%, less than 1.6%, less than 1.5%, less than 1.4%, less than 1.3%, less than 1.2%, less than 1.1%, less than 1.0%, less than 0.9%, less than 0.8%, less than 0.7%, less than 0.6%, less than 0.5%, less than 0.4%, less than 0.3%, less than 0.2%, or less than 0.1%.

In some embodiments, the niraparib comprises niraparib free base or a pharmaceutically acceptable salt thereof. In some embodiments, the pharmaceutically acceptable salt of niraparib is niraparib tosylate.

Provided in another aspect is a composition (e.g., a pharmaceutical composition formulated as a tablet) comprising
(a) an effective amount of niraparib to inhibit polyadenosine diphosphate ribose polymerase (PARP) when administered to a subject in need thereof; and
(b) silicon dioxide;
wherein the effective amount of niraparib is from about 50 mg to about 350 mg based on the niraparib free base.

In some embodiments, the effective amount of niraparib is from about 75 mg to about 125 mg based on the niraparib free base. In some embodiments, the effective amount of niraparib is about 50 mg, about 100 mg, or about 150 mg based on the niraparib free base. In some embodiments, the effective amount of niraparib is about 100 mg based on the niraparib free base. In some embodiments, the effective amount of niraparib is from about 175 mg to about 225 mg based on the niraparib free base. In some embodiments, the effective amount of niraparib is about 150 mg, about 200 mg, or about 250 mg based on the niraparib free base. In some embodiments, the effective amount of niraparib is about 200 mg based on the niraparib free base. In some embodiments, the effective amount of niraparib is from about 275 mg to about 325 mg based on the niraparib free base. In some embodiments, the effective amount of niraparib is about 250 mg, about 300 mg, or about 350 mg based on the niraparib free base. In some embodiments, the effective amount of niraparib is about 300 mg based on the niraparib free base. In some embodiments, the niraparib comprises niraparib free base or a pharmaceutically acceptable salt thereof. In some embodiments, the pharmaceutically acceptable salt of niraparib is niraparib tosylate.

In another aspect, the invention features a composition (e.g., a pharmaceutical composition formulated as a tablet comprising niraparib in an amount of about 50 mg to about 350 mg based on the niraparib free base, wherein the tablet comprises an intragranular phase and an extragranular phase, and wherein:

(a) at least one component of the intragranular phase is a diluent, a binder, a disintegrant, a glidant, or a lubricant; and/or
(b) at least one component of the extragranular phase is a disintegrant, a glidant, or a lubricant.

Provided in another aspect is a composition (e.g., a pharmaceutical composition formulated as a tablet) comprising:
an effective amount of niraparib to inhibit polyadenosine diphosphate ribose polymerase (PARP) when administered to a subject in need thereof;
wherein the tablet further comprises an intragranular phase and an extragranular phase; and
the tablet has at least one of the following:
(a) the amount of components used to form the intragranular phase is about 50% to about 98% by weight of the tablet composition; and
(b) the amount of components used to form the extragranular phase is about 2% to about 50% by weight of the tablet composition.

In some embodiments, the amount of components used to form the intragranular phase is about 50% to about 98% by weight of the tablet composition. In some embodiments, the amount of components used to form the intragranular phase is about 85% to about 98% by weight of the tablet composition. In some embodiments, the amount of components used to form the intragranular phase is about 90% to about 98% by weight of the tablet composition (e.g., the amount of components used to form the intragranular phase is at least about 90%, about 91%, about 92%, about 93%, about 94%, about 95%, about 96%, or about 97% or the amount of components used to form the intragranular phase is about 90%, about 91%, about 92%, about 93%, about 94%, about 95%, about 96%, or about 97%). In some embodiments, the amount of components used to form the intragranular phase is about 92.5% to about 97.5% by weight of the tablet composition. In some embodiments, the amount of components used to form the intragranular phase is about 95% by weight of the tablet composition.

In some embodiments, the amount of components used to form the extragranular phase is about 2% to about 50% by weight of the tablet composition. In some embodiments, the amount of components used to form the extragranular phase is about 2% to about 15% by weight of the tablet composition. In some embodiments, the amount of components used to form the extragranular phase is about 2% to about 10% by weight of the tablet composition (e.g., the amount of components used to form the extragranular phase is no more than about 9%, about 8%, about 7%, about 6%, about 5%, about 4%, or about 3% or the amount of components used to form the extragranular phase is about 2%, about 3%, about 4%, or about 5%). In some embodiments, the amount of components used to form the extragranular phase is about 2.5% to about 7.5% by weight of the tablet composition. In some embodiments, the amount of components used to form the extragranular phase is about 5% by weight of the tablet composition.

In some embodiments, any one of the compositions described herein comprises a first diluent. In some embodiments, any one of the compositions described herein comprises a second diluent. In some embodiments, any one of the compositions described herein comprises a lubricant. In some embodiments, any one of the compositions described herein comprises a binder.

In another aspect is provided a composition (e.g., a pharmaceutical composition formulated as a tablet) comprising niraparib tosylate monohydrate in an amount of about 100 mg to about 550 mg, wherein the composition is a pharmaceutical composition formulated as a tablet comprising an intragranular phase and an extragranular phase. In embodiments, the composition comprises niraparib tosylate monohydrate in an amount that is about 40-50% by weight of the tablet composition.

In embodiments, the intragranular phase comprises a diluent (e.g., a first diluent) in an amount that is about 7.5-15%, about 8-14%, or about 9-11% by weight of the tablet composition. In embodiments, the intragranular phase comprises a second diluent in an amount that is about 25-40%, about 30-40%, or about 30-35% by weight of the tablet composition. In embodiments, the intragranular phase comprises a binder in an amount that is about 1-3% by weight of the tablet composition. In embodiments, the intragranular phase comprises a disintegrant in an amount that is about 0.1-2% or about 0.5%-1.5% by weight of the tablet composition. In embodiments, the intragranular phase comprises a glidant, adsorbant, or absorbant in an amount that is about 1-5% or about 2-4% by weight of the tablet composition. In embodiments, the intragranular phase comprises a lubricant in an amount that is about 0.1-2% by weight of the tablet composition. In embodiments, the extragranular phase comprises a disintegrant in an amount that is about 0.1-2% by weight of the tablet composition. In embodiments, the extragranular phase comprises a glidant or adsorbant or absorbant in an amount that is about 0.1-2% by weight of the tablet composition. In embodiments, the extragranular phase comprises a lubricant in an amount that is about 0.1-2% by weight of the tablet composition.

Provided herein in another aspect is a composition (e.g., a pharmaceutical composition formulated as a tablet) comprising the following components on a weight percentage basis:
(a) in an intragranular portion:
  (i) about 40-50% niraparib tosylate monohydrate;
  (ii) about 8-14% of a first diluent;
  (iii) about 30-40% of a second diluent;
  (iv) about 1-3% of a binder;
  (v) about 0.1-2% of a disintegrant;
  (vi) about 2-4% of a glidant or adsorbant or absorbant; and
  (vii) about 0.1-2% of a lubricant;
(b) in an extragranular portion:
  (i) about 0.1-2% of a disintegrant;
  (ii) about 0.1-2% of a glidant or adsorbant or absorbant; and
  (iii) about 0.1-2% of a lubricant.

Provided herein in another aspect is a composition comprising a tablet comprising the following components on a weight percentage basis:
(a) in an intragranular portion:
  (i) 40-50% niraparib tosylate monohydrate;
  (ii) 9-11% of a first diluent;
  (iii) 30-40% of a second diluent;
  (iv) 1-3% of a binder;
  (v) 0.1-2% of a disintegrant;
  (vi) 2-4% of a glidant or adsorbant or absorbant; and
  (vii) 0.1-2% of a lubricant;
(b) in an extragranular portion:
  (i) 0.1-2% of a disintegrant;
  (ii) 0.1-2% of a glidant or adsorbant or absorbant; and
  (iii) 0.1-2% of a lubricant.

Provided herein in another aspect is a composition comprising a tablet comprising the following components on a weight percentage basis:
(a) in an intragranular portion:
  (i) about 40-50% niraparib tosylate monohydrate;
  (ii) about 9-40% of a diluent;
  (iii) about 1-3% of a binder;
  (iv) about 0.1-2% of a disintegrant;
  (v) about 2-4% of a glidant or adsorbant or absorbant; and
  (vi) about 0.1-2% of a lubricant;
(b) in an extragranular portion:
  (i) about 0.1-2% of a disintegrant;
  (ii) about 0.1-2% of a glidant or adsorbant or absorbant; and
  (iii) about 0.1-2% of a lubricant.

In some embodiments, the lubricant is magnesium stearate.

In some embodiments, the disintegrant is crospovidone.

In some embodiments, the glidant is silicon dioxide, optionally wherein the glidant is intermediate meso-porous silica, further optionally wherein the intermediate meso-porous silica comprises syloid FP-244.

Provided in another aspect is a composition (e.g., a pharmaceutical composition formulated as a tablet) comprising
(a) an effective amount of niraparib to inhibit polyadenosine diphosphate ribose polymerase (PARP) when administered to a subject in need thereof;
(b) a first diluent selected from lactose monohydrate, lactose anhydrous, mannitol, and calcium phosphate dibasic;
(c) magnesium stearate;
(d) a second diluent selected from microcrystalline cellulose, starch, polyethylene oxide, and hydroxypropyl methylcellulose (HPMC); and
(e) a binder selected from povidone (PVP), hydroxypropyl cellulose (HPC), and hydroxypropyl methylcellulose (HPMC).

In some embodiments, the diluent is lactose, mannitol, calcium phosphate dibasic, microcrystalline cellulose, starch, polyethylene oxide, or hydroxypropyl methylcellulose (HPMC). In some embodiments, the lactose is anhydrous, monohydrate, crystalline, or spray-dried. In some embodiments, the mannitol is spray dried or crystalline. In some embodiments, the first diluent is lactose monohydrate. In some embodiments, the lactose monohydrate is engineered (e.g., spray dried) or non-engineered (e.g., powder). In some embodiments, the first diluent is mannitol. In some embodiments, the mannitol is spray dried or crystalline. In some embodiments, the first diluent is calcium phosphate dibasic. In some embodiments, the second diluent is microcrystalline cellulose. In some embodiments, the second diluent is starch, polyethylene oxide, or hydroxypropyl methylcellulose (HPMC). In some embodiments, the binder is povidone (PVP). In some embodiments, the binder is hydroxypropyl cellulose (HPC). In some embodiments, the binder is hydroxypropyl methylcellulose (HPMC). In some embodiments, the composition further comprises a disintegrant. In some embodiments, the disintegrant is crospovidone or croscarmellose. In some embodiments, the croscarmellose is croscarmellose sodium. In some embodiments, a disintegrant is crospovidone. In some embodiments, the composition further comprises a large meso-porous silica excipient as an adsorbant or absorbant. In some embodiments, the large meso-porous silica excipient absorbs water. In some embodiments, the composition further comprises an intermediate meso-porous silica excipient as a glidant. In some embodiments, the intermediate meso-porous silica comprises syloid FP-244.

In some embodiments, the composition further comprises silicon dioxide. In some embodiments, the silicon dioxide is present in an amount of about 0.1% to about 10% by weight. In some embodiments, the silicon dioxide is present in an amount of about 0.1% to about 5% by weight. In some embodiments, the silicon dioxide is present in an amount of about 0.1%, about 0.2%, about 0.3%, about 0.4%, about 0.5%, about 0.6, about 0.7%, about 0.8%, about 0.9%, about 1%, about 1.5%, about 2%, about 2.5%, about 3%, about 3.5%, about 4%, about 4.5%, or about 5% by weight.

In some embodiments, the composition further comprises an intragranular phase. In some embodiments, the intragranular phase comprises silicon dioxide. In some embodiments, the silicon dioxide in the intragranular phase is present in an amount of about 0.1% to about 10% by weight. In some embodiments, the silicon dioxide in the intragranular phase is present in an amount of about 0.1% to about 5% by weight. In some embodiments, the silicon dioxide in the intragranular phase is present in an amount of about 0.1%, about 0.2%, about 0.3%, about 0.4%, about 0.5%, about 0.6, about 0.7%, about 0.8%, about 0.9%, about 1%, about 1.5%, about 2%, about 2.5%, about 3%, about 3.5%, about 4%, about 4.5%, or about 5% by weight.

In some embodiments, the intragranular phase does not comprise magnesium stearate. In some embodiments, the intragranular phase comprises niraparib, lactose monohydrate, microcrystalline cellulose, crospovidone, and povidone. In some embodiments, the intragranular phase comprises niraparib, lactose monohydrate, microcrystalline cellulose, croscarmellose, and hydroxypropyl cellulose (HPC). In some embodiments, the intragranular phase comprises niraparib, lactose monohydrate, microcrystalline cellulose, croscarmellose, and hydroxypropyl methylcellulose (HMPC). In some embodiments, the intragranular phase comprises niraparib, lactose monohydrate, microcrystalline cellulose, crospovidone, povidone, and a large meso-porous silica excipient as an adsorbant or absorbant/adsorbant or an intermediate meso-porous silica excipient as a glidant. In some embodiments, the intragranular phase comprises niraparib, lactose monohydrate, microcrystalline cellulose, crospovidone, povidone, and a large meso-porous silica excipient as an adsorbant or absorbant. In some embodiments, the intragranular phase comprises niraparib, lactose monohydrate, microcrystalline cellulose, crospovidone, povidone, and an intermediate meso-porous silica excipient as a glidant.

In some embodiments, the intragranular phase comprises magnesium stearate. In some embodiments, the intragranular phase comprises niraparib, microcrystalline cellulose, calcium phosphate dibasic, crospovidone, povidone, and magnesium stearate. In some embodiments, the intragranular phase comprises niraparib, microcrystalline cellulose, mannitol, croscarmellose, hydroxypropyl cellulose (HPC), and magnesium stearate. In some embodiments, the intragranular phase comprises niraparib, microcrystalline cellulose, mannitol, croscarmellose, hydroxypropyl methylcellulose (HPMC), and magnesium stearate. In some embodiments, the intragranular phase comprises niraparib, microcrystalline cellulose, mannitol, crospovidone, povidone, and magnesium stearate. In some embodiments, the intragranular phase comprises niraparib, lactose monohydrate, microcrystalline cellulose, crospovidone, and povidone. In some embodiments, the intragranular phase comprises niraparib, lactose monohydrate, microcrystalline cellulose, croscarmellose, and hydroxypropyl cellulose (HPC).

In some embodiments, the composition further comprises an extragranular phase. In some embodiments, the extragranular phase comprises magnesium stearate. In some embodiments, the extragranular phase comprises crospovidone. In some embodiments, the extragranular phase comprises croscarmellose.

In some embodiments, the extragranular phase comprises silicon dioxide. In some embodiments, the silicon dioxide in the extragranular phase is present in an amount of about 0.1% to about 10% by weight. In some embodiments, the silicon dioxide in the extragranular phase is present in an amount of about 0.1% to about 5% by weight. In some embodiments, the silicon dioxide in the extragranular phase is present in an amount of about 0.1% to about 2.5% by weight. In some embodiments, the silicon dioxide in the extragranular phase is present in an amount of about 0.1%, about 0.2%, about 0.3%, about 0.4%, about 0.5%, about 0.6, about 0.7%, about 0.8%, about 0.9%, about 1%, about 1.5%, about 2%, about 2.5%, about 3%, about 3.5%, about 4%, about 4.5%, or about 5% by weight.

In another aspect, the invention features a composition that is a tablet comprising any one of Formulations 1-42.

In embodiments, a tablet comprises any one of Formulations 1-6.

In embodiments, a tablet comprises any one of Formulations 7-18.

In embodiments, a tablet comprises any one of Formulations 19-30.

In embodiments, a tablet comprises any one of Formulations 31-42.

In some embodiments, the tablet has a disintegration time of about 30 seconds to about 300 seconds. In some embodiments, the tablet has a disintegration time of about 30 seconds to about 200 seconds. In some embodiments, the tablet has a disintegration time of about 30 seconds to about 150 seconds. In some embodiments, the tablet has a disintegration time of about 30 seconds, about 40 seconds, about 50 seconds, about 60 seconds, about 70 seconds, about 80 seconds, about 90 seconds, about 100 seconds, about 110 seconds, about 120 seconds, about 130 seconds, about 140 seconds, about 150 seconds, about 160 seconds, about 170 seconds, about 180 seconds, about 190 seconds, about 200 seconds, about 210 seconds, about 220 seconds, about 230 seconds, about 240 seconds, about 250 seconds, about 260 seconds, about 270 seconds, about 280 seconds, about 290 seconds, or about 300 seconds.

In some embodiments, the composition comprises less than 10% by weight of water. In some embodiments, the composition comprises less than 10% by weight of water after storage for 1 month at 40° C. and 75% relative humidity (RH). In some embodiments, the composition comprises less than 10% by weight of water after storage for 2 months at 40° C. and 75% relative humidity (RH).

In embodiments, a composition further comprises a coating layer. In embodiments, a coating layer comprises polyvinyl alcohol, titanium dioxide, polyethylene glycol, and/or talc. In embodiments, a coating layer is present in an amount of about 0.1% to about 5% by weight of the composition.

In another aspect, the invention features methods of making compositions (e.g., pharmaceutical compositions formulated as a tablet). In embodiments, a method described herein can be used to prepare a composition described herein (e.g., any of the tablet compositions described herein).

Provided herein in one aspect is a method of making a composition (e.g., a pharmaceutical composition formulated as a tablet) from wet granulation comprising niraparib comprising:
(a) forming an intragranular phase comprising
  i) combining niraparib, lactose monohydrate, and microcrystalline cellulose to form a composition comprising niraparib, lactose monohydrate, and microcrystalline cellulose; and
  ii) wet granulating the composition comprising niraparib, lactose monohydrate, and microcrystalline cellulose to form granules;
(b) forming an extragranular phase comprising
  iii) combining the granules with at least one pharmaceutically acceptable excipient to form a mixture; and
(c) forming a tablet by compressing the mixture obtained from step iii).

In some embodiments, the wet granulating from step ii) further comprises adding a binder. In some embodiments, the binder is a liquid binder. In some embodiments, he liquid binder is dissolved povidone. In some embodiments, the liquid binder is dissolved starch, dissolved hydroxypropyl cellulose (HPC), dissolved hydroxypropyl methylcellulose (HPMC), or liquid polyethylene glycol (PEG). In some embodiments, the liquid binder is a melted binder. In some embodiments, the melted binder is a hydrophilic polyethylene glycol (PEG), poloxamer, hydrophobic fatty acid, fatty alcohol, wax, hydrogenated vegetable oil, or glyceride. In some embodiments, the binder is a dry binder. In some embodiments, the dry binder is hydroxypropyl cellulose (HPC). In some embodiments, the dry binder is hydroxypropyl methylcellulose (HPMC). In some embodiments, the dry binder is povidone (PVP) or starch. In some embodiments, the wet granulating from step ii) further comprises wet-sieving. In some embodiments, the wet granulating from step ii) further comprises drying and dry sieving.

Provided herein in another aspect is a method of making a composition (e.g., a pharmaceutical composition formulated as a tablet) from moisture-activated dry granulation comprising niraparib comprising:
(a) forming an intragranular phase comprising
  i) combining niraparib, lactose monohydrate, and microcrystalline cellulose to form a composition comprising niraparib, lactose monohydrate, and microcrystalline cellulose; and
  ii) granulating the composition comprising niraparib, lactose monohydrate, and microcrystalline cellulose to form granules;
(b) forming an extragranular phase comprising
  iii) combining the granules with at least one pharmaceutically acceptable excipient to form a mixture; and
(c) forming a tablet by compressing the mixture obtained from step iii).

In some embodiments, the combining step i) further comprises an adsorbant, e.g. mesoporous colloidal silica or other adsorbant. In some embodiments, the granulating from step ii) further comprises adding a binder. In some embodiments, the binder is a liquid binder. In some embodiments, the liquid binder is dissolved povidone. In some embodiments, the liquid binder is water, dissolved starch, dissolved hydroxypropyl cellulose (HPC), dissolved hydroxypropyl methylcellulose (HPMC), or liquid polyethylene glycol (PEG). In some embodiments, the composition further comprises a dry binder. In some embodiments, water is added to the composition comprising the dry binder. In some embodiments, the granulating from step ii) further comprises drying and dry sieving. In some embodiments, the addition of a glidant. In some embodiments, the glidant is silicon dioxide. In some embodiments, the glidant is silicon dioxide, tribasic calcium phosphate, calcium silicate, cellulose, magnesium silicate, magnesium trisilicate, starch, talc, or mixtures thereof.

Provided herein in another aspect is a method of making a composition (e.g., a pharmaceutical composition formulated as a tablet) from dry granulation comprising niraparib comprising:
(a) forming an intragranular phase comprising
  i) combining niraparib, a diluent selected from mannitol and calcium phosphate dibasic, microcrystalline cellulose, and magnesium stearate to form a composition comprising niraparib, the diluent selected from mannitol and calcium phosphate dibasic, microcrystalline cellulose, and magnesium stearate; and
  ii) dry granulating the composition comprising niraparib, the diluent selected from mannitol and calcium phosphate dibasic, microcrystalline cellulose, and magnesium stearate to form granules;
(b) forming an extragranular phase comprising
  iii) combining the granules with at least one pharmaceutically acceptable excipient to form a mixture; and
(c) forming a tablet by compressing the mixture obtained from step iii).

In some embodiments, the composition further comprises a dry binder. In some embodiments, water is added to the composition comprising the dry binder. In some embodiments, combining niraparib, a diluent selected from mannitol and calcium phosphate dibasic, microcrystalline cellulose, and magnesium stearate to form a composition comprising niraparib, the diluent selected from mannitol and calcium phosphate dibasic, microcrystalline cellulose, and magnesium stearate from step i) further comprises blending the niraparib, a diluent selected from mannitol and calcium phosphate dibasic, microcrystalline cellulose, and magnesium stearate. In some embodiments, dry granulating from step ii) comprises slugging and milling. In some embodiments, the ribbon thickness is from about 0.1 mm to about 2 mm. In some embodiments, the composition from step i) further comprises silicon dioxide. In some embodiments, the at least one pharmaceutically acceptable excipient for combining the granules with at least one pharmaceutically acceptable excipient to form a mixture from step iii) is silicon dioxide. In some embodiments, the at least one pharmaceutically acceptable excipient for combining the granules with at least one pharmaceutically acceptable excipient to form a mixture from step iii) is magnesium stearate. In some embodiments, combining the granules with at least one pharmaceutically acceptable excipient to form a mixture from step iii) comprises blending the granules with at least one pharmaceutically acceptable excipient. In some embodiments, the composition from step i) is a blend composition.

In some embodiments, the amount of components used to form the intragranular phase is about 50% to about 98% by weight of the tablet composition. In some embodiments, the amount of components used to form the intragranular phase is about 85% to about 98% by weight of the tablet composition. In some embodiments, the amount of components used to form the intragranular phase is about 90% to about 98% by weight of the tablet composition. In some embodiments, the amount of components used to form the intragranular phase is about 92.5% to about 97.5% by weight of the tablet composition. In some embodiments, the amount of components used to form the intragranular phase is about 95% by weight of the tablet composition.

In some embodiments, the amount of components used to form the extragranular phase is about 2% to about 50% by weight of the tablet composition. In some embodiments, the amount of components used to form the extragranular phase is about 2% to about 15% by weight of the tablet composition. In some embodiments, the amount of components used to form the extragranular phase is about 2% to about 10% by weight of the tablet composition. In some embodiments, the amount of components used to form the extragranular phase is about 2.5% to about 7.5% by weight of the tablet composition. In some embodiments, the amount of components used to form the extragranular phase is about 5% by weight of the tablet composition. In some embodiments, the granules have a bulk density of about 0.2 to about 0.7 g/cm$^3$. In some embodiments, the granules have a tapped density of about 0.3 to about 0.9 g/cm$^3$.

Provided herein in one aspect is a method of making a composition (e.g., a pharmaceutical composition formulated as a tablet) comprising niraparib comprising:
(a) forming an intragranular phase comprising
   i) combining niraparib and at least one pharmaceutically acceptable excipient to form a composition comprising niraparib and at least one pharmaceutically acceptable excipient; and
   ii) granulating the composition comprising niraparib and at least one pharmaceutically acceptable excipient to form granules;
(b) forming an extragranular phase comprising
iii) combining the granules with at least one pharmaceutically acceptable excipient to form a mixture; and
(c) forming a tablet by compressing the mixture obtained from step iii);
wherein the tablet has at least one of the following:
   (1) the amount of components used to form the intragranular phase is about 50% to about 98% by weight of the tablet composition; and
   (2) the amount of components used to form the extragranular phase is about 2% to about 50% by weight of the tablet composition.

In some embodiments, the amount of components used to form the intragranular phase is about 50% to about 98% by weight of the tablet composition. In some embodiments, the amount of components used to form the intragranular phase is about 85% to about 98% by weight of the tablet composition. In some embodiments, the amount of components used to form the intragranular phase is about 90% to about 98% by weight of the tablet composition. In some embodiments, the amount of components used to form the intragranular phase is about 92.5% to about 97.5% by weight of the tablet composition. In some embodiments, the amount of components used to form the intragranular phase is about 95% by weight of the tablet composition.

In some embodiments, the amount of components used to form the extragranular phase is about 2% to about 50% by weight of the tablet composition. In some embodiments, the amount of components used to form the extragranular phase is about 2% to about 15% by weight of the tablet composition. In some embodiments, the amount of components used to form the extragranular phase is about 2% to about 10% by weight of the tablet composition. In some embodiments, the amount of components used to form the extragranular phase is about 2.5% to about 7.5% by weight of the tablet composition. In some embodiments, the amount of components used to form the extragranular phase is about 5% by weight of the tablet composition.

In some embodiments, the at least one pharmaceutically acceptable excipient from step i) is microcrystalline cellulose. In some embodiments, the at least one pharmaceutically acceptable excipient from step i) is lactose monohydrate, lactose anhydrous, mannitol, or calcium phosphate dibasic. In some embodiments, the at least one pharmaceutically acceptable excipient from step i) is magnesium stearate. In some embodiments, the at least one pharmaceutically acceptable excipient from step i) is silicon dioxide.

In some embodiments, the granulating from step ii) is wet granulating. In some embodiments, the wet granulating further comprises adding a binder. In some embodiments, the binder is a liquid binder. In some embodiments, the liquid binder is dissolved povidone. In some embodiments, the liquid binder is dissolved starch, dissolved hydroxypropyl cellulose (HPC), dissolved hydroxypropyl methylcellulose (HPMC), or liquid polyethylene glycol (PEG). In some embodiments, the liquid binder is a melted binder. In some embodiments, the melted binder is a hydrophilic polyethylene glycol (PEG), poloxamer, hydrophobic fatty acid, fatty alcohol, wax, hydrogenated vegetable oil, or glyceride. In some embodiments, the binder is a dry binder. In some embodiments, the dry binder is hydroxypropyl cellulose (HPC). In some embodiments, the dry binder is hydroxypropyl methylcellulose (HPMC). In some embodiments, the dry binder is povidone (PVP) or starch.

In some embodiments, the wet-granulating from step ii) further comprises wet-sieving. In some embodiments, the wet granulating from step ii) further comprises drying and dry sieving. In some embodiments, drying comprises the addition of a glidant. In some embodiments, the granulating from step ii) is dry granulating. In some embodiments, the dry granulating comprises slugging and milling. In some embodiments, the at least one pharmaceutically acceptable excipient for combining the granules with at least one pharmaceutically acceptable excipient to form a mixture from step iii) is silicon dioxide. In some embodiments, the at least one pharmaceutically acceptable excipient for combining the granules with at least one pharmaceutically acceptable excipient to form a mixture from step iii) is magnesium stearate.

The invention also features methods of treating a subject with compositions (e.g., a tablet) described herein.

Also provided in one aspect is a method of treating cancer, comprising administering to a subject in need thereof an effective amount of any one of the tablet compositions disclosed herein. In some embodiments, the cancer is selected from the group consisting of ovarian cancer, breast cancer, cervical cancer, endometrial cancer, prostate cancer, testicular cancer, pancreatic cancer, esophageal cancer, head and neck cancer, gastric cancer, bladder cancer, lung cancer, bone cancer, colon cancer, rectal cancer, thyroid cancer, brain and central nervous system cancers, glioblastoma, neuroblastoma, neuroendocrine cancer, rhabdoid cancer, keratoacanthoma, epidermoid carcinoma, seminoma, melanoma, sarcoma, bladder cancer, liver cancer, kidney cancer, myeloma, lymphoma, and combinations thereof. In some embodiments, the cancer is selected from the group consisting of ovarian cancer, fallopian tube cancer, primary peritoneal cancer, and combinations thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6 describes stability data for an exemplary formulation provided as a 100 mg niraparib tablet stored at 25° C./60% relative humidity (RH).

FIG. 7 describes stability data for an exemplary formulation provided as a 100 mg niraparib tablet stored at 40° C./75% RH.

FIG. 8 describes stability data for an exemplary formulation provided as a 300 mg niraparib tablet stored at 25° C./60% RH.

FIG. 9 describes stability data for an exemplary formulation provided as a 300 mg niraparib tablet stored at 40° C./75% RH.

DETAILED DESCRIPTION OF THE INVENTION

Figure 1:
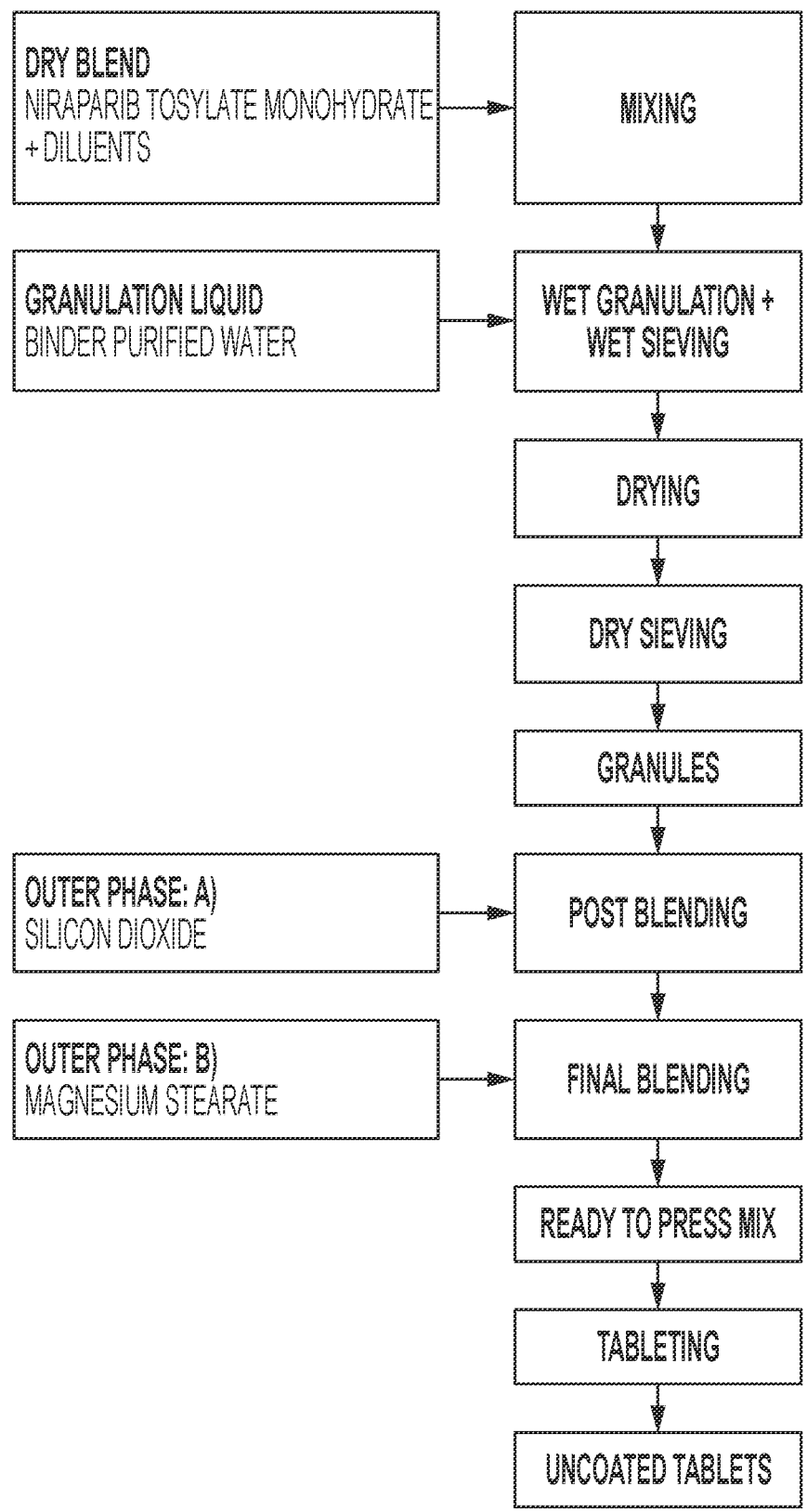
FIG. 1 is schematic of an exemplary wet granulation manufacturing process of the niraparib tablet.

Various pharmaceutical products are packaged in the form of tablets for oral dosage and release of a pharmaceutically active composition within an individual's body. Oral dosage pharmaceutical tablets typically contain a select amount of one or more pharmaceutically active compositions along with one or more inert excipient materials.

In some embodiments, the oral dosage pharmaceutical tablets disclosed herein improve the manufacturability of the tablet by reducing the stickiness/adherence of the active pharmaceutical ingredient during the table manufacturing process. In some embodiments, the oral dosage pharmaceutical tablets disclosed herein have improved desirable properties, those related to flow, tensile strength, hardness, disintegration and bonding of intragranular and extragranular materials. In some embodiments, the oral dosage pharmaceutical tablets disclosed herein impart desirable properties to the final blend used to compress to tablets improve tablet formation. In some embodiments, the oral dosage pharmaceutical tablets are prepared from granules with the desirable granulation size that provides good flow, tablet bonding, and desirable disintegration profiles of the tablet. In some embodiments, the oral dosage pharmaceutical tablets have a distribution of the intragranular phase vs. extragranular phase components that provides desirable disintegration profiles.

The tablet compositions described herein can also be used to provide improved methods for the treatment of cancer. For example, tablet compositions described herein can result in reduced variability in PK parameters as compared to other pharmaceutical dosage forms.

Definitions

The term "AUC" refers to the area under the time/plasma concentration curve after administration of the pharmaceutical composition. $AUC_{0-infinity}$ denotes the area under the plasma concentration versus time curve from time 0 to infinity; $AUC_{0-t}$ denotes the area under the plasma concentration versus time curve from time 0 to time t.

"Binders" are used to hold the components in a composition, such as a tablet composition, together. In some embodiments, binders are used to form granules. Examples of suitable binders include but are not limited to disaccharides, such as sucrose and lactose; polysaccharides and derivatives thereof, such as starches, microcrystalline cellulose, methyl cellulose, ethyl cellulose, hydroxy propyl methyl cellulose, hydroxypropyl cellulose; sugar alcohols, such as xylitol, sorbitol, or maltitol, gelatin, polyvinylpyrrolidone (polyvidone or povidone), polyethylene glycol, polyvinyl alcohol, and polymethacrylates. In some embodiments, the binder is liquid binder or a solution binder. Examples of liquid binders include but are not limited to water, gelatin, cellulose, cellulose derivatives, povidone, starch, sucrose and polyethylene glycol. In some embodiments, the gelatin, cellulose, cellulose derivatives, povidone, starch, sucrose or polyethylene glycol may be dissolved. For example, they may be dissolved in water. In some embodiments, the liquid binder is povidone (PVP). In some embodiments, the binder is a dry binder. Examples of suitable dry binder include but are not limited to cellulose, methyl cellulose, hydroxyl propyl cellulose, povidone, polyethylene glycol. In some embodiments, the dry binder is hydroxypropyl cellulose (HPC). In some embodiments, the liquid binder is a melted binder utilizing a molten liquid as a binder. With melted binders, there may be no need for aqueous or organic solvents. Accordingly, no drying step may be required which shortens the total processing time and lowers the cost of operation. Furthermore, water-sensitive materials can be processed using this nonaqueous method of granulation. Melted binders may include hydrophilic polyethylene glycols (PEGs) and poloxamers, and hydrophobic fatty acids, fatty alcohols, waxes, hydrogenated vegetable oils and glycerides.

"Blood plasma concentration" refers to the concentration of compounds provided herein in the plasma component of blood of a subject The term "bioequivalent" means the absence of a significant difference in the rate and extent to which the active ingredient or active moiety in pharmaceutical equivalents or pharmaceutical alternatives becomes available at the site of drug action when administered at the same molar dose under similar conditions in an appropriately designed study. In practice, two products are considered bioequivalent if the 90% confidence interval of the $C_{max}$, AUC, or, optionally, $T_{max}$ is within the range of 80.00% to 125.00%.

"Bulk density", as used herein, refers to the ratio of the mass of an untapped powder sample and its volume including the contribution of the interparticulate void volume. Bulk density indicates mass of a powder material that can be filled in per unit volume. For example, granules present in the pharmaceutical composition can have a bulk density more than or equal to 0.5 $g/cm^3$.

The term "$C_{max}$" refers to the maximum concentration of niraparib in the blood following administration of the pharmaceutical composition.

The term "cancer" includes both solid tumors and hematological malignancies. Cancers include, but are not limited to, ovarian cancer, breast cancer, cervical cancer, endometrial cancer, prostate cancer, testicular cancer, pancreatic cancer, esophageal cancer, head and neck cancer, gastric cancer, bladder cancer, lung cancer (e.g., adenocarcinoma, NSCLC and SCLC), bone cancer (e.g., osteosarcoma), colon cancer, rectal cancer, thyroid cancer, brain and central nervous system cancers, glioblastoma, neuroblastoma, neuroendocrine cancer, rhabdoid cancer, keratoacanthoma, epidermoid carcinoma, seminoma, melanoma, sarcoma (e.g., liposarcoma), bladder cancer, liver cancer (e.g., hepatocellular carcinoma), kidney cancer (e.g., renal cell carcinoma), myeloid disorders (e.g., AML, CML, myelodysplastic syndrome and promyelocytic leukemia), and lymphoid disorders (e.g., leukemia, multiple myeloma, mantle cell lymphoma, ALL, CLL, B-cell lymphoma, T-cell lymphoma, Hodgkin's lymphoma, non-Hodgkin's lymphoma, hairy cell lymphoma).

The term "composition", as in pharmaceutical composition, is intended to encompass a drug product comprising niraparib or its pharmaceutically acceptable salts, esters, solvates, polymorphs, stereoisomers or mixtures thereof, and the other inert ingredient(s) (pharmaceutically acceptable excipients). Such pharmaceutical compositions may be, in certain embodiments, synonymous with "formulation" and "dosage form". Pharmaceutical composition of the invention include, but is not limited to, granules, tablets (single layered tablets, multilayered tablets, mini tablets, bioadhesive tablets, caplets, matrix tablets, tablet within a tablet, mucoadhesive tablets, modified release tablets, orally disintegrating tablets, pulsatile release tablets, timed release tablets, delayed release, controlled release, extended release and sustained release tablets), capsules (hard and soft or liquid filled soft gelatin capsules), pills, troches, sachets, powders, microcapsules, minitablets, tablets in capsules and microspheres, matrix composition and the like. In some embodiments, the pharmaceutical composition refers to tablets. In some embodiments, pharmaceutical composition encompasses the bulk blend of the compositions provided herein prior to processing into final dosage form. In some embodiments, pharmaceutical composition encompasses an intermediate blend or composition comprising niraparib in formulation with one or more excipients of the compositions provided herein.

"Immediate release" refers to a dosage form which releases active agent substantially immediately upon contact with gastric juices and will result in substantially complete dissolution within about 1 hour. Immediate release (IR) components can also be referred to as instant release.

By "$D_{50}$", it is meant that 50% of the particles are below and 50% of the particles are above a defined measurement. $D_{50}$ can be used to describe different parameters (volume, length, number, area, etc.). $D_{50}$ as used herein indicates the volume-weighted median diameter, for example, as measured by a laser/light scattering method or equivalent, wherein 50% of the particles, by volume, have a smaller diameter, while 50% by volume have a larger diameter. The volume weighted $D_{50}$ also relates to the percentage of weight of the particle under a certain size. For example, a $D_{50}$ of 500 nm means that 50% of the particulate mass is less than 500 nm in diameter and 50% of the particulate mass is greater than 500 nm in diameter. The particle size can be measured by conventional particle size measuring techniques well known to those skilled in the art. Such techniques include, for example, sedimentation field flow fractionation, photon correlation spectroscopy, light scattering (e.g., with a Microtrac UPA 150), laser diffraction and disc centrifugation. For the purposes of the compositions, formulations and methods described herein, effective particle size is the volume median diameter as determined using laser/light scattering instruments and methods, e.g. a Horiba LA-910, or Horiba LA-950. Similarly, "$D_{90}$" is the volume-weighted diameter, wherein 90% of the particles, by volume, have a smaller diameter, while 10% by volume have a larger diameter and "$D_{10}$" is the volume-weighted diameter, wherein 10% of the particles, by volume, have a smaller diameter, while 90% by volume have a larger diameter. It is sometimes useful to express the $D_{50}$ value after sonication for 1 minute or less using about 40 watts of sonicating power at room temperature (15° C. to 30° C.). This low power and short period can break up very loose aggregates which will not typically have a negative impact on the in vivo performance of the composition in a subject.

"Diluents" increase bulk of the composition to facilitate compression or create sufficient bulk for homogenous blend for tablet formulations. As used herein, diluents are synonyms with "filler". Such compounds include e.g., lactose such as lactose monohydrate, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like. Combinations of one or more diluents can also be used. In some embodiments, the diluent is lactose monohydrate. In some embodiments, the diluent is lactose anhydrous. In some embodiments, the diluent is mannitol. In some embodiments, the diluent is calcium phosphate dibasic. In some embodiments, the diluent is microcrystalline cellulose. In some embodiments, one or more diluents affect the brittleness of the composition. In some embodiments, one or more diluents contribute to the plasticity of the composition. In some embodiments, the first diluent is used to adjust the brittleness of the composition and the second diluent is used to adjust the plasticity of the composition. In some embodiments, the first diluent is lactose monohydrate, lactose anhydrous, mannitol, or calcium phosphate dibasic. In some embodiments, the second diluent is microcrystalline cellulose, starch, polyethylene oxide, hydroxypropyl methylcellulose (HPMC).

"Disintegrant" expands and dissolves when wet causing a solid dosage form or tablet to break apart, for example, in the digestive tract, releasing the active ingredients for absorption. Disintegrants ensure that when the tablet is in contact with water, it rapidly breaks down into smaller fragments, facilitating dissolution. In some embodiments, the disintegrant is crospovidone or croscarmellose.

The terms "effective amount" or "therapeutically effective amount," as used herein, refer to a sufficient amount of the niraparib being administered that would be expected to relieve to some extent one or more of the symptoms of the disease or condition being treated. For example, the result of administration of niraparib disclosed herein is reduction and/or alleviation of the signs, symptoms, or causes of cancer. For example, an "effective amount" for therapeutic uses is the amount of niraparib, including a formulation as disclosed herein required to provide a decrease or amelioration in disease symptoms without undue adverse side effects. The term "therapeutically effective amount" includes, for example, a prophylactically effective amount. It is understood that an "an effective amount" or a "therapeutically effective amount" varies, in some embodiments, from subject to subject, due to variation in metabolism of the compound administered, age, weight, general condition of the subject, the condition being treated, the severity of the condition being treated, and the judgment of the prescribing physician.

The terms "enhance" or "enhancing" refers to an increase or prolongation of either the potency or duration of a desired effect of niraparib, or a diminution of any adverse symptomatology that is consequent upon the administration of the therapeutic agent. Thus, in regard to enhancing the effect of niraparib disclosed herein, the term "enhancing" refers to the ability to increase or prolong, either in potency or duration, the effect of other therapeutic agents that are used in combination with niraparib disclosed herein. An "enhancing-effective amount," as used herein, refers to an amount of niraparib or other therapeutic agent which is adequate to enhance the effect of another therapeutic agent or niraparib in a desired system. When used in a patient, amounts effective for this use will depend on the severity and course of the disease, disorder or condition, previous therapy, the patient's health status and response to the drugs, and the judgment of the treating physician.

The term "excipient" means a pharmacologically inactive component such as a diluent, lubricant, surfactant, carrier, or the like. Excipients that are useful in preparing a pharmaceutical composition are generally safe, non-toxic and are acceptable for human pharmaceutical use. Reference to an excipient includes both one and more than one such excipient. Co-processed excipients are also covered under the scope of present invention.

"Filling agents" or "fillers" include compounds such as lactose, lactose monohydrate, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Friability" means the condition of being friable, which is the ability of a solid substance to be reduced to smaller pieces. Friability as related to certain solid dosage forms may be evaluated according to: 1) European Pharmacopoeia (Ph. Eur.): Supplement 6.6 (published June 2009, official January 2010), Friability of Uncoated Tablets (reference 01/2010:20907); 2) Japanese Pharmacopoeia (JP): The JP General Information 26. Tablet Friability Test as it appears in the JP Fifteenth Edition (Mar. 31, 2006, The Ministry of Health, Labour and Welfare Ministerial Notification No. 285), officially updated by errata published by MHLW at http://www.std.pmda.go.jp/jpPUB/Data/ENG/jpdata/H201105_p15_errata.pdf on Nov. 5, 2008; or 3) 5.2.3 United States Pharmacopeia (USP): <1216> Tablet Friability, official in USP 32, May 1, 2009. Each of the afore-mentioned references are incorporated by reference herein. Friability may also be determined by updated versions of these references cited above, as applicable.

"Granulation" as used herein refers to process of binding particles of a dry powder composition through agglomeration to provide larger particles, known as granules that allow for production of pharmaceutical dosage form, such as tablets. Granulation is most often divided into two types: wet granulation, which requires a liquid in the process, and dry granulation, which does not require any liquid. Wet granulation uses a granulation liquid (binder/solvent) to facilitate the agglomeration by formation of a wet mass by adhesion while dry granulation uses mechanical compression, such as slugging, or compaction, such as roller compaction, to facilitate agglomeration. In roller compaction, ribbons are produced by passing the blend between the roller compactor rolls. The roll pressure and gap distance (set between the two rolls) are key parameters that influence the ribbon thickness. The ribbon thickness is important in tailoring the final particle size of the granulation, as it will affect the milling efficiency of the ribbons. Ribbon thickness may be measured with a caliper throughout the process. One method of measuring thickness is to obtain a rectangular sample of ribbon, at least 1 in (2.54 cm) from the compaction process. The dimensions (length, width, and thickness) are measured using a caliper or other device for measuring accurately to between one tenth or hundredth of an inch. Another parameter that may be measured is ribbon density, which is calculated by dividing the mass of the ribbon sample divided by the approximate volume (length×width×thickness).

"Intragranular phase" refers to the intragranular phase of the tablet, which comprises the granules that are prepared for tableting and comprises the components or excipients in the composition prior to granule formation. "Extragranular phase" refers to the extragranular phase of the tablet and comprises the excipients or components that are added to the composition after granule formation and before compression to provide a tablet.

"Lubricants" and "glidants" are compounds that prevent, reduce or inhibit adhesion or friction of materials. Without being limited as to theory, glidants prevent, reduce or inhibit adhesion of powders in a blend. For example, they may prevent, reduce or inhibit intra-particulate friction or may prevent, reduce or inhibit electrostatic charging of a powder. Lubricants may prevent, reduce or inhibit the adhesion of a powder to the surfaces into which it comes in contact. While glidants and lubricants may be any compound that provided the desired function, exemplary lubricants and glidants include, e.g., stearic acid, magnesium stearate, calcium hydroxide, talc, sodium stearyl fumarate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like. In some embodiments, a glidant is silicon dioxide. In some embodiments, a glidant is an intermediate meso-porous silica excipient.

As used interchangeably herein, the term "patient" or "subject" refers to any organism to which provided compound or compounds described herein are administered in accordance with the present invention e.g., for experimental, diagnostic, prophylactic, and/or therapeutic purposes. Typical subjects include animals. The term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone. In embodiments, animals are mammals such as mice, rats, rabbits, non-human primates, and humans; insects; worms; etc. In embodiments, a subject is a human. In some embodiments, a subject may be suffering from, and/or susceptible to a disease, disorder, and/or condition (e.g., cancer). As used herein, a "patient population" or "population of subjects" refers to a plurality of patients or subjects.

"Pharmacodynamics" refers to the factors which determine the biologic response observed relative to the concentration of drug.

"Pharmacokinetics" refers to the factors which determine the attainment and maintenance of the appropriate concentration of drug.

"Moisture-activated dry granulation" (MADG) or "moist granulation" refers process for granulation that uses liquid, such as water, to activate the binder and initiate agglomeration. This process involves wet agglomeration of the powder particles, which is facilitated by the addition of an amount of a liquid, such as water, and moisture adsorption or distribution. Moisture adsorption or distribution comprises the addition of a moisture-absorbing material or adsorbant or absorbant after agglomeration to facilitate the absorption of excess moisture. Examples of suitable moisture-absorbing materials or adsorbant or absorbant include but are not limited to microcrystalline cellulose or silicon dioxide. In some embodiments, the adsorbant or absorbant is a large meso-porous silica excipient, bentonite, talc, microcrystalline cellulose, charcoal, fumed silica, magnesium carbonate, or similar excipients.

"Ready-to-use" refers to pharmaceutical compositions or medical products that can be used without the needs of further changing, modifying, or optimizing the composition or the product prior to administration, for example through dilution, reconstitution, sterilization, etc.

"Ribbon" and "ribbon thickness" are referred to with respect to a type of dry granulation that utilizes roll or roller compaction. In some embodiments of roll or roller compaction, powder is fed by gravity or by means of a screw through two counter-rotating rollers, rearranging the particles by the compaction pressure applied by the rollers, thus inducing a densification of the resulting material. The resulting material of roll or roller compaction is known as a "ribbon", wherein a uniform and continuous flow of material is provided by the feeding system to form a "ribbon" of desired "ribbon thickness". Ribbon thickness may be measured by any of the typical methods utilized in the art.

"Stable" or "stability" with respect to particle size distribution means the particle size distribution, e.g. $D_{50}$ or D90 does not substantially change (greater than 50%) after an initial time is defined (e.g., after milling or a curing period (1 to 3 weeks)). For example, the stable niraparib particles described herein in a solid oral dosage form will not show an increase in effective particle size of greater than 50% up to 3, 6, 9, 12, 24 or 36 months storage at room temperature (15° C. to 25° C.). "Stable" or "stability" with respect to degradation of niraparib means that the number of impurities or degradation products does not substantially change (greater than 50%) after an initial time is defined. In some embodiments, the formulations described herein will not produce niraparib degradation impurities up to 3, 6, 9, 12, 24 or 36 months storage at room temperature (15° C. to 25° C.) at individual levels of about greater than 0.1% by weight as compared to the impurity levels at the initial time designation.

"Storage" with respect to the composition, including in solid dosage form, means storage in any container system or type for pharmaceutical use is an article which holds or is intended to contain a drug and is or may be in direct contact with it. In certain storage conditions, the container should provide the dosage form with adequate protection from factors (e.g., temperature, light) that can cause a degradation in the quality of that dosage form over its shelf life. Storage may occur in a blister (e.g. a multi-dose container consisting of two layers, of which one is shaped to contain the individual doses), a bottle (e.g. a container with a more or less pronounced neck and usually a flat bottom), a single-dose container (e.g. a container for single doses of solid, semi-solid or liquid preparations, a strip (e.g. a multi-dose container consisting of two layers, usually provided with perforations, suitable for containing single doses of solid or semi-solid preparations, a bag (e.g. a container consisting of surfaces, whether or not with a flat bottom, made of flexible material, closed at the bottom and at the sides by sealing; the top may be closed by fusion of the material, depending on the intended use), or an open dish.

The term "subject" is used to mean an animal, preferably a mammal, including a human or non-human. The terms patient and subject may be used interchangeably.

"Tablet" as used herein refers to a dosage form in which particles of a drug substance or pharmaceutical agent, such as niraparib, and certain excipients, such as any one of the excipients described herein, are pressed, compacted, or extruded together. Tablets can be made in a variety of shapes, including round, or elongated, such as flattened ovoid or cylindrical shapes. In some embodiments, the tablet is prepared from direct compression using suitable punches or dies. In some embodiments, the tablet is prepared from injection or compression molding using suitable molds fitted to a compression unit. In some embodiments, the tablet is prepared from granulation, such as but not limited to fluid bed or high shear granulation or roller compaction, followed by compression. In some embodiments, the tablet is prepared from extrusion of a paste into a mold or to an extrudate to be cut into lengths. In some embodiments, the tablet is a solid tablet.

A "therapeutically effective amount" or "effective amount" is that amount of a pharmaceutical agent to achieve a pharmacological effect. The term "therapeutically effective amount" includes, for example, a prophylactically effective amount. An "effective amount" of niraparib is an amount needed to achieve a desired pharmacologic effect or therapeutic improvement without undue adverse side effects. The effective amount of a niraparib will be selected by those skilled in the art depending on the particular patient and the disease. It is understood that "an effective amount" or a "therapeutically effective amount" can vary from subject to subject, due to variation in metabolism of niraparib, age, weight, general condition of the subject, the condition being treated, the severity of the condition being treated, and the judgment of the prescribing physician. As used herein, amelioration or lessening of the symptoms of a particular disease, disorder or condition by administration of a particular compound or pharmaceutical composition refers to any decrease of severity, delay in onset, slowing of progression, or shortening of duration, whether permanent or temporary, lasting or transient that is attributed to or associated with administration of the compound or composition.

The term "$t_{max}$" refers to the time in hours when $C_{max}$ is achieved following administration of the pharmaceutical composition.

The terms "treat," "treating" or "treatment," as used herein, include alleviating, abating or ameliorating a disease or condition, for example cancer, symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Other objects, features, and advantages of the methods and compositions described herein will become apparent from the following detailed description. It should be understood, however, that the detailed description and the specific examples, while indicating specific embodiments, are given by way of illustration only.

Niraparib Formulations

The present invention recognizes the need to provide improved dosage forms of niraparib having desirable disintegration profiles, pharmacokinetic characteristics, flow properties, and/or good storage stability. Additionally, such improved dosage forms can be useful in methods of treatment (e.g., methods of treating cancer).

The present invention relates to a process for the preparation of a solid, orally administrable pharmaceutical composition, comprising a poly (adenosine diphosphate [ADP]-ribose) polymerase (PARP)-1 and -2 inhibitor, and its use for the prophylaxis and/or treatment of diseases. The present invention relates to solid dosage forms of niraparib and pharmaceutically acceptable salts thereof (e.g., niraparib tosylate monohydrate), having desirable pharmacokinetic characteristics which exhibit, for example, favorable storage stability and disintegration properties.

Niraparib has the following structure:

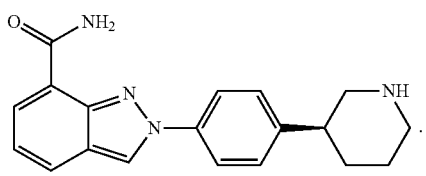 [SMILES: NC(=O)c1cccc2cn(-c3ccc([C@@H]4CCCNC4)cc3)nc12]

Niraparib is an orally available, selective poly(ADP-ribose) polymerase (PARP) 1 and 2 inhibitor. The chemical name for niraparib tosylate monohydrate is 2-{4-[(3S)-piperidin-3-yl]phenyl}-2H-indazole 7-carboxamide 4-methylbenzenesulfonate hydrate (1:1:1) and it has the following chemical structure:

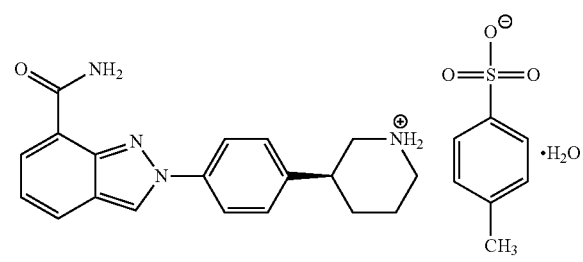 [SMILES: NC(=O)c1cccc2cn(-c3ccc([C@@H]4CCC[NH2+]C4)cc3)nc12 ; Cc1ccc(S(=O)(=O)[O-])cc1 ; O]

The empirical molecular formula for niraparib is $C_{26}H_{30}N_4O_5S$ and its molecular weight is 510.61. Niraparib tosylate monohydrate drug substance is a white to off-white, non-hygroscopic crystalline solid. Niraparib solubility is pH independent below the pKa of 9.95, with an aqueous free base solubility of 0.7 mg/mL to 1.1 mg/mL across the physiological pH range.

Niraparib is a selective poly(ADP-ribose) polymerase (PARP) 1 and 2 inhibitor which selectively kills tumor cells in vitro and in mouse xenograft models. PARP inhibition leads to irreparable double strand breaks (DSBs), use of the error-prone DNA repair pathway, resultant genomic instability, and ultimately cell death. Additionally, PARP trapped at genetic lesions as a result of the suppression of autoparylation can contribute to cytotoxicity.

Niraparib, tradename ZEJULA is indicated for the maintenance or treatment of adult patients with recurrent epithelial ovarian, fallopian tube, or primary peritoneal cancer following a complete or partial response to platinum-based chemotherapy. Each ZEJULA capsule contains 100 mg of niraparib (as tosylate monohydrate). The hard capsules may have a white body with "100 mg" printed in black ink, and a purple cap with "niraparib" printed in white ink. The current recommended dose of ZEJULA as monotherapy is three 100 mg capsules taken orally once daily, equivalent to a total daily dose of 300 mg.

Provided herein is an oral composition containing niraparib or its pharmaceutically acceptable salts. In some embodiments, the oral composition includes from about 20 wt % to about 80 wt % of niraparib for treatment of a disorder or condition such as cancer; and a pharmaceutically acceptable carrier, wherein the niraparib is distributed with throughout the pharmaceutically acceptable carrier. In some embodiments, the oral composition includes from about 20 wt % to about 60 wt % of niraparib for treatment of a disorder or condition such as cancer; and a pharmaceutically acceptable carrier, wherein the niraparib is distributed with substantial uniformity throughout the pharmaceutically acceptable carrier. In some embodiments, the oral composition includes from about 35 wt % to about 55 wt % of niraparib for treatment of a disorder or condition such as cancer; and a pharmaceutically acceptable carrier, wherein the niraparib is distributed with substantial uniformity throughout the pharmaceutically acceptable carrier.

In embodiments, an oral composition is a tablet.

In some embodiments, the disorder or condition is cancer, for example, ovarian cancer.

In some embodiments, the niraparib is a pharmaceutically acceptable salt thereof. In some embodiments, the pharmaceutically acceptable salt is niraparib tosylate monohydrate.

In some embodiments, the pharmaceutical composition comprises about 10 mg to about 2000 mg of niraparib tosylate monohydrate. In some embodiments, the pharmaceutical composition comprises about 10 mg to about 1000 mg of niraparib tosylate monohydrate. In some embodiments, the pharmaceutical composition comprises about 10 mg to about 525 mg of niraparib tosylate monohydrate. In some embodiments, the pharmaceutical composition comprises about 425 mg to about 525 mg of niraparib tosylate monohydrate. In some embodiments, the pharmaceutical composition comprises about 50 mg to about 300 mg of niraparib tosylate monohydrate. In some embodiments, the pharmaceutical composition comprises about 50 mg to about 525 mg of niraparib tosylate monohydrate. For example, the pharmaceutical composition can comprise about 100 mg to about 200 mg of niraparib tosylate monohydrate. For example, the pharmaceutical composition can comprise about 125 mg to about 175 mg of niraparib tosylate monohydrate.

The formulation can comprise one or more components, including niraparib. The components can be combined to create granules that are then compressed to form tablets.

The niraparib may be present in the formulation as a pharmaceutically acceptable salt. For example, the niraparib can be niraparib tosylate monohydrate.

Exemplary formulations include those described herein.

In one embodiment, an exemplary niraparib formulation comprises 478.0 mg of niraparib tosylate monohydrate, 203.5 mg of lactose monohydrate, 203.5 mg of microcrystalline cellulose, 40.0 mg of crospovidone, and 20.0 mg of povidone for the intragranular phase; and 40.0 mg of crospovidone, 5.0 mg of silicon dioxide, and 10.0 mg of magnesium stearate for the extragranular phase. In one embodiment, an exemplary niraparib formulation comprises 47.8% by weight of niraparib tosylate monohydrate, 20.4% by weight of lactose monohydrate, 20.4% by weight of microcrystalline cellulose, 4.0% by weight of crospovidone, and 2.0% by weight of povidone for the intragranular phase; and 4.0% by weight of crospovidone, 0.5% by weight of silicon dioxide, and 1.0% by weight of magnesium stearate for the extragranular phase.

In one embodiment, an exemplary niraparib formulation comprises 478.0 mg of niraparib tosylate monohydrate, 193.5 mg of lactose monohydrate, 193.5 mg of microcrystalline cellulose, 40.0 mg of croscarmellose, and 40.0 mg of hydroxypropyl cellulose for the intragranular phase; and 40.0 mg of croscarmellose sodium, 5.0 mg of silicon dioxide, and 10.0 mg of magnesium stearate for the extragranular phase. In one embodiment, an exemplary niraparib formulation comprises 47.8% by weight of niraparib tosylate monohydrate, 19.4% by weight of lactose monohydrate, 19.4% by weight of microcrystalline cellulose, 4.0% by weight of croscarmellose, and 4.0% by weight of hydroxypropyl cellulose for the intragranular phase; and 4.0% by weight of croscarmellose sodium, 0.5% by weight of silicon dioxide, and 1.0% by weight of magnesium stearate for the extragranular phase.

In one embodiment, an exemplary niraparib formulation comprises 478.0 mg of niraparib tosylate monohydrate, 178.5 mg of lactose monohydrate, 178.5 mg of microcrystalline cellulose, 40.0 mg of crospovidone, 40.0 mg of povidone, and 25.0 mg of silicon dioxide for the intragranular phase; and 40.0 mg of crospovidone, 10.0 mg of silicon dioxide, and 10.0 mg of magnesium stearate for the extragranular phase. In one embodiment, an exemplary niraparib formulation comprises 47.8% by weight of niraparib tosylate monohydrate, 17.9% by weight of lactose monohydrate, 17.9% by weight of microcrystalline cellulose, 4.0% by weight of crospovidone, 4.0% by weight of povidone, and 2.5% by weight of silicon dioxide for the intragranular phase; and 4.0% by weight of crospovidone, 1.0% by weight of silicon dioxide, and 1.0% by weight of magnesium stearate for the extragranular phase.

In one embodiment, an exemplary niraparib formulation comprises 478.0 mg of niraparib tosylate monohydrate, 201.0 mg of microcrystalline cellulose, 201.0 mg of calcium phosphate dibasic, 40.0 mg of crospovidone, 20.0 mg of povidone, and 5.0 mg magnesium stearate for the intragranular phase; and 40.0 mg of crospovidone, 5.0 mg of silicon dioxide, and 10.0 mg of magnesium stearate for the extragranular phase. In one embodiment, an exemplary niraparib formulation comprises 47.8% by weight of niraparib tosylate monohydrate, 20.1% by weight of microcrystalline cellulose, 20.1% by weight of calcium phosphate dibasic, 4.0% by weight of crospovidone, 2.0% by weight of povidone, and 0.5% by weight magnesium stearate for the intragranular phase; and 4.0% by weight of crospovidone, 0.5% by weight of silicon dioxide, and 1.0% by weight of magnesium stearate for the extragranular phase.

In one embodiment, an exemplary niraparib formulation comprises 478.0 mg of niraparib tosylate monohydrate, 201.0 mg of microcrystalline cellulose, 201.0 mg of mannitol, 40.0 mg of croscarmellose sodium, 20.0 mg of hydroxylpropyl cellulose, and 5.0 mg magnesium stearate for the intragranular phase; and 40.0 mg of croscarmellose sodium, 5.0 mg of silicon dioxide, and 10.0 mg of magnesium stearate for the extragranular phase. In one embodiment, an exemplary niraparib formulation comprises 47.8% by weight of niraparib tosylate monohydrate, 20.1% by weight of microcrystalline cellulose, 20.1% by weight of mannitol, 4.0% by weight of croscarmellose sodium, 2.0% by weight of hydroxylpropyl cellulose, and 0.5% by weight magnesium stearate for the intragranular phase; and 4.0% by weight of croscarmellose sodium, 0.5% by weight of silicon dioxide, and 1.0% by weight of magnesium stearate for the extragranular phase.

In one embodiment, an exemplary niraparib formulation comprises 478.0 mg of niraparib tosylate monohydrate, 201.0 mg of microcrystalline cellulose, 201.0 mg of mannitol, 40.0 mg of crospovidone, 20.0 mg of povidone, and 5.0 mg magnesium stearate for the intragranular phase; and 40.0 mg of crospovidone, 5.0 mg of silicon dioxide, and 10.0 mg of magnesium stearate for the extragranular phase. In one embodiment, an exemplary niraparib formulation comprises 47.8% by weight of niraparib tosylate monohydrate, 20.1% by weight of microcrystalline cellulose, 20.1% by weight of mannitol, 4.0% by weight of crospovidone, 2.0% by weight of povidone, and 0.5% by weight of magnesium stearate for the intragranular phase; and 4.0% by weight of crospovidone, 0.5% by weight of silicon dioxide, and 1.0% by weight of magnesium stearate for the extragranular phase.

Niraparib Tablet Compositions

Exemplary tablet compositions, including exemplary excipients, are described herein.

In embodiments, the invention features a tablet composition comprising niraparib in an effective amount of niraparib to inhibit polyadenosine diphosphate ribose polymerase (PARP) when administered to a subject in need thereof, wherein the tablet comprises an intragranular phase and an extragranular phase, and wherein: (a) at least one component of the intragranular phase is a diluent, a binder, a disintegrant, a glidant, or a lubricant; and/or (b) at least one component of the extragranular phase is a disintegrant, a glidant, or a lubricant.

In another aspect is provided a tablet composition comprising niraparib in an effective amount of niraparib to inhibit polyadenosine diphosphate ribose polymerase (PARP) when administered to a subject in need thereof, wherein the tablet comprises an intragranular phase and an extragranular phase.

In embodiments, a tablet composition comprises niraparib in an amount of about 50 mg to about 350 mg based on the niraparib free base. In embodiments, a tablet composition comprises niraparib tosylate monohydrate in an amount of about 100 mg to about 550 mg. In embodiments, a tablet composition comprises niraparib tosylate monohydrate in an amount that is about 40-50% by weight of the tablet composition.

In embodiments, the intragranular phase comprises a diluent (e.g., a first diluent) in an amount that is about 7.5-15%, about 8-14%, or about 9-11% by weight of the tablet composition. In embodiments, the intragranular phase comprises a second diluent in an amount that is about 25-40%, about 30-40%, or about 30-35% by weight of the tablet composition. In embodiments, the intragranular phase comprises a binder in an amount that is about 1-3% by weight of the tablet composition. In embodiments, the intragranular phase comprises a disintegrant in an amount that is about 0.1-2% or about 0.5%-1.5% by weight of the tablet composition. In embodiments, the intragranular phase comprises a glidant, adsorbant, or absorbant in an amount that is about 1-5% or about 2-4% by weight of the tablet composition. In embodiments, the intragranular phase comprises a lubricant in an amount that is about 0.1-2% by weight of the tablet composition. In embodiments, the extragranular phase comprises a disintegrant in an amount that is about 0.1-2% by weight of the tablet composition. In embodiments, the extragranular phase comprises a glidant or adsorbant or absorbant in an amount that is about 0.1-2% by weight of the tablet composition. In embodiments, the extragranular phase comprises a lubricant in an amount that is about 0.1-2% by weight of the tablet composition.

In one aspect disclosed herein is tablet composition comprising: a) an effective amount of niraparib to inhibit polyadenosine diphosphate ribose polymerase (PARP) when administered to a subject in need thereof; b) a first diluent selected from lactose monohydrate, lactose anhydrous, mannitol, and calcium phosphate dibasic; c) magnesium stearate; d) a second diluent selected from microcrystalline cellulose, starch, polyethylene oxide, and hydroxypropyl methylcellulose (HPMC); and e) a binder selected from povidone (PVP), hydroxypropyl cellulose (HPC), and hydroxypropyl methylcellulose (HPMC).

In another aspect disclosed herein is tablet composition comprising the following components on a weight percentage basis:
(a) in an intragranular portion:
  (i) about 40-50% niraparib tosylate monohydrate;
  (ii) about 8-14% of a first diluent;
  (iii) about 30-40% of a second diluent;
  (iv) about 1-3% of a binder;
  (v) about 0.1-2% of a disintegrant;
  (vi) about 2-4% of a glidant or adsorbant or absorbant; and
  (vii) about 0.1-2% of a lubricant;
(b) in an extragranular portion:
  (i) about 0.1-2% of a disintegrant;
  (ii) about 0.1-2% of a glidant or adsorbant or absorbant; and
  (iii) about 0.1-2% of a lubricant.

In another aspect disclosed herein is tablet composition comprising the following components on a weight percentage basis:
(a) in an intragranular portion:
  (i) about 40-50% niraparib tosylate monohydrate;
  (ii) about 9-11% of a first diluent;
  (iii) about 30-40% of a second diluent;
  (iv) about 1-3% of a binder;
  (v) about 0.1-2% of a disintegrant;
  (vi) about 2-4% of a glidant or adsorbant or absorbant; and
  (vii) about 0.1-2% of a lubricant;
(b) in an extragranular portion:
  (i) about 0.1-2% of a disintegrant;
  (ii) about 0.1-2% of a glidant or adsorbant or absorbant; and
  (iii) about 0.1-2% of a lubricant.

In another aspect provided herein is a composition comprising a tablet comprising the following components on a weight percentage basis:
(a) in an intragranular portion:
  (i) about 40-50% niraparib tosylate monohydrate;
  (ii) about 9-40% of a diluent;
  (iii) about 1-3% of a binder;
  (iv) about 0.1-2% of a disintegrant;
  (v) about 2-4% of a glidant or adsorbant or absorbant; and
  (vi) about 0.1-2% of a lubricant;
(b) in an extragranular portion:
  (i) about 0.1-2% of a disintegrant;
  (ii) about 0.1-2% of a glidant or adsorbant or absorbant; and
  (iii) about 0.1-2% of a lubricant.

In some embodiments, the lubricant is magnesium stearate.

In some embodiments, the diluent is lactose, mannitol, calcium phosphate dibasic, microcrystalline cellulose, starch, polyethylene oxide, or hydroxypropyl methylcellulose (HPMC). In some embodiments, the lactose is anhydrous, monohydrate, crystalline, or spray-dried. In some embodiments, the mannitol is spray dried or crystalline.

In some embodiments, the first diluent is lactose monohydrate. In some embodiments, the lactose monohydrate is engineered (e.g., spray-dried lactose monohydrate). In some embodiments, the lactose monohydrate is non-engineered (e.g., powder lactose monohydrate). In some embodiments, the lactose monohydrate is crystalline. In some embodiments, the first diluent is mannitol. In some embodiments, the mannitol is spray dried or crystalline. In some embodiments, the first diluent is calcium phosphate dibasic.

In some embodiments, a second diluent is microcrystalline cellulose. In some embodiments, a second diluent is starch, polyethylene oxide, or hydroxypropyl methylcellulose (HPMC).

In embodiments, a first diluent is lactose, and a second diluent is microcrystalline cellulose. In embodiments, a first diluent is lactose, and a second diluent is starch. In embodiments, a first diluent is lactose, and a second diluent is polyethylene oxide. In embodiments, a first diluent is lactose, and a second diluent is HPMC. In embodiments, a first diluent is lactose, and a second diluent is mannitol. In embodiments, a first diluent is lactose, and a second diluent is calcium phosphate dibasic.

In embodiments, a first diluent is lactose monohydrate, and a second diluent is microcrystalline cellulose. In embodiments, a first diluent is lactose monohydrate, and a second diluent is starch. In embodiments, a first diluent is lactose monohydrate, and a second diluent is polyethylene oxide. In embodiments, a first diluent is lactose monohydrate, and a second diluent is HPMC. In embodiments, a first diluent is lactose monohydrate, and a second diluent is mannitol. In embodiments, a first diluent is lactose monohydrate, and a second diluent is calcium phosphate dibasic.

In embodiments, a first diluent is mannitol, and a second diluent is lactose (e.g., lactose monohydrate). In embodiments, a first diluent is mannitol, and a second diluent is microcrystalline cellulose. In embodiments, a first diluent is mannitol, and a second diluent is starch. In embodiments, a first diluent is mannitol, and a second diluent is polyethylene oxide. In embodiments, a first diluent is mannitol, and a second diluent is HPMC. In embodiments, a first diluent is mannitol, and a second diluent is calcium phosphate dibasic.

In embodiments, a first diluent is calcium phosphate dibasic, and a second diluent is mannitol. In embodiments, a first diluent is calcium phosphate dibasic, and a second diluent is lactose (e.g., lactose monohydrate). In embodiments, a first diluent is calcium phosphate dibasic, and a second diluent is microcrystalline cellulose. In embodiments, a first diluent is calcium phosphate dibasic, and a second diluent is starch. In embodiments, a first diluent is calcium phosphate dibasic, and a second diluent is polyethylene oxide. In embodiments, a first diluent is calcium phosphate dibasic, and a second diluent is HPMC.

In embodiments, a first diluent is microcrystalline cellulose, and a second diluent is lactose (e.g., lactose monohydrate). In embodiments, a first diluent is microcrystalline cellulose, and a second diluent is mannitol. In embodiments, a first diluent is microcrystalline cellulose, and a second diluent is starch. In embodiments, a first diluent is microcrystalline cellulose, and a second diluent is polyethylene oxide. In embodiments, a first diluent is microcrystalline cellulose, and a second diluent is HPMC. In embodiments, a first diluent is microcrystalline cellulose, and a second diluent is calcium phosphate dibasic.

In embodiments, a first diluent is starch, and a second diluent is mannitol. In embodiments, a first diluent is starch, and a second diluent is lactose (e.g., lactose monohydrate). In embodiments, a first diluent is starch, and a second diluent is microcrystalline cellulose. In embodiments, a first diluent is starch, and a second diluent is polyethylene oxide. In embodiments, a first diluent is starch, and a second diluent is HPMC. In embodiments, a first diluent is starch, and a second diluent is calcium phosphate dibasic.

In embodiments, a first diluent is polyethylene oxide, and a second diluent is mannitol. In embodiments, a first diluent is polyethylene oxide, and a second diluent is lactose (e.g., lactose monohydrate). In embodiments, a first diluent is polyethylene oxide, and a second diluent is microcrystalline cellulose. In embodiments, a first diluent is polyethylene oxide, and a second diluent is starch. In embodiments, a first diluent is polyethylene oxide, and a second diluent is HPMC. In embodiments, a first diluent is polyethylene oxide, and a second diluent is calcium phosphate dibasic.

In embodiments, a first diluent is HPMC, and a second diluent is mannitol. In embodiments, a first diluent is HPMC, and a second diluent is lactose (e.g., lactose monohydrate). In embodiments, a first diluent is HPMC, and a second diluent is microcrystalline cellulose. In embodiments, a first diluent is HPMC, and a second diluent is polyethylene oxide. In embodiments, a first diluent is starch, and a second diluent is starch. In embodiments, a first diluent is HPMC, and a second diluent is calcium phosphate dibasic.

In some embodiments, the binder is povidone (PVP). In some embodiments, the binder is hydroxypropyl cellulose (HPC). In some embodiments, the binder is hydroxypropyl methylcellulose (HPMC).

In some embodiments, the disintegrant is crospovidone or croscarmellose. In some embodiments, the disintegrant is crospovidone. In some embodiments, the glidant is silicon dioxide. In some embodiments, the glidant is intermediate meso-porous silica. In some embodiments, the intermediate meso-porous silica comprises syloid FP-244.

In some embodiments, composition further comprises a disintegrant. In some embodiments, the disintegrant is crospovidone or croscarmellose. In some embodiments, the croscarmellose is croscarmellose sodium. In some embodiments, the composition further comprises a large meso-porous silica excipient as an adsorbant. In some embodiments, the large meso-porous silica excipient absorbs water. In some embodiments, the composition further comprises an intermediate meso-porous silica excipient as a glidant. In some embodiments, the intermediate meso-porous silica comprises syloid FP-244. In some embodiments, the composition further comprises an additional excipient as an adsorbant such as bentonite, talc, microcrystalline cellulose, charcoal, fumed silica, magnesium carbonate, or similar excipients.

In some embodiments, the composition further comprises silicon dioxide. In some embodiments, the silicon dioxide is present in an amount of about 0.1% to about 10% by weight. In some embodiments, the silicon dioxide is present in an amount of about 0.1% to about 5% by weight. In some embodiments, the silicon dioxide is present in an amount of about 0.1%, about 0.2%, about 0.3%, about 0.4%, about 0.5%, about 0.6, about 0.7%, about 0.8%, about 0.9%, about 1%, about 1.5%, about 2%, about 2.5%, about 3%, about 3.5%, about 4%, about 4.5%, or about 5% by weight.

In embodiments, a composition comprises a binder that is povidone (PVP). In embodiments, a composition further comprises a disintegrant. In embodiments, a disintegrant is crospovidone. In embodiments, a disintegrant is croscarmellose (e.g., croscarmellose sodium). In embodiments, a composition further comprises silicon dioxide. In embodiments, a composition does not comprise magnesium stearate. In embodiments, a composition further comprises magnesium stearate.

In embodiments, a composition comprises a binder that is hydroxypropyl cellulose (HPC). In embodiments, a composition further comprises a disintegrant. In embodiments, a disintegrant is crospovidone. In embodiments, a disintegrant is croscarmellose (e.g., croscarmellose sodium). In embodiments, a composition further comprises silicon dioxide. In embodiments, a composition does not comprise magnesium stearate. In embodiments, a composition further comprises magnesium stearate.

In embodiments, a composition comprises a binder that is hydroxypropyl methylcellulose (HPMC). In embodiments, a composition further comprises a disintegrant. In embodiments, a disintegrant is crospovidone. In embodiments, a disintegrant is croscarmellose (e.g., croscarmellose sodium). In embodiments, a composition further comprises silicon dioxide. In embodiments, a composition does not comprise magnesium stearate. In embodiments, a composition further comprises magnesium stearate.

In some embodiments, the composition further comprises an intragranular phase. In some embodiments, the intragranular phase comprises silicon dioxide. In some embodiments, the silicon dioxide in the intragranular phase is present in an amount of about 0.1% to about 10% by weight. In some embodiments, the silicon dioxide in the intragranular phase is present in an amount of about 0.1% to about 5% by weight. In some embodiments, the silicon dioxide in the intragranular phase is present in an amount of about 0.1%, about 0.2%, about 0.3%, about 0.4%, about 0.5%, about 0.6, about 0.7%, about 0.8%, about 0.9%, about 1%, about 1.5%, about 2%, about 2.5%, about 3%, about 3.5%, about 4%, about 4.5%, or about 5% by weight.

In some embodiments, wherein the intragranular phase does not comprise magnesium stearate. In some embodiments, the intragranular phase comprises niraparib, lactose monohydrate, microcrystalline cellulose, crospovidone, and povidone. In some embodiments, the intragranular phase comprises niraparib, lactose monohydrate, microcrystalline cellulose, croscarmellose, and hydroxypropyl cellulose (HPC). In some embodiments, the intragranular phase comprises niraparib, lactose monohydrate, microcrystalline cellulose, croscarmellose, and hydroxypropyl methylcellulose (HMPC). In some embodiments, the intragranular phase comprises niraparib, lactose monohydrate, microcrystalline cellulose, crospovidone, povidone, and a large meso-porous silica excipient as an adsorbant or absorbant or an intermediate meso-porous silica excipient as a glidant. In some embodiments, the intragranular phase comprises niraparib, lactose monohydrate, microcrystalline cellulose, crospovidone, povidone, and a large meso-porous silica excipient as an adsorbant or absorbant. In some embodiments, the intragranular phase comprises niraparib, lactose monohydrate, microcrystalline cellulose, crospovidone, povidone, and an intermediate meso-porous silica excipient as a glidant.

In some embodiments, the intragranular phase comprises magnesium stearate. In some embodiments, the intragranular phase comprises niraparib, microcrystalline cellulose, calcium phosphate dibasic, crospovidone, povidone, and magnesium stearate. In some embodiments, the intragranular phase comprises niraparib, microcrystalline cellulose, mannitol, croscarmellose, hydroxypropyl cellulose (HPC), and magnesium stearate. In some embodiments, the intragranular phase comprises niraparib, microcrystalline cellulose, mannitol, croscarmellose, hydroxypropyl methylcellulose (HPMC), and magnesium stearate. In some embodiments, the intragranular phase comprises niraparib, microcrystalline cellulose, mannitol, crospovidone, povidone, and magnesium stearate.

In some embodiments, the composition further comprises an extragranular phase. In some embodiments, the extragranular phase comprises magnesium stearate. In some embodiments, the extragranular phase comprises crospovidone. In some embodiments, the extragranular phase comprises croscarmellose.

In some embodiments, the extragranular phase comprises silicon dioxide. In some embodiments, the silicon dioxide in the extragranular phase is present in an amount of about 0.1% to about 10% by weight. In some embodiments, the silicon dioxide in the extragranular phase is present in an amount of about 0.1% to about 5% by weight. In some embodiments, the silicon dioxide in the extragranular phase is present in an amount of about 0.1% to about 2.5% by weight. In some embodiments, the silicon dioxide in the extragranular phase is present in an amount of about 0.1%, about 0.2%, about 0.3%, about 0.4%, about 0.5%, about 0.6, about 0.7%, about 0.8%, about 0.9%, about 1%, about 1.5%, about 2%, about 2.5%, about 3%, about 3.5%, about 4%, about 4.5%, or about 5% by weight.

In some embodiments, the niraparib is present in an amount of about 5-90% by weight. In some embodiments, the niraparib is present in an amount of about 5-80% by weight. In some embodiments, the niraparib is present in an amount of about 5-70% by weight. In some embodiments, the niraparib is present in an amount of about 5-60% by weight. In some embodiments, the niraparib is present in an amount of about 5-50% by weight. In some embodiments, the niraparib is present in an amount of about 5-40% by weight. In some embodiments, the niraparib is present in an amount of about 5-30% by weight. In some embodiments, the niraparib is present in an amount of about 5-20% by weight. In some embodiments, the niraparib is present in an amount of about 5-10% by weight. In some embodiments, the niraparib is present in an amount of about 10-90% by weight. In some embodiments, the niraparib is present in an amount of about 10-80% by weight. In some embodiments, the niraparib is present in an amount of about 10-70% by weight. In some embodiments, the niraparib is present in an amount of about 10-60% by weight. In some embodiments, the niraparib is present in an amount of about 10-50% by weight. In some embodiments, the niraparib is present in an amount of about 10-40% by weight. In some embodiments, the niraparib is present in an amount of about 10-30% by weight. In some embodiments, the niraparib is present in an amount of about 10-20% by weight. In some embodiments, the niraparib is present in an amount of about 20-90% by weight. In some embodiments, the niraparib is present in an amount of about 20-80% by weight. In some embodiments, the niraparib is present in an amount of about 20-70% by weight. In some embodiments, the niraparib is present in an amount of about 20-60% by weight. In some embodiments, the niraparib is present in an amount of about 20-50% by weight. In some embodiments, the niraparib is present in an amount of about 20-40% by weight. In some embodiments, the niraparib is present in an amount of about 20-30% by weight. In some embodiments, the niraparib is present in an amount of about 30-90% by weight. In some embodiments, the niraparib is present in an amount of about 30-80% by weight. In some embodiments, the niraparib is present in an amount of about 30-70% by weight. In some embodiments, the niraparib is present in an amount of about 30-60% by weight. In some embodiments, the niraparib is present in an amount of about 30-50% by weight. In some embodiments, the niraparib is present in an amount of about 30-40% by weight. In some embodiments, the niraparib is present in an amount of about 40-90% by weight. In some embodiments, the niraparib is present in an amount of about 40-80% by weight. In some embodiments, the niraparib is present in an amount of about 40-70% by weight. In some embodiments, the niraparib is present in an amount of about 40-60% by weight. In some embodiments, the niraparib is present in an amount of about 40-50% by weight. In some embodiments, the niraparib is present in an amount of about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 7'7%, about 78%, about 79%, about 80%, about 81%, about 82%, about 83%, about 84%, about 85%, about 86%, about 87%, about 88%, about 89%, or about 90% by weight. In some embodiments, the niraparib is the pharmaceutically acceptable salt of niraparib. In some embodiments, the niraparib is niraparib tosylate monohydrate.

In some embodiments, the second diluent (e.g., microcrystalline cellulose, starch, polyethylene oxide, and hydroxypropyl methylcellulose (HPMC)) is present in an amount of about 5-90% by weight. In some embodiments, the second diluent (e.g., microcrystalline cellulose, starch, polyethylene oxide, and hydroxypropyl methylcellulose (HPMC)) is present in an amount of about 5-80% by weight. In some embodiments, the second diluent (e.g., microcrystalline cellulose, starch, polyethylene oxide, and hydroxypropyl methylcellulose (HPMC)) is present in an amount of about 5-70% by weight. In some embodiments, the second diluent (e.g., microcrystalline cellulose, starch, polyethylene oxide, and hydroxypropyl methylcellulose (HPMC)) is present in an amount of about 5-60% by weight. In some embodiments, the second diluent (e.g., microcrystalline cellulose, starch, polyethylene oxide, and hydroxypropyl methylcellulose (HPMC)) is present in an amount of about 5-50% by weight. In some embodiments, the second diluent (e.g., microcrystalline cellulose, starch, polyethylene oxide, and hydroxypropyl methylcellulose (HPMC)) is present in an amount of about 5-40% by weight. In some embodiments, the second diluent (e.g., microcrystalline cellulose, starch, polyethylene oxide, and hydroxypropyl methylcellulose (HPMC)) is present in an amount of about 5-30% by weight. In some embodiments, the second diluent (e.g., microcrystalline cellulose, starch, polyethylene oxide, and hydroxypropyl methylcellulose (HPMC)) is present in an amount of about 5-20% by weight. In some embodiments, the second diluent (e.g., microcrystalline cellulose, starch, polyethylene oxide, and hydroxypropyl methylcellulose (HPMC)) is present in an amount of about 5-10% by weight. In some embodiments, the second diluent (e.g., microcrystalline cellulose, starch, polyethylene oxide, and hydroxypropyl methylcellulose (HPMC)) is present in an amount of about 10-90% by weight. In some embodiments, the second diluent (e.g., microcrystalline cellulose, starch, polyethylene oxide, and hydroxypropyl methylcellulose (HPMC)) is present in an amount of about 10-80% by weight. In some embodiments, the second diluent (e.g., microcrystalline cellulose, starch, polyethylene oxide, and hydroxypropyl methylcellulose (HPMC)) is present in an amount of about 10-70% by weight. In some embodiments, the second diluent (e.g., microcrystalline cellulose, starch, polyethylene oxide, and hydroxypropyl methylcellulose (HPMC)) is present in an amount of about 10-60% by weight. In some embodiments, the second diluent (e.g., microcrystalline cellulose, starch, polyethylene oxide, and hydroxypropyl methylcellulose (HPMC)) is present in an amount of about 10-50% by weight. In some embodiments, the second diluent (e.g., microcrystalline cellulose, starch, polyethylene oxide, and hydroxypropyl methylcellulose (HPMC)) is present in an amount of about 10-40% by weight. In some embodiments, the second diluent (e.g., microcrystalline cellulose, starch, polyethylene oxide, and hydroxypropyl methylcellulose (HPMC)) is present in an amount of about 10-30% by weight. In some embodiments, the second diluent (e.g., microcrystalline cellulose, starch, polyethylene oxide, and hydroxypropyl methylcellulose (HPMC)) is present in an amount of about 10-20% by weight. In some embodiments, the second diluent (e.g., microcrystalline cellulose, starch, polyethylene oxide, and hydroxypropyl methylcellulose (HPMC)) is present in an amount of about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90% by weight.

In some embodiments, the microcrystalline cellulose is present in an amount of about 5-90% by weight. In some embodiments, the microcrystalline cellulose is present in an amount of about 5-80% by weight. In some embodiments, the microcrystalline cellulose is present in an amount of about 5-70% by weight. In some embodiments, the microcrystalline cellulose is present in an amount of about 5-60% by weight. In some embodiments, the microcrystalline cellulose is present in an amount of about 5-50% by weight. In some embodiments, the microcrystalline cellulose is present in an amount of about 5-40% by weight. In some embodiments, the microcrystalline cellulose is present in an amount of about 5-30% by weight. In some embodiments, the microcrystalline cellulose is present in an amount of about 5-20% by weight. In some embodiments, the microcrystalline cellulose is present in an amount of about 5-10% by weight. In some embodiments, the microcrystalline cellulose is present in an amount of about 10-90% by weight. In some embodiments, the microcrystalline cellulose is present in an amount of about 10-80% by weight. In some embodiments, the microcrystalline cellulose is present in an amount of about 10-70% by weight. In some embodiments, the microcrystalline cellulose is present in an amount of about 10-60% by weight. In some embodiments, the microcrystalline cellulose is present in an amount of about 10-50% by weight. In some embodiments, the microcrystalline cellulose is present in an amount of about 10-40% by weight. In some embodiments, the microcrystalline cellulose is present in an amount of about 10-30% by weight. In some embodiments, the microcrystalline cellulose is present in an amount of about 10-20% by weight. In some embodiments, the microcrystalline cellulose is present in an amount of about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90% by weight.

In some embodiments, the first diluent, such as lactose monohydrate, lactose anhydrous, mannitol, and calcium phosphate dibasic, is present in an amount of about 5-90% by weight. In some embodiments, the first diluent, such as lactose monohydrate, lactose anhydrous, mannitol, and calcium phosphate dibasic, is present in an amount of about 5-80% by weight. In some embodiments, the first diluent, such as lactose monohydrate, lactose anhydrous, mannitol, and calcium phosphate dibasic, is present in an amount of about 5-70% by weight. In some embodiments, the first diluent, such as lactose monohydrate, lactose anhydrous, mannitol, and calcium phosphate dibasic, is present in an amount of about 5-60% by weight. In some embodiments, the first diluent, such as lactose monohydrate, lactose anhydrous, mannitol, and calcium phosphate dibasic, is present in an amount of about 5-50% by weight. In some embodiments, the first diluent, such as lactose monohydrate, lactose anhydrous, mannitol, and calcium phosphate dibasic, is present in an amount of about 5-40% by weight. In some embodiments, the first diluent, such as lactose monohydrate, lactose anhydrous, mannitol, and calcium phosphate dibasic, is present in an amount of about 5-30% by weight. In some embodiments, the first diluent, such as lactose monohydrate, lactose anhydrous, mannitol, and calcium phosphate dibasic, is present in an amount of about 5-20% by weight. In some embodiments, the first diluent, such as lactose monohydrate, lactose anhydrous, mannitol, and calcium phosphate dibasic, is present in an amount of about 5-10% by weight. In some embodiments, the first diluent, such as lactose monohydrate, lactose anhydrous, mannitol, and calcium phosphate dibasic, is present in an amount of about 10-90% by weight. In some embodiments, the first diluent, such as lactose monohydrate, lactose anhydrous, mannitol, and calcium phosphate dibasic, is present in an amount of about 10-80% by weight. In some embodiments, the first diluent, such as lactose monohydrate, lactose anhydrous, mannitol, and calcium phosphate dibasic, is present in an amount of about 10-70% by weight. In some embodiments, the first diluent, such as lactose monohydrate, lactose anhydrous, mannitol, and calcium phosphate dibasic, is present in an amount of about 10-60% by weight. In some embodiments, the first diluent, such as lactose monohydrate, lactose anhydrous, mannitol, and calcium phosphate dibasic, is present in an amount of about 10-50% by weight. In some embodiments, the first diluent, such as lactose monohydrate, lactose anhydrous, mannitol, and calcium phosphate dibasic, is present in an amount of about 10-40% by weight. In some embodiments, the first diluent, such as lactose monohydrate, lactose anhydrous, mannitol, and calcium phosphate dibasic is present in an amount of about 10-30% by weight. In some embodiments, the first diluent, such as lactose monohydrate, lactose anhydrous, mannitol, and calcium phosphate dibasic is present in an amount of about 10-20% by weight. In some embodiments, the first diluent, such as lactose monohydrate, lactose anhydrous, mannitol, and calcium phosphate dibasic, is present in an amount of about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90% by weight.

In some embodiments, the diluent, such as lactose, mannitol, calcium phosphate dibasic, microcrystalline cellulose, starch, polyethylene oxide, or hydroxypropyl methylcellulose (HPMC), is present in an amount of about 5-90% by weight. In some embodiments, the lactose is anhydrous, monohydrate, crystalline, or spray-dried. In some embodiments, the mannitol is spray dried or crystalline. In some embodiments, the diluent, such as lactose, mannitol, calcium phosphate dibasic, microcrystalline cellulose, starch, polyethylene oxide, or hydroxypropyl methylcellulose (HPMC), is present in an amount of about 5-80% by weight. In some embodiments, the diluent, such as lactose, mannitol, calcium phosphate dibasic, microcrystalline cellulose, starch, polyethylene oxide, or hydroxypropyl methylcellulose (HPMC), is present in an amount of about 5-70% by weight. In some embodiments, the diluent, such as lactose, mannitol, calcium phosphate dibasic, microcrystalline cellulose, starch, polyethylene oxide, or hydroxypropyl methylcellulose (HPMC), is present in an amount of about 5-60% by weight. In some embodiments, the diluent, such as lactose, mannitol, calcium phosphate dibasic, microcrystalline cellulose, starch, polyethylene oxide, or hydroxypropyl methylcellulose (HPMC), is present in an amount of about 5-50% by weight. In some embodiments, the diluent, such as lactose, mannitol, calcium phosphate dibasic, microcrystalline cellulose, starch, polyethylene oxide, or hydroxypropyl methylcellulose (HPMC), is present in an amount of about 5-40% by weight. In some embodiments, the diluent, such as lactose, mannitol, calcium phosphate dibasic, microcrystalline cellulose, starch, polyethylene oxide, or hydroxypropyl methylcellulose (HPMC), is present in an amount of about 5-30% by weight. In some embodiments, the diluent, such as lactose, mannitol, calcium phosphate dibasic, microcrystalline cellulose, starch, polyethylene oxide, or hydroxypropyl methylcellulose (HPMC), is present in an amount of about 5-20% by weight. In some embodiments, the diluent, such as lactose, mannitol, calcium phosphate dibasic, microcrystalline cellulose, starch, polyethylene oxide, or hydroxypropyl methylcellulose (HPMC), is present in an amount of about 5-10% by weight. In some embodiments, the diluent, such as lactose, mannitol, calcium phosphate dibasic, microcrystalline cellulose, starch, polyethylene oxide, or hydroxypropyl methylcellulose (HPMC), is present in an amount of about 10-90% by weight. In some embodiments, the diluent, such as lactose, mannitol, calcium phosphate dibasic, microcrystalline cellulose, starch, polyethylene oxide, or hydroxypropyl methylcellulose (HPMC), is present in an amount of about 10-80% by weight. In some embodiments, the diluent, such as lactose, mannitol, calcium phosphate dibasic, microcrystalline cellulose, starch, polyethylene oxide, or hydroxypropyl methylcellulose (HPMC), is present in an amount of about 10-70% by weight. In some embodiments, the diluent, such as lactose, mannitol, calcium phosphate dibasic, microcrystalline cellulose, starch, polyethylene oxide, or hydroxypropyl methylcellulose (HPMC), is present in an amount of about 10-60% by weight. In some embodiments, the diluent, such as lactose, mannitol, calcium phosphate dibasic, microcrystalline cellulose, starch, polyethylene oxide, or hydroxypropyl methylcellulose (HPMC), is present in an amount of about 10-50% by weight. In some embodiments, the diluent, such as lactose, mannitol, calcium phosphate dibasic, microcrystalline cellulose, starch, polyethylene oxide, or hydroxypropyl methylcellulose (HPMC), is present in an amount of about 10-40% by weight. In some embodiments, the diluent, such as lactose, mannitol, calcium phosphate dibasic, microcrystalline cellulose, starch, polyethylene oxide, or hydroxypropyl methylcellulose (HPMC), is present in an amount of about 10-30% by weight. In some embodiments, the diluent, such as lactose, mannitol, calcium phosphate dibasic, microcrystalline cellulose, starch, polyethylene oxide, or hydroxypropyl methylcellulose (HPMC), is present in an amount of about 10-20% by weight. In some embodiments, the diluent, such as lactose, mannitol, calcium phosphate dibasic, microcrystalline cellulose, starch, polyethylene oxide, or hydroxypropyl methylcellulose (HPMC), is present in an amount of about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90% by weight.

In some embodiments, the lactose is present in an amount of about 5-90% by weight. In some embodiments, lactose is present in an amount of about 5-80% by weight. In some embodiments, lactose is present in an amount of about 5-70% by weight. In some embodiments, lactose is present in an amount of about 5-60% by weight. In some embodiments, lactose is present in an amount of about 5-50% by weight. In some embodiments, lactose is present in an amount of about 5-40% by weight. In some embodiments, lactose is present in an amount of about 5-30% by weight. In some embodiments, lactose is present in an amount of about 5-20% by weight. In some embodiments, lactose is present in an amount of about 5-10% by weight. In some embodiments, lactose is present in an amount of about 10-90% by weight. In some embodiments, lactose is present in an amount of about 10-80% by weight. In some embodiments, lactose is present in an amount of about 10-70% by weight. In some embodiments, lactose is present in an amount of about 10-60% by weight. In some embodiments, lactose is present in an amount of about 10-50% by weight. In some embodiments, lactose is present in an amount of about 10-40% by weight. In some embodiments, lactose is present in an amount of about 10-30% by weight. In some embodiments, lactose is present in an amount of about 10-20% by weight. In some embodiments, lactose is present in an amount of about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90% by weight.

In some embodiments, lactose monohydrate is present in an amount of about 5-90% by weight. In some embodiments, lactose monohydrate is present in an amount of about 5-80% by weight. In some embodiments, lactose monohydrate is present in an amount of about 5-70% by weight. In some embodiments, lactose monohydrate is present in an amount of about 5-60% by weight. In some embodiments, lactose monohydrate is present in an amount of about 5-50% by weight. In some embodiments, lactose monohydrate is present in an amount of about 5-40% by weight. In some embodiments, lactose monohydrate is present in an amount of about 5-30% by weight. In some embodiments, the lactose monohydrate is present in an amount of about 5-20% by weight. In some embodiments, lactose monohydrate is present in an amount of about 5-10% by weight. In some embodiments, lactose monohydrate is present in an amount of about 10-90% by weight. In some embodiments, lactose monohydrate is present in an amount of about 10-80% by weight. In some embodiments, lactose monohydrate is present in an amount of about 10-70% by weight. In some embodiments, lactose monohydrate is present in an amount of about 10-60% by weight. In some embodiments, lactose monohydrate is present in an amount of about 10-50% by weight. In some embodiments, lactose monohydrate is present in an amount of about 10-40% by weight. In some embodiments, lactose monohydrate is present in an amount of about 10-30% by weight. In some embodiments, lactose monohydrate is present in an amount of about 10-20% by weight. In some embodiments, lactose monohydrate is present in an amount of about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 3'7%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90% by weight.

In some embodiments, the binder, such as povidone, hydroxylpropyl cellulose, or hydroxypropyl methylcellulose, is present in an amount of about 1-40% by weight. In some embodiments, the binder, such as povidone, hydroxylpropyl cellulose, or hydroxypropyl methylcellulose, is present in an amount of about 1-30% by weight. In some embodiments, the binder, such as povidone, hydroxylpropyl cellulose, or hydroxypropyl methylcellulose, is present in an amount of about 1-20% by weight. In some embodiments, the binder, such as povidone, hydroxylpropyl cellulose, or hydroxypropyl methylcellulose, is present in an amount of about 1-10% by weight. In some embodiments, the binder, such as povidone, hydroxylpropyl cellulose, or hydroxypropyl methylcellulose, is present in an amount of about 1-5% by weight. In some embodiments, the binder, such as povidone, hydroxylpropyl cellulose, or hydroxypropyl methylcellulose, is present in an amount of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 3'7%, about 38%, about 39%, or about 40% by weight.

In some embodiments, povidone is present in an amount of about 5-90% by weight. In some embodiments, povidone is present in an amount of about 5-80% by weight. In some embodiments, povidone is present in an amount of about 5-70% by weight. In some embodiments, povidone is present in an amount of about 5-60% by weight. In some embodiments, povidone is present in an amount of about 5-50% by weight. In some embodiments, povidone is present in an amount of about 5-40% by weight. In some embodiments, povidone is present in an amount of about 5-30% by weight. In some embodiments, povidone is present in an amount of about 5-20% by weight. In some embodiments, povidone is present in an amount of about 5-10% by weight. In some embodiments, povidone is present in an amount of about 10-90% by weight. In some embodiments, povidone is present in an amount of about 10-80% by weight. In some embodiments, povidone is present in an amount of about 10-70% by weight. In some embodiments, povidone is present in an amount of about 10-60% by weight. In some embodiments, povidone is present in an amount of about 10-50% by weight. In some embodiments, povidone is present in an amount of about 10-40% by weight. In some embodiments, povidone is present in an amount of about 10-30% by weight. In some embodiments, povidone is present in an amount of about 10-20% by weight. In some embodiments, povidone is present in an amount of about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90% by weight.

In some embodiments, the disintegrant, such as crospovidone or croscarmellose, is present in an amount of about 0.1-40% by weight. In some embodiments, the disintegrant, such as crospovidone or croscarmellose, is present in an amount of about 0.1-30% by weight. In some embodiments, the disintegrant, such as crospovidone and croscarmellose, is present in an amount of about 0.1-20% by weight. In some embodiments, the disintegrant, such as crospovidone or croscarmellose, is present in an amount of about 0.1-10% by weight. In some embodiments, the disintegrant, such as crospovidone and croscarmellose, is present in an amount of about 0.1-5% by weight. In some embodiments, the disintegrant, such as crospovidone or croscarmellose, is present in an amount of about 0.1%, about 0.2%, about 0.3%, about 0.4%, about 0.5%, about 0.6, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 3'7%, about 38%, about 39%, or about 40% by weight.

In some embodiments, the crospovidone is present in an amount of about 0.1-40% by weight. In some embodiments, the crospovidone is present in an amount of about 0.1-30% by weight. In some embodiments, the crospovidone is present in an amount of about 0.1-20% by weight. In some embodiments, the crospovidone is present in an amount of about 0.1-10% by weight. In some embodiments, the crospovidone is present in an amount of about 0.1-5% by weight. In some embodiments, the crospovidone is present in an amount of about 0.1%, about 0.2%, about 0.3%, about 0.4%, about 0.5%, about 0.6, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 3'7%, about 38%, about 39%, or about 40% by weight.

In some embodiments, the croscarmellose is present in an amount of about 0.1-40% by weight. In some embodiments, the croscarmellose is present in an amount of about 0.1-30% by weight. In some embodiments, the croscarmellose is present in an amount of about 0.1-20% by weight. In some embodiments, the croscarmellose is present in an amount of about 0.1-10% by weight. In some embodiments, the croscarmellose is present in an amount of about 0.1-5% by weight. In some embodiments, the croscarmellose is present in an amount of about 0.1%, about 0.2%, about 0.3%, about 0.4%, about 0.5%, about 0.6, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, or about 40% by weight. In some embodiments, the croscarmellose is croscarmellose sodium.

In some embodiments, the glidant, such as silicon dioxide, is present in an amount of about 0.1-40% by weight. In some embodiments, the glidant, such as silicon dioxide, is present in an amount of about 0.1-30% by weight. In some embodiments, the glidant, such as silicon dioxide, is present in an amount of about 0.1-20% by weight. In some embodiments, the glidant, such as silicon dioxide, is present in an amount of about 0.1-10% by weight. In some embodiments, the glidant, such as silicon dioxide, is present in an amount of about 0.1-5% by weight. In some embodiments, the glidant, such as silicon dioxide, is present in an amount of about 0.1%, about 0.2%, about 0.3%, about 0.4%, about 0.5%, about 0.6, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, or about 40% by weight.

In some embodiments, the silicon dioxide, is present in an amount of about 0.1-40% by weight. In some embodiments, the silicon dioxide is present in an amount of about 0.1-30% by weight. In some embodiments, the silicon dioxide is present in an amount of about 0.1-20% by weight. In some embodiments, the silicon dioxide is present in an amount of about 0.1-10% by weight. In some embodiments, the silicon dioxide is present in an amount of about 0.1-5% by weight. In some embodiments, the silicon dioxide is present in an amount of about 0.1%, about 0.2%, about 0.3%, about 0.4%, about 0.5%, about 0.6, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, or about 40% by weight.

In some embodiments, the lubricant, such as magnesium stearate, in the intragranular phase or extragranular phase is present in an amount of about 0.1-40% by weight. In some embodiments, the lubricant, such as magnesium stearate, in the intragranular phase or extragranular phase is present in an amount of about 0.1-30% by weight. In some embodiments, the lubricant, such as magnesium stearate, in the intragranular phase or extragranular phase is present in an amount of about 0.1-20% by weight. In some embodiments, the lubricant, such as magnesium stearate, in the intragranular phase or extragranular phase is present in an amount of about 0.1-10% by weight. In some embodiments, the lubricant, such as magnesium stearate, in the intragranular phase or extragranular phase is present in an amount of about 0.1-5% by weight. In some embodiments, the lubricant, such as magnesium stearate, in the intragranular phase or extragranular phase is present in an amount of about 0.1-2.5% by weight. In some embodiments, the lubricant, such as magnesium stearate, in the intragranular phase or extragranular phase is present in an amount of about 0.1%, about 0.2%, about 0.3%, about 0.4%, about 0.5%, about 0.6, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 3'7%, about 38%, about 39%, or about 40% by weight.

In some embodiments, the magnesium stearate in the intragranular phase is present in an amount of about 0.1-40% by weight. In some embodiments, the magnesium stearate in the intragranular phase is present in an amount of about 0.1-30% by weight. In some embodiments, magnesium stearate in the intragranular phase is present in an amount of about 0.1-20% by weight. In some embodiments, magnesium stearate in the intragranular phase is present in an amount of about 0.1-10% by weight. In some embodiments, the magnesium stearate in the intragranular phase is present in an amount of about 0.1-5% by weight. In some embodiments, the magnesium stearate in the intragranular phase is present in an amount of about 0.1-2.5% by weight. In some embodiments, the magnesium stearate in the intragranular phase is present in an amount of about 0.1%, about 0.2%, about 0.3%, about 0.4%, about 0.5%, about 0.6, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 3'7%, about 38%, about 39%, or about 40% by weight.

In some embodiments, the magnesium stearate in the extragranular phase is present in an amount of about 0.1-40% by weight. In some embodiments, the magnesium stearate in the extragranular phase is present in an amount of about 0.1-30% by weight. In some embodiments, magnesium stearate in the extragranular phase is present in an amount of about 0.1-20% by weight. In some embodiments, magnesium stearate in the extragranular phase is present in an amount of about 0.1-10% by weight. In some embodiments, the magnesium stearate in the extragranular phase is present in an amount of about 0.1-5% by weight. In some embodiments, the magnesium stearate in the extragranular phase is present in an amount of about 0.1-2.5% by weight. In some embodiments, the magnesium stearate in the extragranular phase is present in an amount of about 0.1%, about 0.2%, about 0.3%, about 0.4%, about 0.5%, about 0.6, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 3'7%, about 38%, about 39%, or about 40% by weight.

Also provided in another aspect is a tablet composition comprising a) an effective amount of niraparib to inhibit polyadenosine diphosphate ribose polymerase (PARP) when administered to a subject in need thereof; and b) silicon dioxide; wherein the effective amount of niraparib is from about 50 mg to about 350 mg based on the niraparib free base.

In some embodiments, the effective amount of niraparib is from about 75 mg to about 125 mg based on the niraparib free base. In some embodiments, the effective amount of niraparib is about 50 mg, about 100 mg, or about 150 mg based on the niraparib free base. In some embodiments, the effective amount of niraparib is about 100 mg based on the niraparib free base. In some embodiments, the effective amount of niraparib is from about 175 mg to about 225 mg based on the niraparib free base. In some embodiments, the effective amount of niraparib is about 150 mg, about 200 mg, or about 250 mg based on the niraparib free base. In some embodiments, the effective amount of niraparib is about 200 mg based on the niraparib free base. In some embodiments, the effective amount of niraparib is from about 275 mg to about 325 mg based on the niraparib free base. In some embodiments, the effective amount of niraparib is about 250 mg, about 300 mg, or about 350 mg based on the niraparib free base. In some embodiments, the effective amount of niraparib is about 300 mg based on the niraparib free base. In some embodiments, the niraparib comprises niraparib free base or a pharmaceutically acceptable salt thereof. In some embodiments, the pharmaceutically acceptable salt of niraparib is niraparib tosylate.

In some embodiments, silicon dioxide provides improved flow properties. In some embodiments, silicon dioxide improves tensile strength, hardness, and/or bonding of intragranular materials. In some embodiments, silicon dioxide improves the properties of the composition comprising niraparib that is directly compressed to form the tablet, such as reducing the adherence or stickiness of the composition.

In some embodiments, the silicon dioxide is present in the intragranular phase. In some embodiments, the silicon dioxide in the intragranular phase is present in an amount of about 0.1-40% by weight. In some embodiments, the silicon dioxide in the intragranular phase is present in an amount of about 0.1-30% by weight. In some embodiments, silicon dioxide in the intragranular phase is present in an amount of about 0.1-20% by weight. In some embodiments, silicon dioxide in the intragranular phase is present in an amount of about 0.1-10% by weight. In some embodiments, the silicon dioxide in the intragranular phase is present in an amount of about 0.1-5% by weight. In some embodiments, the silicon dioxide in the intragranular phase is present in an amount of about 0.1-2.5% by weight. In some embodiments, the silicon dioxide in the intragranular phase is present in an amount of about 0.1%, about 0.2%, about 0.3%, about 0.4%, about 0.5%, about 0.6, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, or about 40% by weight.

In some embodiments, the silicon dioxide is present in the extragranular phase. In some embodiments, the silicon dioxide in the extragranular phase is present in an amount of about 0.1-40% by weight. In some embodiments, the silicon dioxide in the extragranular phase is present in an amount of about 0.1-30% by weight. In some embodiments, silicon dioxide in the extragranular phase is present in an amount of about 0.1-20% by weight. In some embodiments, silicon dioxide in the extragranular phase is present in an amount of about 0.1-10% by weight. In some embodiments, the silicon dioxide in the extragranular phase is present in an amount of about 0.1-5% by weight. In some embodiments, the silicon dioxide in the extragranular phase is present in an amount of about 0.1-2.5% by weight. In some embodiments, the silicon dioxide in the extragranular phase is present in an amount of about 0.1%, about 0.2%, about 0.3%, about 0.4%, about 0.5%, about 0.6, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, or about 40% by weight.

Intragranular Phase/Extragranular Phase Distribution

In some embodiments, the distribution of the intragranular phase components and extragranular phase components provide desirable disintegration profiles. In another aspect, provided herein is a tablet composition comprising: an effective amount of niraparib to inhibit polyadenosine diphosphate ribose polymerase (PARP) when administered to a subject in need thereof; wherein the tablet further comprises an intragranular phase and an extragranular phase; and the tablet has at least one of the following: a) the amount of components used to form the intragranular phase is about 50% to about 98% by weight of the tablet composition; and b) the amount of components used to form the extragranular phase is about 2% to about 50% by weight of the tablet composition.

In some embodiments, the amount of components used to form the intragranular phase is about 50% to about 98% by weight of the tablet composition. In some embodiments, the amount of components used to form the intragranular phase is about 55% to about 98% by weight of the tablet composition. In some embodiments, the amount of components used to form the intragranular phase is about 60% to about 98% by weight of the tablet composition. In some embodiments, the amount of components used to form the intragranular phase is about 65% to about 98% by weight of the tablet composition. In some embodiments, the amount of components used to form the intragranular phase is about 70% to about 98% by weight of the tablet composition. In some embodiments, the amount of components used to form the intragranular phase is about 75% to about 98% by weight of the tablet composition. In some embodiments, the amount of components used to form the intragranular phase is about 80% to about 98% by weight of the tablet composition. In some embodiments, the amount of components used to form the intragranular phase is about 85% to about 98% by weight of the tablet composition. In some embodiments, the amount of components used to form the intragranular phase is about 90% to about 98% by weight of the tablet composition. In some embodiments, the amount of components used to form the intragranular phase is about 92.5% to about 97.5% by weight of the tablet composition. In some embodiments, the amount of components used to form the intragranular phase is about 95% by weight of the tablet composition. In some embodiments, the amount of components used to form the intragranular phase is about 50%, about 55%, about 60%, about 65%, about 70%, about 75%, about 80%, about 85%, about 90%, about 91%, about 92%, about 93%, about 94%, about 95%, about 96%, about 97%, or about 98% by weight of the tablet composition.

In some embodiments, the amount of components used to form the extragranular phase is about 2% to about 50% by weight of the tablet composition. In some embodiments, the amount of components used to form the extragranular phase is about 2% to about 45% by weight of the tablet composition. In some embodiments, the amount of components used to form the extragranular phase is about 2% to about 40% by weight of the tablet composition. In some embodiments, the amount of components used to form the extragranular phase is about 2% to about 35% by weight of the tablet composition. In some embodiments, the amount of components used to form the extragranular phase is about 2% to about 30% by weight of the tablet composition. In some embodiments, the amount of components used to form the extragranular phase is about 2% to about 25% by weight of the tablet composition. In some embodiments, the amount of components used to form the extragranular phase is about 2% to about 20% by weight of the tablet composition. In some embodiments, the amount of components used to form the extragranular phase is about 2% to about 15% by weight of the tablet composition. In some embodiments, the amount of components used to form the extragranular phase is about 2% to about 10% by weight of the tablet composition. In some embodiments, the amount of components used to form the extragranular phase is about 2% to about 5% by weight of the tablet composition. In some embodiments, the amount of components used to form the extragranular phase is about 2.5% to about 7.5% by weight of the tablet composition. In some embodiments, the amount of components used to form the extragranular phase is about 5% by weight of the tablet composition. In some embodiments, the amount of components used to form the extragranular phase is about 2%, about 2.5%, about 3%, about 3.5%, about 4%, about 4.5%, about 5%, about 5.5%, about 6.0%, about 6.5%, about 7.0%, about 7.5%, about 8.0%, about 8.5%, about 9.0%, about 9.5%, about 10.0%, about 15%, about 20%, about 25%, about 30%, about 35%, about 40%, about 45%, or about 50% by weight of the tablet composition.

Pharmacodynamics

Niraparib inhibits PARP-1 and PARP-2 enzymes in vitro with $IC_{50}$ of 3.8 nM (0.82 ng/mL) and 2.1 nM (0.67 ng/mL), respectively. Niraparib inhibits intracellular PARP activity, with an $IC_{50}$ of 4 nM (1.28 mg/mL) and an $IC_{90}$ of 50 nM (16 ng/mL). A single dose of 50 mg/kg niraparib in tumor models resulted in >90% PARP inhibition and with daily dosing, tumor regression. At a dose of 50 mg/kg, tumor concentrations of ~4567 ng/mL were achieved at 6 hours, which exceeds the PARP $IC_{90}$ and resulted in tumor regression. In this same model, a dose of 75 mg/kg niraparib did not result in tumor regression; tumor regression was achieved when dosing was switched to a 50 mg/kg dose of niraparib.

As used herein, fasted human pharmacokinetic studies include both single dose, fasted, human pharmacokinetic studies and multiple dose, fasted, human pharmacokinetic studies. Multiple dose, fasted, human pharmacokinetic studies are performed in accordance to the FDA Guidance documents and/or analogous EMEA Guidelines. Pharmacokinetic parameters for steady state values may be determined directly from multiple dose, fasted, human pharmacokinetic studies or may be conveniently determined by extrapolation of single dose data using standard methods or industry standard software such as WinNonlin version 5.3 or higher.

In some embodiments, a once daily oral administration of a niraparib composition described herein to a human subject provides a mean peak plasma concentration ($C_{max}$) of 600 ng/mL to 1000 ng/mL. For example, a once daily oral administration of a niraparib composition described herein to a human subject can provide a mean peak plasma concentration ($C_{max}$) of 600 ng/mL, 625 ng/mL, 650 ng/mL, 675 ng/mL, 700 ng/mL, 725 ng/mL, 750 ng/mL, 775 ng/mL, 800 ng/mL, 825 ng/mL, 850 ng/mL, 875 ng/mL, 900 ng/mL, 925 ng/mL, 950 ng/mL, 975 ng/mL or 1000 ng/mL. For example, a once daily oral administration of a niraparib composition described herein to a human subject can provide a mean peak plasma concentration ($C_{max}$) of 804 ng/mL.

In some embodiments, a once daily oral administration of a niraparib composition described herein to a human subject provides a mean peak plasma concentration ($C_{max}$) in 0.5 to 6 hours. For example, a once daily oral administration of a niraparib composition described herein to a human subject can provide a mean peak plasma concentration ($C_{max}$) in about 0.5, 0.75, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, or 6 hours.

In some embodiments, the $C_{max}$ of a tablet comprising niraparib is about 50% to about 150% compared to the $C_{max}$ of a capsule comprising an equivalent amount of niraparib. In some embodiments, the $C_{max}$ of a tablet comprising niraparib is about 60% to about 140% compared to the $C_{max}$ of a capsule comprising niraparib. In some embodiments, the $C_{max}$ of a tablet comprising niraparib is about 70% to about 130% compared to the $C_{max}$ of a capsule comprising niraparib. In some embodiments, the $C_{max}$ of a tablet comprising niraparib is about 80% to about 120% compared to the $C_{max}$ of a capsule comprising niraparib. In some embodiments, the $C_{max}$ of a tablet comprising niraparib is about 80% compared to the $C_{max}$ of a capsule comprising niraparib. In some embodiments, the $C_{max}$ of a tablet comprising niraparib is about 80%, about 85%, about 90%, about 95%, about 100%, about 105%, about 110%, about 115%, about 120%, about 125%, or about 130% compared to the $C_{max}$ of a capsule comprising niraparib. In some embodiments, the $C_{max}$ of a tablet comprising niraparib is about 80%, about 85%, about 90%, about 95%, about 100%, or about 105% compared to the $C_{max}$ of a capsule comprising niraparib. In some embodiments, the $C_{max}$ of a tablet comprising niraparib is about 85%, or about 105% compared to the $C_{max}$ of a capsule comprising niraparib.

In some embodiments, the $AUC_{0-t}$ of a tablet comprising niraparib is about 50% to about 150% compared to the $AUC_{0-t}$ of a capsule comprising an equivalent amount of niraparib. In some embodiments, the $AUC_{0-t}$ of a tablet comprising niraparib is about 60% to about 140% compared to the $AUC_{0-t}$ of a capsule comprising niraparib. In some embodiments, the $AUC_{0-t}$ of a tablet comprising niraparib is about 70% to about 130% compared to the $AUC_{0-t}$ of a capsule comprising niraparib. In some embodiments, the $AUC_{0-t}$ of a tablet comprising niraparib is about 80% to about 120% compared to the $AUC_{0-t}$ of a capsule comprising niraparib. In some embodiments, the $AUC_{0-t}$ of a tablet comprising niraparib is about 80% compared to the $AUC_{0-t}$ of a capsule comprising niraparib. In some embodiments, the $AUC_{0-t}$ of a tablet comprising niraparib is about 80%, about 85%, about 90%, about 95%, about 100%, about 105%, about 110%, about 115%, about 120%, about 125%, or about 130% compared to the $C_{max}$ of a capsule comprising niraparib. In some embodiments, the $AUC_{0-t}$ of a tablet comprising niraparib is about 80%, about 85%, about 90%, about 95%, about 100%, or about 105% compared to the $AUC_{0-t}$ of a capsule comprising niraparib. In some embodiments, the $AUC_{0-t}$ of a tablet comprising niraparib is about 85%, or about 105% compared to the $AUC_{0-t}$ of a capsule comprising niraparib.

In some embodiments, the $AUC_{0-Infinity}$ of a tablet comprising niraparib is about 50% to about 150% compared to the $AUC_{0-Infinity}$ of a capsule comprising an equivalent amount of niraparib. In some embodiments, the $AUC_{0-Infinity}$ of a tablet comprising niraparib is about 60% to about 140% compared to the $AUC_{0-Infinity\ t}$ of a capsule comprising niraparib. In some embodiments, the $AUC_{0-infinity}$ of a tablet comprising niraparib is about 70% to about 130% compared to the $AUC_{0-Infinity}$ of a capsule comprising niraparib. In some embodiments, the $AUC_{0-Infinity}$ of a tablet comprising niraparib is about 80% to about 120% compared to the $AUC_{0-Infinity}$ of a capsule comprising niraparib. In some embodiments, the $AUC_{0-Infinity}$ of a tablet comprising niraparib is about 80% compared to the $AUC_{0-Infinity}$ of a capsule comprising niraparib. In some embodiments, the $AUC_{0-Infinity}$ of a tablet comprising niraparib is about 80%, about 85%, about 90%, about 95%, about 100%, about 105%, about 110%, about 115%, about 120%, about 125%, or about 130% compared to the $AUC_{0-Infinity}$ of a capsule comprising niraparib. In some embodiments, the $AUC_{0-Infinity}$ of a tablet comprising niraparib is about 80%, about 85%, about 90%, about 95%, about 100%, or about 105% compared to the $AUC_{0-Infinity}$ of a capsule comprising niraparib. In some embodiments, the $AUC_{0-Infinity}$ of a tablet comprising niraparib is about 85%, or about 105% compared to the $AUC_{0-Infinity}$ of a capsule comprising niraparib.

In some embodiments, an absolute bioavailability of niraparib provided in a composition described herein is about 60-90%. For example, an absolute bioavailability of niraparib provided in a composition described herein can be about 60%, 65%, 70%, 75%, 80%, 85% or 90%. For example, an absolute bioavailability of niraparib provided in a composition described herein can be about 73%.

In some embodiments, concomitant administration of a high fat meal does not significantly affect the pharmacokinetics of a niraparib composition described herein after administration of a dose described herein. For example, concomitant administration of a high fat meal may not significantly affect the pharmacokinetics of a niraparib composition described herein after administration of a 50 mg, 100 mg, 150 mg, 200 mg, 250 mg, 300 mg, 350 mg or 400 mg dose of niraparib.

In some embodiments, niraparib is moderately protein bound to human plasma after administration to a human subject. For example, after administration to a human subject about 60%, 65%, 70%, 75%, 80%, 85% or 90% of the niraparib is protein bound to human plasma. For example, after administration to a human subject about 83% of the niraparib is protein bound to human plasma.

In some embodiments, an apparent volume of distribution (Vd/F) of niraparib is from about 500 L to about 2000 L after administration to a human subject. For example, an apparent volume of distribution (Vd/F) of niraparib can be about 500 L, 550 L, 600 L, 650 L, 700 L, 750 L, 800 L, 850 L, 900 L, 950 L, 1000 L, 1100 L, 1200 L, 1300 L, 1350 L, 1400 L, 1450 L, 1500 L, 1600 L, 1700 L, 1800 L, 1900 L or 2000 L after administration to a human subject. For example, an apparent volume of distribution (Vd/F) of niraparib can be about 1220 L after administration to a human subject. For example, an apparent volume of distribution (Vd/F) of niraparib can be about 1074 L after administration to a human subject with cancer.

In some embodiments, following administration of niraparib provided in a composition described herein, the mean terminal half-life ($t_{1/2}$) of niraparib is from about 40 to 60 hours. For example, following administration of niraparib provided in a composition described herein, the mean terminal half-life ($t_{1/2}$) of niraparib can be about 40 hours, 42 hours, 44 hours, 46 hours, 48 hours, 50 hours, 52 hours, 54 hours, 56 hours, 58 hours or 60 hours. For example, following administration of niraparib provided in a composition described herein, the mean terminal half-life ($t_{1/2}$) of niraparib can be about 48 to 51 hours. For example, following administration of niraparib provided in a composition described herein, the mean terminal half-life ($t_{1/2}$) of niraparib can be about 48 hours, 49 hours, 50 hours or 51 hours.

In some embodiments, following administration of niraparib provided in a composition described herein, the apparent total clearance (CL/F) of niraparib is from about 10 L/hour to about 20 L/hour. For example, following administration of niraparib provided in a composition described herein, the apparent total clearance (CL/F) of niraparib can be about 10 L/hour, 11 L/hour, 12 L/hour, 13 L/hour, 14 L/hour, 15 L/hour, 16 L/hour, 17 L/hour, 18 L/hour, 19 L/hour or 20 L/hour. For example, following administration of niraparib provided in a composition described herein, the apparent total clearance (CL/F) of niraparib can be about 16.2 L/hour.

In some embodiments, the formulations disclosed herein provide a release of niraparib from the composition within 1 minute, or within 5 minutes, or within 10 minutes, or within 15 minutes, or within 30 minutes, or within 60 minutes or within 90 minutes. In other embodiments, a therapeutically effective amount of niraparib is released from the composition within 1 minute, or within 5 minutes, or within 10 minutes, or within 15 minutes, or within 30 minutes, or within 60 minutes or within 90 minutes. In some embodiments the composition comprises a niraparib tablet formulation providing immediate release of niraparib. In some embodiments the composition comprises a niraparib tablet formulation providing immediate release of niraparib within 1 minute, or within 5 minutes, or within 10 minutes, or within 15 minutes, or within 30 minutes, or within 60 minutes or within 90 minutes.

The niraparib formulations and dosage forms described herein display pharmacokinetic profiles that can result in $C_{min}$ niraparib blood plasma levels at steady state from about 10 ng/ml to about 100 ng/ml. In one embodiment, the niraparib formulations described herein provide blood plasma levels immediately prior to the next dose ($C_{min}$) at steady state from about 25 ng/ml to about 100 ng/ml. In another embodiment, the niraparib formulations described herein provide $C_{min}$ blood plasma levels at steady state from about 40 ng/ml to about 75 ng/ml. In yet another embodiment, the niraparib formulations described herein provide $C_{min}$ blood plasma levels at steady state of about 50 ng/ml.

The niraparib formulations described herein are administered and dosed in accordance with good medical practice, taking into account the clinical condition of the individual patient, the site and method of administration, scheduling of administration, and other factors known to medical practitioners. In human therapy, the dosage forms described herein deliver niraparib formulations that maintain a therapeutically effective amount of niraparib of at least 10 ng/ml or typically at least about 100 ng/ml in plasma at steady state while reducing the side effects associated with an elevated $C_{max}$ blood plasma level of niraparib.

In some embodiments, greater than about 95%; or greater than about 90%; or greater than about 80%; or greater than about 70% of the niraparib dosed by weight is absorbed into the bloodstream within about 1, 2, 3, 4, 5, 6, 7, 8, 9, 10, 11, 12, 16, 18, or 24 hours after administration.

Niraparib Concentration/Amount

By means of methods and compositions described herein, formulations can be made that achieve the desired disintegration characteristics and target pharmacokinetic profiles described herein. For example, therapeutically effective doses of niraparib can be administered once, twice or three times daily in tablets using the manufacturing methods and compositions that have been described herein to achieve these results. In some embodiments, the niraparib or a pharmaceutically acceptable prodrug or salt thereof is present in an amount of about 20-80 wt %, 45-70 wt %, 40-50 wt %, 45-55 wt %, 50-60 wt %, 55-65 wt %, 60-70 wt %, 65-75 wt %, 70-80 wt %, or 40-60 wt %. In some embodiments, the niraparib or a pharmaceutically acceptable prodrug or salt thereof is present in an amount of about 40-60 wt % of the core tablet weight (e.g., the combined weight of intragranular and extragranular components). In some embodiments, the niraparib or a pharmaceutically acceptable prodrug or salt thereof is present in an amount of about 40-60 wt % of the total tablet weight (e.g., the combined weight of intragranular components, extragranular components, and a coating). In some embodiments, the niraparib or a pharmaceutically acceptable prodrug or salt thereof is present in an amount of about 40-50 wt % of the core tablet weight (e.g., the combined weight of intragranular and extragranular components). In some embodiments, the niraparib or a pharmaceutically acceptable prodrug or salt thereof is present in an amount of about 40-50 wt % of the total tablet weight (e.g., the combined weight of intragranular components, extragranular components, and a coating).

In some embodiments, the compositions described herein have a concentration of niraparib or a pharmaceutically acceptable prodrug or salt thereof of from about 1% to about 70%, from about 5% to about 70%, from about 10% to about 70%, from about 15% to about 70%, from about 20% to about 70%, from about 25% to about 70%, from about 30% to about 70%, from about 35% to about 70%, from about 40% to about 70%, from about 45% to about 70%, from about 50% to about 70%, from about 55% to about 70%, from about 60% to about 70%, from about 65% to about 70% by weight of the composition.

In some embodiments, the compositions described herein have a concentration of niraparib or a pharmaceutically acceptable prodrug or salt thereof of from about 1% to about 65%, from about 5% to about 65%, from about 10% to about 65%, from about 15% to about 65%, from about 20% to about 65%, from about 25% to about 65%, from about 30% to about 65%, from about 35% to about 65%, from about 40% to about 65%, from about 45% to about 65%, from about 50% to about 65%, from about 55% to about 65%, or from about 60% to about 65% by weight of the composition.

In some embodiments, the compositions described herein have a concentration of niraparib or a pharmaceutically acceptable prodrug or salt thereof of from about 1% to about 60%, from about 5% to about 60%, from about 10% to about 60%, from about 15% to about 60%, from about 20% to about 60%, from about 25% to about 60%, from about 30% to about 60%, from about 35% to about 60%, from about 40% to about 60%, from about 45% to about 60%, from about 50% to about 60%, or from about 55% to about 60% by weight of the composition.

In some embodiments, the compositions described herein have a concentration of niraparib or a pharmaceutically acceptable prodrug or salt thereof of from about 1% to about 55%, from about 5% to about 55%, from about 10% to about 55%, from about 15% to about 55%, from about 20% to about 55%, from about 25% to about 55%, from about 30% to about 55%, from about 35% to about 55%, from about 40% to about 55%, from about 45% to about 55%, or from about 50% to about 55% by weight of the composition.

In some embodiments, the compositions described herein have a concentration of niraparib or a pharmaceutically acceptable prodrug or salt thereof of from about 1% to about 50%, from about 5% to about 50%, from about 10% to about 50%, from about 15% to about 50%, from about 20% to about 50%, from about 25% to about 50%, from about 30% to about 50%, from about 35% to about 50%, from about 40% to about 50%, or from about 45% to about 50% by weight of the composition.

In some embodiments, the compositions described herein have a concentration of niraparib or a pharmaceutically acceptable prodrug or salt thereof of from about 1% to about 45%, from about 5% to about 45%, from about 10% to about 45%, from about 15% to about 45%, from about 20% to about 45%, from about 25% to about 45%, from about 30% to about 45%, from about 35% to about 45%, or from about 40% to about 45% by weight of the composition.

In some embodiments, the compositions described herein have a concentration of niraparib or a pharmaceutically acceptable prodrug or salt thereof of from about 1% to about 40%, from about 5% to about 40%, from about 10% to about 40%, from about 15% to about 40%, from about 20% to about 40%, from about 25% to about 40%, from about 30% to about 40%, or from about 35% to about 40% by weight of the composition.

In some embodiments, the compositions described herein have a concentration of niraparib or a pharmaceutically acceptable prodrug or salt thereof of from about 1% to about 35%, from about 5% to about 35%, from about 10% to about 35%, from about 15% to about 35%, from about 20% to about 35%, from about 25% to about 35%, or from about 30% to about 35% by weight of the composition.

In some embodiments, the compositions described herein have a concentration of niraparib or a pharmaceutically acceptable prodrug or salt thereof of about 1%, 5%, 10%, 15%, 20%, 25%, 30%, 35%, 40%, 45%, 50%, 55%, or 60% by weight of the composition. In some embodiments, the compositions described herein have a concentration of niraparib tosylate monohydrate of about 19.16% by weight of the composition. In some embodiments, the compositions described herein have a concentration of niraparib tosylate monohydrate of about 38.32% by weight of the composition. In some embodiments, the compositions described herein have a concentration of niraparib tosylate monohydrate of about 47.8% by weight of the composition. In some embodiments, the compositions described herein have a concentration of niraparib tosylate monohydrate of about 57.48% by weight of the composition. In some embodiments, the compositions described herein have a concentration of niraparib tosylate monohydrate of about 76.64% by weight of the composition.

In some embodiments, the compositions described herein have an amount of niraparib or a pharmaceutically acceptable prodrug or salt thereof of from about 1 mg to 5 mg, 5 mg to 10 mg, 10 mg to 20 mg, 20 mg to 25 mg, 25 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, 950 mg to 1000 mg, 1000 mg to 1050 mg, 1050 mg to 1100 mg, 1100 mg to 1150 mg, 1150 mg to 1200 mg, 1200 mg to 1250 mg, 1250 mg to 1300 mg, 1300 mg to 1350 mg, 1350 mg to 1400 mg, 1400 mg to 1450 mg, 1450 mg to 1500 mg, 1500 mg to 1550 mg, 1550 mg to 1600 mg, 1600 mg to 1650 mg, 1650 mg to 1700 mg, 1700 mg to 1750 mg, 1750 mg to 1800 mg, 1800 mg to 1850 mg, 1850 mg to 1900 mg, 1900 mg to 1950 mg, or 1950 mg to 2000 mg. For example, the compositions described herein can have an amount of niraparib tosylate monohydrate of from about 1 mg to about 2000 mg, for example, from about 1 mg to 5 mg, 5 mg to 10 mg, 10 mg to 20 mg, 20 mg to 25 mg, 25 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, 950 mg to 1000 mg, 1000 mg to 1050 mg, 1050 mg to 1100 mg, 1100 mg to 1150 mg, 1150 mg to 1200 mg, 1200 mg to 1250 mg, 1250 mg to 1300 mg, 1300 mg to 1350 mg, 1350 mg to 1400 mg, 1400 mg to 1450 mg, 1450 mg to 1500 mg, 1500 mg to 1550 mg, 1550 mg to 1600 mg, 1600 mg to 1650 mg, 1650 mg to 1700 mg, 1700 mg to 1750 mg, 1750 mg to 1800 mg, 1800 mg to 1850 mg, 1850 mg to 1900 mg, 1900 mg to 1950 mg, or 1950 mg to 2000 mg.

In some embodiments, the compositions described herein have an amount of niraparib or a pharmaceutically acceptable prodrug or salt of about 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, or 2000 mg. For example, the compositions described herein can have an amount of niraparib tosylate monohydrate of about 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, or 2000 mg.

In some embodiments, the compositions described herein have an amount of niraparib or a pharmaceutically acceptable prodrug or salt thereof of about 25 mg, about 50 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg. For example, the compositions described herein can have an amount of niraparib tosylate monohydrate of about 25 mg, about 50 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg. In some embodiments, the compositions described herein have an amount of niraparib tosylate monohydrate of about 79.7 mg. In some embodiments, the compositions described herein have an amount of niraparib tosylate monohydrate of about 159.4 mg. In some embodiments, the compositions described herein have an amount of niraparib tosylate monohydrate of about 318.8 mg. In some embodiments, the compositions described herein have an amount of niraparib tosylate monohydrate of about 478.0 mg.

Pharmaceutically Acceptable Salts

In some embodiments, the niraparib used in a composition disclosed herein is the form of a free base, pharmaceutically acceptable salt, prodrug, analog or complex. In some instances, the niraparib comprises the form of a pharmaceutically acceptable salt. In some embodiments, with respect to niraparib in a composition, a pharmaceutically acceptable salt includes, but is not limited to, 4-methylbenzenesulfonate salts, sulfate salts, benzenesulfate salts, fumarate salts, succinate salts, and stereoisomers or tautomers thereof. In some embodiments, with respect to niraparib in a composition, a pharmaceutically acceptable salt includes, but is not limited to, tosylate salts. In some embodiments, with respect to niraparib in a composition, a pharmaceutically acceptable salt includes, but is not limited to, tosylate monohydrate salts.

Additional Pharmaceutically Acceptable Excipients

In some aspects, the pharmaceutical composition disclosed herein further comprises one or more pharmaceutically acceptable excipients. In some embodiments, the one or more pharmaceutically acceptable excipient is present in an amount of about 0.1-99% by weight. Exemplary pharmaceutically acceptable excipients for the purposes of pharmaceutical compositions disclosed herein include, but are not limited to, binders, disintegrants, superdisintegrants, lubricants, diluents, fillers, flavors, glidants, sorbents, solubilizers, chelating agents, emulsifiers, thickening agents, dispersants, stabilizers, suspending agents, adsorbents, granulating agents, preservatives, buffers, coloring agents and sweeteners or combinations thereof. Examples of binders include microcrystalline cellulose, hydroxypropyl methylcellulose, carboxyvinyl polymer, polyvinylpyrrolidone, polyvinylpolypyrrolidone, carboxymethylcellulose calcium, carboxymethylcellulose sodium, ceratonia, chitosan, cottonseed oil, dextrates, dextrin, ethylcellulose, gelatin, glucose, glyceryl behenate, galactomannan polysaccharide, hydroxyethyl cellulose, hydroxyethylmethyl cellulose, hydroxypropyl cellulose, hypromellose, inulin, lactose, magnesium aluminum silicate, maltodextrin, methylcellulose, poloxamer, polycarbophil, polydextrose, polyethylene glycol, polyethylene oxide, polymethacrylates, sodium alginate, sorbitol, starch, sucrose, sunflower oil, vegetable oil, tocofersolan, zein, or combinations thereof. Examples of disintegrants include hydroxypropyl methylcellulose (HPMC), low substituted hydroxypropyl cellulose (L-HPC), croscarmellose sodium, sodium starch glycolate, lactose, magnesium aluminum silicate, methylcellulose, polacrilin potassium, sodium alginate, starch, or combinations thereof. Examples of a lubricant include stearic acid, sodium stearyl fumarate, glyceryl behenate, calcium stearate, glycerin monostearate, glyceryl palmitostearate, magnesium lauryl sulfate, mineral oil, palmitic acid, myristic acid, poloxamer, polyethylene glycol, sodium benzoate, sodium chloride, sodium lauryl sulfate, talc, zinc stearate, potassium benzoate, magnesium stearate or combinations thereof. Examples of diluents include talc, ammonium alginate, calcium carbonate, calcium lactate, calcium phosphate, calcium silicate, calcium sulfate, cellulose, cellulose acetate, corn starch, dextrates, dextrin, dextrose, erythritol, ethylcellulose, fructose, fumaric acid, glyceryl palmitostearate, isomalt, kaolin, lactitol, lactose, magnesium carbonate, magnesium oxide, maltodextrin, maltose, mannitol, microcrystalline cellulose, polydextrose, polymethacrylates, simethicone, sodium alginate, sodium chloride, sorbitol, starch, sucrose, sulfobutylether β-cyclodextrin, tragacanth, trehalose, xylitol, or combinations thereof. In some embodiments, the pharmaceutically acceptable excipient is hydroxypropyl methylcellulose (HPMC). In some embodiments, the pharmaceutically acceptable excipient is low substituted hydroxypropyl cellulose (L-HPC). In some embodiments, the pharmaceutically acceptable excipient is lactose. In some embodiments, the pharmaceutically acceptable excipient is lactose monohydrate. In some embodiments, the pharmaceutically acceptable excipient is magnesium stearate. In some embodiments, the pharmaceutically acceptable excipient is lactose monohydrate and magnesium stearate.

Various useful fillers or diluents include, but are not limited to calcium carbonate (Barcroft™, MagGran™, Millicarb™, Pharma-Carb™, Precarb™, Sturcal™, Vivapres Ca™) calcium phosphate, dibasic anhydrous (Emcompress Anhydrous™, Fujicalin™), calcium phosphate, dibasic dihydrate (Calstar™, Di-Cafos™, Emcompress™), calcium phosphate tribasic (Tri-Cafos™, TRI-TAB™), calcium sulphate (Destab™, Drierite™, Snow White™, Cal-Tab™, Compactrol™) cellulose powdered (Arbocel™, Elcema™, Sanacet™), silicified microcrystalline cellulose, cellulose acetate, compressible sugar (Di-Pac™), confectioner's sugar, dextrates (Candex™, Emdex™) dextrin (Avedex™, Caloreen™, Primogran W™), dextrose (Caridex™, Dextrofin™, Tab fine D-IOO™), fructose (Fructofin™, Krystar™), kaolin (Lion™, Sim 90™), lactitol (Finlac DC™, Finlac MCX™), lactose (Anhydrox™, CapsuLac™, Fast-Flo™, FlowLac™, GranuLac™, InhaLac™, Lactochem™, Lactohaie™, Lactopress™, Microfme™, Microtose™, Pharmatose™, Prisma Lac™, Respitose™, SacheLac™, SorboLac™, Super-Tab™, Tablettose™, Wyndale™, Zeparox™), lactose monohydrate, magnesium carbonate, magnesium oxide (MagGran MO™), maltodextrin (C*Dry MD™, Lycatab DSH™, Maldex™, Maitagran™, Maltrin™, Maltrin QD™, Paselli MD 10 PH™, Star-Dri™), maltose (Advantose 100™), mannitol (Mannogem™, Pearlitol™), microcrystalline cellulose (Avicel PH™, Celex™, Celphere™, Ceolus KG™, Emcocel™, Pharmacel™, Tabulose™, Vivapur™), polydextrose (Litesse™), simethicone (Dow Corning Q7-2243 LVA™, Dow Corning Q72587™, Sentry Simethicone™), sodium alginate (Keltone™, Protanal™), sodium chloride (Alberger™), sorbitol (Liponec 70-NC™, Liponic 76-NCv, Meritol™, Neosorb™, Sorbitol Instant™, Sorbogem™), starch (Flufiex W™, Instant Pure-Cote™, Melojei™, Meritena Paygel 55™, Perfectamyl D6PH™, Pure-Cote™, Pure-Dent™, Pure-Gel™, Pure-Set™, Purity 21™, Purity 826™, Tablet White™), pregelatinized starch, sucrose, trehalose and xylitol, or mixtures thereof.

Various useful disintegrants include, but are not limited to, alginic acid (Protacid™, Satialgine H8™), calcium phosphate, tribasic (TRI-TAB™), carboxymethylcellulose calcium (ECG 505™), carboxymethylcellulose sodium (Akucell™, Finnfix™, Nymcel Tylose CB™), colloidal silicon dioxide (Aerosil™, Cab-O-Sil™, Wacker HDK™), croscarmellose sodium (Ac-Di-Sol™, Pharmacel XL™, Primellose™, Solutab™, Vivasol™), crospovidone (Collison CL™, Collison CL-M™, Polyplasdone XL™), docusate sodium, guar gum (Meyprodor™, Meyprofm™, Meyproguar™), low substituted hydroxypropyl cellulose, magnesium aluminum silicate (Magnabite™, Neusilin™, Pharmsorb™, Veegum™), methylcellulose (Methocel™, Metolose™) microcrystalline cellulose (Avicel PH™, Ceoius KG™, Emcoel™, Ethispheres™, Fibrocel™, Pharmacel™, Vivapur™), povidone (Collison™, Plasdone™) sodium alginate (Kelcosol™, Ketone™, Protanal™), sodium starch glycolate, polacrilin potassium (Amberlite IRP88™), silicified microcrystalline cellulose (ProSotv™), starch (AytexP™, Fluftex W™, Melojel™, Meritena™, Paygel 55™, Perfectamyl D6PH™, Pure-Bind™, Pure-Cote™, Pure-Dent™, Purity 21™, Purity 826™, Tablet White™) or pre-gelatinized starch (Lycatab PGS™, Merigel™, National 781551™, Pharma-Gel™, Prejel™, Sepistab ST 200™, Spress B820™, Starch 1500 G™, Tablitz™, Unipure LD™), or mixtures thereof. In some embodiments, a disintegrant is optionally used in an amount of about 0.1-99% by weight. In some embodiments, a disintegrant is optionally used in an amount of about 0.1-50% by weight. In some embodiments, a disintegrant is optionally used in an amount of about 0.1-10% by weight. In some embodiments, a disintegrant is present in an amount of from about 0.1 mg to 0.5 mg, 0.5 mg to 1 mg, 1 mg to 2 mg, 2 mg to 2.5 mg, 2.5 mg to 5 mg, 5 mg to 7.5 mg, 7 mg to 9.5 mg, 9 mg to 11.5 mg, 11 mg to 13.5 mg, 13 mg to 15.5 mg, 15 mg to 17.5 mg, 17 to 19.5 mg, 19 mg to 21.5 mg, 21 mg to 23.5 mg, 23 mg to 25.5 mg, 25 mg to 27.5 mg, 27 mg to 30 mg, 29 mg to 31.5 mg, 31 mg to 33.5 mg, 33 mg to 35.5 mg, 35 mg to 37.5 mg, 37 mg to 40 mg, 40 mg to 45 mg, 45 mg to 50 mg, 50 mg to 55 mg, 55 mg to 60 mg, 60 mg to 65 mg, 65 mg to 70 mg, 70 mg to 75 mg, 75 mg to 80 mg, 80 mg to 85 mg, 85 mg to 90 mg, 90 mg to 95 mg, or 95 mg to 100 mg. In some embodiments, a disintegrant is present in an amount of about 0.1 mg, 0.5 mg, 1 mg, 2 mg, 2.5 mg, 5 mg, 7 mg, 9 mg, 11 mg, 13 mg, 15 mg, 17 mg, 19 mg, 21 mg, 23 mg, 25 mg, 27.5 mg, 30 mg, 31.5 mg, 33.5 mg, 35.5 mg, 37.5 mg, 40 mg, 45 mg, 50 mg, 55 mg, 60 mg, 65 mg, 70 mg, 75 mg, 80 mg, 85 mg, 90 mg, 95 mg, or 100 mg.

Various useful lubricants include, but are not limited to, calcium stearate (HyQual™) glycerine monostearate (Imwitor™ 191 and 900, Kessco GMSS™, 450 and 600, Myvaplex 600P™, Myvatex™, Rita GMS™, Stepan GMS™, Tegin™, Tegin™ 503 and 515, Tegin 4100™, Tegin M™ Unimate GMS™), glyceryl behenate (Compritol 888 ATO™), glyceryl palmitostearate (Precirol ATO 5™) hydrogenated castor oil (Castorwax MP 80™, Croduret™, Cutina HR™, Fancol™, Simulsol 1293™), hydrogenated vegetable oil 0 type I (Sterotex™, Dynasan P60™, Hydrocote™, Lipovol HS-K™, Sterotex HM™), magnesium lauryl sulphate, magnesium stearate, medium-chain triglycerides (Captex 300™, Labrafac CC™, Miglyol 810™, Neobee M5™, Nesatol™, Waglinol 3/9280™), poloxamer (Pluronic™, Synperonic™), polyethylene 5 glycol (Carbowax Sentry™, Lipo™, Lipoxol™, Lutrol E™, Pluriol E™), sodium benzoate (Antimol™) sodium chloride, sodium lauryl sulphate (Elfan 240™, Texapon Kl 2P™), sodium stearyl fumarate (Pruv™), stearic acid (Hystrene™, Industrene™, Kortacid 1895™, Pristerene™), talc (Altaic™, Luzenac™, Luzenac Pharma™, Magsil Osmanthus™, 0 Magsil Star™, Superiore™), sucrose stearate (Surfhope SE Pharma D-1803 F™) and zinc stearate (HyQual™) or mixtures thereof. Examples of suitable lubricants include, but are not limited to, magnesium stearate, calcium stearate, zinc stearate, stearic acid, talc, glyceryl behenate, polyethylene glycol, polyethylene oxide polymers, sodium lauryl sulfate, magnesium lauryl sulfate, sodium oleate, sodium stearyl fumarate, DL-leucine, colloidal silica, and others as known in the art. In some embodiments a lubricant is magnesium stearate.

Various useful glidants include, but are not limited to, tribasic calcium phosphate (TRI-TAB™), calcium silicate, cellulose, powdered (Sanacel™, Solka-Floe™), colloidal silicon dioxide (Aerosil™, Cab-O-Sil M-5P™, Wacker HDK™), magnesium silicate, magnesium trisilicate, starch (Melojel™, Meritena™, Paygel 55™, Perfectamyl D6PH™, Pure-Bind™, Pure-Cote™, Pure-Dent™, Pure-Gel™, Pure-Set™, Purity 21™, Purity 826™, Tablet White™) and talc (Luzenac Pharma™, Magsil Osmanthus™, Magsil Star™, Superiore™), or mixtures thereof. In some embodiments, a glidant is optionally used in an amount of about 0-15% by weight. In some embodiments, a glidant is present in an amount of from about 0.1 mg to 0.5 mg, 0.5 mg to 1 mg, 1 mg to 2 mg, 2 mg to 2.5 mg, 2.5 mg to 5 mg, 5 mg to 7.5 mg, 7 mg to 9.5 mg, 9 mg to 11.5 mg, 11 mg to 13.5 mg, 13 mg to 15.5 mg, 15 mg to 17.5 mg, 17 to 19.5 mg, 19 mg to 21.5 mg, 21 mg to 23.5 mg, 23 mg to 25.5 mg, 25 mg to 27.5 mg, 27 mg to 30 mg, 29 mg to 31.5 mg, 31 mg to 33.5 mg, 33 mg to 35.5 mg, 35 mg to 37.5 mg, 37 mg to 40 mg, 40 mg to 45 mg, 45 mg to 50 mg, 50 mg to 55 mg, 55 mg to 60 mg, 60 mg to 65 mg, 65 mg to 70 mg, 70 mg to 75 mg, 75 mg to 80 mg, 80 mg to 85 mg, 85 mg to 90 mg, 90 mg to 95 mg, or 95 mg to 100 mg. In some embodiments, a glidant is present in an amount of about 0.1 mg, 0.5 mg, 1 mg, 2 mg, 2.5 mg, 5 mg, 7 mg, 9 mg, 11 mg, 13 mg, 15 mg, 17 mg, 19 mg, 21 mg, 23 mg, 25 mg, 27.5 mg, 30 mg, 31.5 mg, 33.5 mg, 35.5 mg, 37.5 mg, 40 mg, 45 mg, 50 mg, 55 mg, 60 mg, 65 mg, 70 mg, 75 mg, 80 mg, 85 mg, 90 mg, 95 mg, or 100 mg.

Pharmaceutically acceptable surfactants include, but are limited to both non-ionic and ionic surfactants suitable for use in pharmaceutical dosage forms. Ionic surfactants may include one or more of anionic, cationic or zwitterionic surfactants. Various useful surfactants include, but are not limited to, sodium lauryl sulfate, monooleate, monolaurate, monopalmitate, monostearate or another ester of polyoxyethylene sorbitan, sodium dioctylsulfosuccinate (DOSS), lecithin, stearyl alcohol, cetostearylic alcohol, cholesterol, polyoxyethylene ricin oil, polyoxyethylene fatty acid glycerides, poloxamer, or any other commercially available co-processed surfactant like SEPITRAP® 80 or SEPITRAP® 4000 and mixtures thereof. In some embodiments, surfactant is optionally used in an amount of about 0-5% by weight. In some embodiments, a surfactant is present in an amount of from about 0.1 mg to 0.5 mg, 0.5 mg to 1 mg, 1 mg to 2 mg, 2 mg to 2.5 mg, 2.5 mg to 5 mg, 5 mg to 7.5 mg, 7 mg to 9.5 mg, 9 mg to 11.5 mg, 11 mg to 13.5 mg, 13 mg to 15.5 mg, 15 mg to 17.5 mg, 17 to 19.5 mg, 19 mg to 21.5 mg, 21 mg to 23.5 mg, 23 mg to 25.5 mg, 25 mg to 27.5 mg, 27 mg to 30 mg, 29 mg to 31.5 mg, 31 mg to 33.5 mg, 33 mg to 35.5 mg, 35 mg to 37.5 mg, 37 mg to 40 mg, 40 mg to 45 mg, 45 mg to 50 mg, 50 mg to 55 mg, 55 mg to 60 mg, 60 mg to 65 mg, 65 mg to 70 mg, 70 mg to 75 mg, 75 mg to 80 mg, 80 mg to 85 mg, 85 mg to 90 mg, 90 mg to 95 mg, or 95 mg to 100 mg. In some embodiments, a surfactant is present in an amount of about 0.1 mg, 0.5 mg, 1 mg, 2 mg, 2.5 mg, 5 mg, 7 mg, 9 mg, 11 mg, 13 mg, 15 mg, 17 mg, 19 mg, 21 mg, 23 mg, 25 mg, 27.5 mg, 30 mg, 31.5 mg, 33.5 mg, 35.5 mg, 37.5 mg, 40 mg, 45 mg, 50 mg, 55 mg, 60 mg, 65 mg, 70 mg, 75 mg, 80 mg, 85 mg, 90 mg, 95 mg, or 100 mg.

Exemplary Tablet Compositions

Exemplary tablet compositions include Formulations 1-6 described herein in Examples 1 and 2. Still other exemplary compositions can include those described in Tables 1-12, where the total core tablet weight comprises the combined weight of intragranular components and extragranualar components.

In embodiments, a tablet composition is any formulation described in Table 1 comprising about 478 mg niraparib tosylate monohydrate. In embodiments, a tablet composition is Formulation 7. In embodiments, a tablet composition is Formulation 8. In embodiments, a tablet composition is Formulation 9.

TABLE 1

Exemplary 300 mg niraparib tablets (Formulations 7-9)

| Component | Weight %* | Formulation 7 | Formulation 8 | Formulation 9 |
|---|---|---|---|---|
| Intragranular Phase (~94-98% of total core tablet weight) | | | | |
| Active | about 40-50 | niraparib tosylate monohydrate | | |
| Diluent 1 | about 8-14 | lactose monohydrate | | |
| Diluent 2 | about 30-40 | microcrystalline cellulose | | |
| Binder | about 1-3 | povidone | | |
| Distintegrant | about 0.1-2 | crospovidone | | |
| Glidant/Absorbant/Adsorbant | about 2-4 | silicon dioxide | | |
| Lubricant | about 0.1-2 | magnesium stearate | | |

TABLE 1-continued

Exemplary 300 mg niraparib tablets (Formulations 7-9)

| Component | Weight %* | Formulation 7 | Formulation 8 | Formulation 9 |
|---|---|---|---|---|
| Extragranular Phase (~2-6 wt % of core tablet weight) | | | | |
| Distintegrant | about 0.1-2 | crospovidone | | |
| Glidant/Absorbant/Adsorbant | about 0.1-2 | silicon dioxide | | |
| Lubricant | about 0.1-2 | magnesium stearate | | |
| Total Core Tablet Weight | — | ~950-1050 mg | ~1050-1150 mg | ~1150-1250 mg |

*based on total core tablet weight (sum of intragranular + extragranular phases)

In embodiments, a tablet composition is any formulation described in Table 2 comprising about 478 mg niraparib tosylate monohydrate. In embodiments, a tablet composition is Formulation 10. In embodiments, a tablet composition is Formulation 11. In embodiments, a tablet composition is Formulation 12.

TABLE 2

Exemplary 300 mg niraparib tablets (Formulations 10-12)

| Component | Weight %* | Formulation 10 | Formulation 11 | Formulation 12 |
|---|---|---|---|---|
| Intragranular Phase (~94-98% of total core tablet weight) | | | | |
| Active | about 40-50 | niraparib tosylate monohydrate | | |
| Diluent 1 | about 8-14 | lactose anhydrous | | |
| Diluent 2 | about 30-40 | microcrystalline cellulose | | |
| Binder | about 1-3 | povidone | | |
| Distintegrant | about 0.1-2 | crospovidone | | |
| Glidant/Absorbant/Adsorbant | about 2-4 | silicon dioxide | | |
| Lubricant | about 0.1-2 | magnesium stearate | | |
| Extragranular Phase (~2-6 wt % of core tablet weight) | | | | |
| Distintegrant | about 0.1-2 | croscarmellose sodium | | |
| Glidant/Absorbant/Adsorbant | about 0.1-2 | silicon dioxide | | |
| Lubricant | about 0.1-2 | magnesium stearate | | |
| Total Core Tablet Weight | — | ~950-1050 mg | ~1050-1150 mg | ~1150-1250 mg |

*based on total core tablet weight (sum of intragranular + extragranular phases)

In embodiments, a tablet composition is any formulation described in Table 3 comprising about 478 mg niraparib tosylate monohydrate. In embodiments, a tablet composition is Formulation 13. In embodiments, a tablet composition is Formulation 14. In embodiments, a tablet composition is Formulation 15.

TABLE 3

Exemplary 300 mg niraparib tablets (Formulations 13-15)

| Component | Weight %* | Formulation 13 | Formulation 14 | Formulation 15 |
|---|---|---|---|---|
| Intragranular Phase (~94-98% of total core tablet weight) | | | | |
| Active | about 40-50 | niraparib tosylate monohydrate | | |
| Diluent 1 | about 8-14 | lactose monohydrate | | |
| Diluent 2 | about 30-40 | microcrystalline cellulose | | |
| Binder | about 1-3 | povidone | | |

TABLE 3-continued

Exemplary 300 mg niraparib tablets (Formulations 13-15)

| Component | Weight %* | Formulation 13 | Formulation 14 | Formulation 15 |
|---|---|---|---|---|
| Distintegrant | about 0.1-2 | crospovidone | | |
| Glidant/Absorbant/Adsorbant | about 2-4 | silicon dioxide | | |
| Extragranular Phase (~2-6 wt % of core tablet weight) | | | | |
| Distintegrant | about 0.1-2 | crospovidone | | |
| Glidant/Absorbant/Adsorbant | about 0.1-2 | silicon dioxide | | |
| Lubricant | about 0.1-2 | magnesium stearate | | |
| Total Core Tablet Weight | — | ~950-1050 mg | ~1050-1150 mg | ~1150-1250 mg |

*based on total core tablet weight (sum of intragranular + extragranular phases)

In embodiments, a tablet composition is any formulation described in Table 4 comprising about 478 mg niraparib tosylate monohydrate. In embodiments, a tablet composition is Formulation 16. In embodiments, a tablet composition is Formulation 17. In embodiments, a tablet composition is Formulation 18.

TABLE 4

Exemplary 300 mg niraparib tablets (Formulations 16-18)

| Component | Weight %* | Formulation 16 | Formulation 17 | Formulation 18 |
|---|---|---|---|---|
| Intragranular Phase (~94-98% of total core tablet weight) | | | | |
| Active | about 40-50 | niraparib tosylate monohydrate | | |
| Diluent 1 | about 8-14 | lactose anhydrous | | |
| Diluent 2 | about 30-40 | microcrystalline cellulose | | |
| Binder | about 1-3 | povidone | | |
| Distintegrant | about 0.1-2 | crospovidone | | |
| Glidant/Absorbant/Adsorbant | about 2-4 | silicon dioxide | | |
| Extragranular Phase (~2-6 wt % of core tablet weight) | | | | |
| Distintegrant | about 0.1-2 | croscarmellose sodium | | |
| Glidant/Absorbant/Adsorbant | about 0.1-2 | silicon dioxide | | |
| Lubricant | about 0.1-2 | magnesium stearate | | |
| Total Core Tablet Weight | — | ~950-1050 mg | ~1050-1150 mg | ~1150-1250 mg |

*based on total core tablet weight (sum of intragranular + extragranular phases)

In embodiments, a tablet composition is any formulation described in Table 5 comprising about 318.7 mg niraparib tosylate monohydrate. In embodiments, a tablet composition is Formulation 19. In embodiments, a tablet composition is Formulation 20. In embodiments, a tablet composition is Formulation 21.

TABLE 5

Exemplary 200 mg niraparib tablets (Formulations 19-21)

| Component | Weight %* | Formulation 19 | Formulation 20 | Formulation 21 |
|---|---|---|---|---|
| Intragranular Phase (~94-98% of total core tablet weight) | | | | |
| Active | about 40-50 | niraparib tosylate monohydrate | | |
| Diluent 1 | about 8-14 | lactose monohydrate | | |
| Diluent 2 | about 30-40 | microcrystalline cellulose | | |
| Binder | about 1-3 | povidone | | |
| Distintegrant | about 0.1-2 | crospovidone | | |
| Glidant/Absorbant/Adsorbant | about 2-4 | silicon dioxide | | |
| Lubricant | about 0.1-2 | magnesium stearate | | |
| Extragranular Phase (~2-6 wt % of core tablet weight) | | | | |
| Distintegrant | about 0.1-2 | crospovidone | | |
| Glidant/Absorbant/Adsorbant | about 0.1-2 | silicon dioxide | | |
| Lubricant | about 0.1-2 | magnesium stearate | | |
| Total Core Tablet Weight | — | ~600-650 mg | ~650-700 mg | ~700-750 mg |

*based on total core tablet weight (sum of intragranular + extragranular phases)

In embodiments, a tablet composition is any formulation described in Table 6 comprising about 318.7 mg niraparib tosylate monohydrate. In embodiments, a tablet composition is Formulation 22. In embodiments, a tablet composition is Formulation 23. In embodiments, a tablet composition is Formulation 24.

TABLE 6

Exemplary 200 mg niraparib tablets (Formulations 22-24)

| Component | Weight %* | Formulation 22 | Formulation 23 | Formulation 24 |
|---|---|---|---|---|
| Intragranular Phase (~94-98% of total core tablet weight) | | | | |
| Active | about 40-50 | niraparib tosylate monohydrate | | |
| Diluent 1 | about 8-14 | lactose anhydrous | | |
| Diluent 2 | about 30-40 | microcrystalline cellulose | | |
| Binder | about 1-3 | povidone | | |
| Distintegrant | about 0.1-2 | crospovidone | | |
| Glidant/Absorbant/Adsorbant | about 2-4 | silicon dioxide | | |
| Lubricant | about 0.1-2 | magnesium stearate | | |
| Extragranular Phase (~2-6 wt % of core tablet weight) | | | | |
| Distintegrant | about 0.1-2 | croscarmellose sodium | | |
| Glidant/Absorbant/Adsorbant | about 0.1-2 | silicon dioxide | | |
| Lubricant | about 0.1-2 | magnesium stearate | | |
| Total Core Tablet Weight | — | ~600-650 mg | ~650-700 mg | ~700-750 mg |

*based on total core tablet weight (sum of intragranular + extragranular phases)

In embodiments, a tablet composition is any formulation described in Table 7 comprising about 318.7 mg niraparib tosylate monohydrate. In embodiments, a tablet composition is Formulation 25. In embodiments, a tablet composition is Formulation 26. In embodiments, a tablet composition is Formulation 27.

TABLE 7

Exemplary 200 mg niraparib tablets (Formulations 25-27)

| Component | Weight %* | Formulation 25 | Formulation 26 | Formulation 27 |
|---|---|---|---|---|
| Intragranular Phase (~94-98% of total core tablet weight) | | | | |
| Active | about 40-50 | niraparib tosylate monohydrate | | |
| Diluent 1 | about 8-14 | lactose monohydrate | | |
| Diluent 2 | about 30-40 | microcrystalline cellulose | | |
| Binder | about 1-3 | povidone | | |
| Distintegrant | about 0.1-2 | crospovidone | | |
| Glidant/Absorbant/Adsorbant | about 2-4 | silicon dioxide | | |
| Extragranular Phase (~2-6 wt % of core tablet weight) | | | | |
| Distintegrant | about 0.1-2 | crospovidone | | |
| Glidant/Absorbant/Adsorbant | about 0.1-2 | silicon dioxide | | |
| Lubricant | about 0.1-2 | magnesium stearate | | |
| Total Core Tablet Weight | — | ~600-650 mg | ~650-700 mg | ~700-750 mg |

*based on total core tablet weight (sum of intragranular + extragranular phases)

In embodiments, a tablet composition is any formulation described in Table 8 comprising about 318.7 mg niraparib tosylate monohydrate. In embodiments, a tablet composition is Formulation 28. In embodiments, a tablet composition is Formulation 29. In embodiments, a tablet composition is Formulation 30.

TABLE 8

Exemplary 200 mg niraparib tablets (Formulations 28-30)

| Component | Weight %* | Formulation 28 | Formulation 29 | Formulation 30 |
|---|---|---|---|---|
| Intragranular Phase (~94-98% of total core tablet weight) | | | | |
| Active | about 40-50 | niraparib tosylate monohydrate | | |
| Diluent 1 | about 8-14 | lactose anhydrous | | |
| Diluent 2 | about 30-40 | microcrystalline cellulose | | |
| Binder | about 1-3 | povidone | | |
| Distintegrant | about 0.1-2 | crospovidone | | |
| Glidant/Absorbant/Adsorbant | about 2-4 | silicon dioxide | | |
| Extragranular Phase (~2-6 wt % of core tablet weight) | | | | |
| Distintegrant | about 0.1-2 | croscarmellose sodium | | |
| Glidant/Absorbant/Adsorbant | about 0.1-2 | silicon dioxide | | |
| Lubricant | about 0.1-2 | magnesium stearate | | |
| Total Core Tablet Weight | — | ~600-650 mg | ~650-700 mg | ~700-750 mg |

*based on total core tablet weight (sum of intragranular + extragranular phases)

In embodiments, a tablet composition is any formulation described in Table 9 comprising about 159.3 mg niraparib tosylate monohydrate. In embodiments, a tablet composition is Formulation 31. In embodiments, a tablet composition is Formulation 32. In embodiments, a tablet composition is Formulation 33.

TABLE 9

Exemplary 100 mg niraparib tablets (Formulations 31-33)

| Component | Weight %* | Formulation 31 | Formulation 32 | Formulation 33 |
|---|---|---|---|---|
| Intragranular Phase (~94-98% of total core tablet weight) | | | | |
| Active | about 40-50 | niraparib tosylate monohydrate | | |
| Diluent 1 | about 8-14 | lactose monohydrate | | |
| Diluent 2 | about 30-40 | microcrystalline cellulose | | |
| Binder | about 1-3 | povidone | | |
| Distintegrant | about 0.1-2 | crospovidone | | |
| Glidant/Absorbant/Adsorbant | about 2-4 | silicon dioxide | | |
| Lubricant | about 0.1-2 | magnesium stearate | | |
| Extragranular Phase (~2-6 wt % of core tablet weight) | | | | |
| Distintegrant | about 0.1-2 | crospovidone | | |
| Glidant/Absorbant/Adsorbant | about 0.1-2 | silicon dioxide | | |
| Lubricant | about 0.1-2 | magnesium stearate | | |
| Total Core Tablet Weight | — | ~300-350 mg | ~350-400 mg | ~400-450 mg |

*based on total core tablet weight (sum of intragranular + extragranular phases)

In embodiments, a tablet composition is any formulation described in Table 10 comprising about 159.3 mg niraparib tosylate monohydrate. In embodiments, a tablet composition is Formulation 34. In embodiments, a tablet composition is Formulation 35. In embodiments, a tablet composition is Formulation 36.

TABLE 10

Exemplary 100 mg niraparib tablets (Formulations 34-36)

| Component | Weight %* | Formulation 34 | Formulation 35 | Formulation 36 |
|---|---|---|---|---|
| Intragranular Phase (~94-98% of total core tablet weight) | | | | |
| Active | about 40-50 | niraparib tosylate monohydrate | | |
| Diluent 1 | about 8-14 | lactose anhydrous | | |
| Diluent 2 | about 30-40 | microcrystalline cellulose | | |
| Binder | about 1-3 | povidone | | |
| Distintegrant | about 0.1-2 | crospovidone | | |
| Glidant/Absorbant/Adsorbant | about 2-4 | silicon dioxide | | |
| Lubricant | about 0.1-2 | magnesium stearate | | |
| Extragranular Phase (~2-6 wt % of core tablet weight) | | | | |
| Distintegrant | about 0.1-2 | croscarmellose sodium | | |
| Glidant/Absorbant/Adsorbant | about 0.1-2 | silicon dioxide | | |
| Lubricant | about 0.1-2 | magnesium stearate | | |
| Total Core Tablet Weight | — | ~300-350 mg | ~350-400 mg | ~400-450 mg |

*based on total core tablet weight (sum of intragranular + extragranular phases)

In embodiments, a tablet composition is any formulation described in Table 11 comprising about 159.3 mg niraparib tosylate monohydrate. In embodiments, a tablet composition is Formulation 37. In embodiments, a tablet composition is Formulation 38. In embodiments, a tablet composition is Formulation 39.

TABLE 11

Exemplary 100 mg niraparib tablets (Formulations 35-39)

| Component | Weight %* | Formulation 37 | Formulation 38 | Formulation 39 |
|---|---|---|---|---|
| Intragranular Phase (~94-98% of total core tablet weight) | | | | |
| Active | about 40-50 | niraparib tosylate monohydrate | | |
| Diluent 1 | about 8-14 | lactose monohydrate | | |
| Diluent 2 | about 30-40 | microcrystalline cellulose | | |
| Binder | about 1-3 | povidone | | |
| Distintegrant | about 0.1-2 | crospovidone | | |
| Glidant/Absorbant/Adsorbant | about 2-4 | silicon dioxide | | |
| Extragranular Phase (~2-6 wt % of core tablet weight) | | | | |
| Distintegrant | about 0.1-2 | crospovidone | | |
| Glidant/Absorbant/Adsorbant | about 0.1-2 | silicon dioxide | | |
| Lubricant | about 0.1-2 | magnesium stearate | | |
| Total Core Tablet Weight | — | ~300-350 mg | ~350-400 mg | ~400-450 mg |

*based on total core tablet weight (sum of intragranular + extragranular phases)

In embodiments, a tablet composition is any formulation described in Table 12 comprising about 159.3 mg niraparib tosylate monohydrate. In embodiments, a tablet composition is Formulation 40. In embodiments, a tablet composition is Formulation 41. In embodiments, a tablet composition is Formulation 42.

TABLE 12

Exemplary 100 mg niraparib tablets (Formulations 40-42)

| Component | Weight %* | Formulation 40 | Formulation 41 | Formulation 42 |
|---|---|---|---|---|
| Intragranular Phase (~94-98% of total core tablet weight) | | | | |
| Active | about 40-50 | niraparib tosylate monohydrate | | |
| Diluent 1 | about 8-14 | lactose anhydrous | | |
| Diluent 2 | about 30-40 | microcrystalline cellulose | | |
| Binder | about 1-3 | povidone | | |
| Distintegrant | about 0.1-2 | crospovidone | | |
| Glidant/Absorbant/Adsorbant | about 2-4 | silicon dioxide | | |
| Extragranular Phase (~2-6 wt % of core tablet weight) | | | | |
| Distintegrant | about 0.1-2 | croscarmellose sodium | | |
| Glidant/Absorbant/Adsorbant | about 0.1-2 | silicon dioxide | | |
| Lubricant | about 0.1-2 | magnesium stearate | | |
| Total Core Tablet Weight | — | ~300-350 mg | ~350-400 mg | ~400-450 mg |

*based on total core tablet weight (sum of intragranular + extragranular phases)

In embodiments, any excipient in formulations 1-42 described herein can be varied. For example, the amount of Diluent 2 can be varied (e.g., about 7.5-15 wt % or about 9-11 wt %). Accordingly, each of Formulations 1a-42a comprise Diluent 2 in an amount that is about 7.5-15 wt % but are otherwise identical to respective Formulations 1-42. Similarly, each of Formulations 1b-42b comprise Diluent 2 in an amount that is about 9-11 wt % but are otherwise identical to respective Formulations 1-42.

In still further embodiments, any tablet composition described herein (e.g., any of formulations 1-42) further comprises a coating layer (e.g., any coating described herein).

Disintegration

Disintegration is a measure of the quality of the oral dosage forms, e.g. tablets. In general, pharmacopoeia (e.g. the US Pharmacopeia, British Pharmacopoeia, Indian Pharmacopoeia) have their own set of standards and specify disintegration tests. Pharmacopoeia of a number of international entities have been harmonized by the International conference on Harmonization (ICH) and are interchangeable. A disintegration test is performed to find out the time it takes for a solid oral dosage form to completely disintegrate. The time of disintegration can be a measure of the quality. This is because, for example, the disintegration event is the rate limiting step to the release of the active material being carried by the tablet. If the disintegration time is too slow; it means that the active ingredient may in turn be released too slowly thus possibly impacting the rate of presentation of the active to the body once ingested. Vice versa, if disintegration is too fast the reverse may be true.

A disintegration test is conducted using a disintegration apparatus. Although there are slight variations in the different pharmacopoeias, the basic construction and the working of the apparatus in general remains the same. A typical test follows. The apparatus consists of a basket made of transparent polyvinyl or other plastic material. It typically has tubes set into the same basket with equal diameter and a wire mesh made of stainless steel with uniform mesh size is fixed to each of the tubes. Small metal discs may be used to enable immersion of the dosage form completely. The entire basket-rack assembly is movable by reciprocating motor which is fixed to the apex of the basket-rack assembly. The entire assembly is immersed in a vessel containing the medium in which the disintegration test is to be carried out. The vessel is provided with a thermostat to regulate the temperature of the fluid medium to the desired temperature.

The disintegration test for each dosage form is given in a pharmacopoeia. There are some general tests for typical types of dosage forms. Some of the types of dosage forms and their disintegration tests are: (1) Uncoated tablets—the test may use distilled water as medium at 37+/−2 C at 29-32 cycles per minute; test is completed after 15 minutes. It is acceptable when there is no palpable core at the end of the cycle (for at least 5 tablets or capsules) and if the mass does not stick to the immersion disc. (2) Coated tablets—the same test procedure may be adapted but the time of operation is 30 minutes. (3) Enteric coated/Gastric resistant tablets—the test may be carried out first in distilled water (at room temperature for 5 min.; USP and no distilled water per BP and IP), then it is tested in 0.1 M HCL (up to 2 hours; BP) or Stimulated gastric fluid (1 hour; USP) followed by Phosphate buffer, pH 6.8 (1 hour; BP) or Stimulated intestinal fluid without enzymes (1 hour; USP). (4) Chewable tablets—exempted from disintegration test (BP and IP), 4 hours (USP). These are a few examples for illustration.

An exemplary disintegration test uses a standard USP <701> test apparatus. One tablet each are placed in six of the disintegration tester slots, containing a stainless steel mesh at the bottom. A magnetic sensor is placed on top of the tablets. The basket containing the slots is immersed in a controlled temperature bath of water at 37 C. The basket moves up and down in the bath between 29-32 cycles per minute. Once the tablet completely disintegrates, the sensor on top of the tablet makes contact with the mesh. The sensor automatically will record the time at which the tablet has disintegrated.

In some embodiments, the tablet has a disintegration time of about 30 seconds to about 300 seconds. In some embodiments, the tablet has a disintegration time of about 30 seconds to about 200 seconds. In some embodiments, the tablet has a disintegration time of about 30 seconds to about 150 seconds. In some embodiments, the tablet has a disintegration time of about 30 seconds, about 40 seconds, about 50 seconds, about 60 seconds, about 70 seconds, about 80 seconds, about 90 seconds, about 100 seconds, about 110 seconds, about 120 seconds, about 130 seconds, about 140 seconds, about 150 seconds, about 160 seconds, about 170 seconds, about 180 seconds, about 190 seconds, about 200 seconds, about 210 seconds, about 220 seconds, about 230 seconds, about 240 seconds, about 250 seconds, about 260 seconds, about 270 seconds, about 280 seconds, about 290 seconds, or about 300 seconds.

Stability

In some embodiments, the pharmaceutical composition disclosed herein is stable with respect to particle size distribution for at least about: 30 days, 60 days, 90 days, 6 months, 1 year, 18 months, 2 years, 3 years, 4 years, or 5 years, for example about 80%-100% such as about: 80%, 90%, 95%, or 100% of the pharmaceutical composition is stable with respect to particle size distribution. In some embodiments, the stable niraparib particles described herein in a solid oral dosage form will not show an increase in effective particle size of greater than 50% up to about 3, 6, 9, 12, 24 or 36 months storage at room temperature (about 15° C. to about 25° C.). In some embodiments, the stable niraparib particles described herein in a solid oral dosage form will not show an increase in effective particle size of greater than 60% up to about 3, 6, 9, 12, 24 or 36 months storage at room temperature (about 15° C. to about 25° C.). In some embodiments, the stable niraparib particles described herein in a solid oral dosage form will not show an increase in effective particle size of greater than 70% up to about 3, 6, 9, 12, 24 or 36 months storage at room temperature (about 15° C. to about 25° C.). In some embodiments, the stable niraparib particles described herein in a solid oral dosage form will not show an increase in effective particle size of greater than 80% up to about 3, 6, 9, 12, 24 or 36 months storage at room temperature (about 15° C. to about 25° C.). In some embodiments, the stable niraparib particles described herein in a solid oral dosage form will not show an increase in effective particle size of greater than 90% up to about 3, 6, 9, 12, 24 or 36 months storage at room temperature (about 15° C. to about 25° C.). In some embodiments, the stable niraparib particles described herein in a solid oral dosage form will not show an increase in effective particle size of greater than 95% up to about 3, 6, 9, 12, 24 or 36 months storage at room temperature (about 15° C. to about 25° C.).

In some embodiments, the stable niraparib particles described herein in a solid oral dosage form will not show an increase in effective particle size of greater than 50% up to 3, 6, 9, 12, 24 or 36 months storage at about 15° C. to 30° C., 15° C. to 40° C., or 15° C. to 50° C. In some embodiments, the stable niraparib particles described herein in a solid oral dosage form will not show an increase in effective particle size of greater than 60% up to 3, 6, 9, 12, 24 or 36 months storage at about 15° C. to 30° C., 15° C. to 40° C., or 15° C. to 50° C. In some embodiments, the stable niraparib particles described herein in a solid oral dosage form will not show an increase in effective particle size of greater than 70% up to 3, 6, 9, 12, 24 or 36 months storage at about 15° C. to 30° C., 15° C. to 40° C., or 15° C. to 50° C. In some embodiments, the stable niraparib particles described herein in a solid oral dosage form will not show an increase in effective particle size of greater than 80% up to 3, 6, 9, 12, 24 or 36 months storage at about 15° C. to 30° C., 15° C. to 40° C., or 15° C. to 50° C. In some embodiments, the stable niraparib particles described herein in a solid oral dosage form will not show an increase in effective particle size of greater than 90% up to 3, 6, 9, 12, 24 or 36 months storage at about 15° C. to 30° C., 15° C. to 40° C., or 15° C. to 50° C. In some embodiments, the stable niraparib particles described herein in a solid oral dosage form will not show an increase in effective particle size of greater than 95% up to 3, 6, 9, 12, 24 or 36 months storage at about 15° C. to 30° C., 15° C. to 40° C., or 15° C. to 50° C.

In some embodiments, the pharmaceutical composition disclosed herein is stable with respect to compound degeneration for at least about: 30 days, 60 days, 90 days, 6 months, 1 year, 18 months, 2 years, 3 years, 4 years, or 5 years, for example about 80%-100% such as about: 80%, 90%, 95%, or 100% of the active pharmaceutical agent in the pharmaceutical composition is stable. Stability may be measured by High Performance Liquid Chromatography (HPLC). In some embodiments, about 80%-100% (e.g., about: 90%-100% or 95-100%) of niraparib or a pharmaceutically acceptable salt thereof (e.g., niraparib tosylate monohydrate) in the pharmaceutical composition disclosed herein is stable for at least about: 30, 60, 90, 180, 360, 540, or 720 days, for example greater than 90 days. In some embodiments, about: 80%, 85%, 90%, 95%, or 100% (e.g., about 95%) of the niraparib or a pharmaceutically acceptable salt thereof (e.g., niraparib tosylate monohydrate) is stable with respect to compound degeneration for 30 days or more. In each case, stability may be measured by HPLC or another method known in the art. Methods for assessing the chemical storage stability of solid dosage forms are described in the literature. See, e.g., S. T. Colgan, T. J. Watson, R. D. Whipple, R. Nosal, J. V. Beaman, D. De Antonis, "The Application of Science and Risk Based Concepts to Drug Substance Stability Strategies" J. Pharm. Innov. 7:205-2013 (2012); Waterman K C, Carella A J, Gumkowski M J, et al. Improved protocol and data analysis for accelerated shelf-life estimation of solid dosage forms. Pharm Res 2007; 24(4):780-90; and S. T. Colgan, R. J. Timpano, D. Diaz, M. Roberts, R. Weaver, K. Ryan, K. Fields, G. Scrivens, Opportunities for Lean Stability Strategies" J. Pharm. Innov. 9:259-271 (2014).

In some embodiments, the pharmaceutical formulations described herein are stable with respect to compound degradation (e.g. less than 30% degradation, less than 25% degradation, less than 20% degradation, less than 15% degradation, less than 10% degradation, less than 8% degradation, less than 5% degradation, less than 3% degradation, less than 2% degradation, or less than 5% degradation) over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 3 months, at least about 4 months, at least about 5 months, at least about 6 months, at least about 7 months, at least about 8 months, at least about 9 months, at least about 10 months, at least about 11 months, at least about 12 months, at least about 24 months, or at least about 36 months under storage conditions (e.g. room temperature). In some embodiments, the formulations described herein are stable with respect to compound degradation over a period of at least about 1 week. In some embodiments, the formulations described herein are stable with respect to compound degradation over a period of at least about 1 month. In some embodiments, the formulations described herein are stable with respect to compound degradation over a period of at least about 3 months. In some embodiments, the formulations described herein are stable with respect to compound degradation over a period of at least about 6 months. In some embodiments, the formulations described herein are stable with respect to compound degradation over a period of at least about 9 months. In some embodiments, the formulations described herein are stable with respect to compound degradation over a period of at least about 12 months.

Methods for assessing the chemical stability of solid dosage forms during storage, including under accelerated aging conditions are described in the literature. See, e.g., S. T. Colgan, T. J. Watson, R. D. Whipple, R. Nosal, J. V. Beaman, D. De Antonis, "The Application of Science and Risk Based Concepts to Drug Substance Stability Strategies" J. Pharm. Innov. 7:205-2013 (2012); Waterman K C, Carella A J, Gumkowski M J, et al. Improved protocol and data analysis for accelerated shelf-life estimation of solid dosage forms. Pharm Res 2007; 24(4):780-90; and S. T. Colgan, R. J. Timpano, D. Diaz, M. Roberts, R. Weaver, K. Ryan, K. Fields, G. Scrivens, Opportunities for Lean Stability Strategies" J. Pharm. Innov. 9:259-271 (2014). Chemical stability of solid dosage forms during storage may also be dictated by the International Council for Harmonization of Technical Requirements for Pharmaceuticals for Human Use (ICH) or the World Health Organization (WHO).

Depending on the region of the world in which a pharmaceutical composition is intended to be used and/or stored, stability studies may be performed according to the climatic conditions of the country. The world is generally divided into five different zones: temperate, Mediterranean/subtropical, hot dry, hot humid/tropical zone, and hot/higher humidity. Those skilled in the relevant art may determine the appropriate conditions for testing in a specific climatic zone.

In one aspect provided herein is composition comprising a tablet comprising: an effective amount of niraparib to inhibit polyadenosine diphosphate ribose polymerase (PARP) when administered to a subject in need thereof; wherein the tablet has at least one of the following: a) the tablet comprises less than 0.2% by weight of any single niraparib degradation product; b) the tablet comprises less than 0.2% by weight of any single niraparib degradation product after storage for 1 month at 40° C. and 75% relative humidity (RH); and c) the tablet comprises less than 0.2% by weight of any single niraparib degradation product after storage for 2 months at 40° C. and 75% relative humidity (RH).

In some embodiments, the tablet comprises less than 0.2%, 0.1%, 0.09%, 0.08%, 0.07%, 0.06%, 0.05%, 0.04%, 0.03%, 0.02%, 0.01%, 0.005%, or 0.001% by weight of any single niraparib degradation product. In some embodiments, tablet comprises less than 0.2%, 0.1%, 0.09%, 0.08%, 0.07%, 0.06%, 0.05%, 0.04%, 0.03%, 0.02%, 0.01%, 0.005%, or 0.001% by weight of any single niraparib degradation product after storage for 1 month at 40° C. and 75% relative humidity (RH). In some embodiments, the tablet comprises less than 0.2%, 0.1%, 0.09%, 0.08%, 0.07%, 0.06%, 0.05%, 0.04%, 0.03%, 0.02%, 0.01%, 0.005%, or 0.001% by weight of any single niraparib degradation product after storage for 2 months at 40° C. and 75% relative humidity (RH).

In some embodiments, the tablet comprises about 0.2%, 0.1%, 0.09%, 0.08%, 0.07%, 0.06%, 0.05%, 0.04%, 0.03%, 0.02%, 0.01%, 0.005%, or 0.001% by weight of any single niraparib degradation product. In some embodiments, tablet comprises about 0.2%, 0.1%, 0.09%, 0.08%, 0.07%, 0.06%, 0.05%, 0.04%, 0.03%, 0.02%, 0.01%, 0.005%, or 0.001% by weight of any single niraparib degradation product after storage for 1 month at 40° C. and 75% relative humidity (RH). In some embodiments, the tablet comprises about 0.2%, 0.1%, 0.09%, 0.08%, 0.07%, 0.06%, 0.05%, 0.04%, 0.03%, 0.02%, 0.01%, 0.005%, or 0.001% by weight of any single niraparib degradation product after storage for 2 months at 40° C. and 75% relative humidity (RH).

In some embodiments, the invention provides an oral dosage form comprising niraparib and a pharmaceutically acceptable carrier, wherein the dosage form exhibits less than 1.5%, 1.4%, 1.3%, 1.2% 1.1%, 1.0%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01% 0.005%, or 0.001% by weight of formation of one or more degradation products, such as one or more niraparib degradation products, after storage for 1 month, 3 months, 6 months, 9 months, 12 months, 24 months, or 36 months at 5° C. In some embodiments, the invention provides an oral dosage form comprising niraparib and a pharmaceutically acceptable carrier, wherein the dosage form exhibits less than 1.5%, 1.4%, 1.3%, 1.2% 1.1%, 1.0%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01% 0.005%, or 0.001% by weight of formation of one or more degradation products, such as one or more niraparib degradation products, after storage for 1 month, 3 months, 6 months, 9 months, 12 months, 24 months, or 36 months at 25° C. and 60% relative humidity (RH). In some embodiments, the invention provides an oral dosage form comprising niraparib and a pharmaceutically acceptable carrier, wherein the dosage form exhibits less than 1.5%, 1.4%, 1.3%, 1.2% 1.1%, 1.0%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01% 0.005%, or 0.001% by weight of formation of one or more degradation products, such as one or more niraparib degradation products, after storage for 1 month, 3 months, 6 months, 9 months, 12 months, 24 months, or 36 months at 30° C. and 65% relative humidity (RH). In some embodiments, the invention provides an oral dosage form comprising niraparib and a pharmaceutically acceptable carrier, wherein the dosage form exhibits less than 1.5%, 1.4%, 1.3%, 1.2% 1.1%, 1.0%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01% 0.005%, or 0.001% by weight of formation of one or more degradation products, such as one or more niraparib degradation products, after storage for 1 month, 3 months, 6 months, 9 months, 12 months, 24 months, or 36 months at 40° C. and 75% relative humidity (RH).

In some embodiments, the amount of one or more or total impurity or degradation products of niraparib is from about 0.01 mg to 0.05 mg, 0.05 mg to 0.1 mg, 0.1 mg to 0.2 mg, 0.2 mg to 0.25 mg, 0.25 mg to 0.5 mg, 0.5 mg to 0.75 mg, 0.7 mg to 0.95 mg, 0.9 mg to 1.15 mg, 1.1 mg to 1.35 mg, 1.3 mg to 1.5 mg, 1.5 mg to 1.75 mg, 1.75 to 1.95 mg, 1.9 mg to 2.15 mg, 2.1 mg to 2.35 mg, 2.3 mg to 2.55 mg, 2.5 mg to 2.75 mg, 2.7 mg to 3.0 mg, 2.9 mg to 3.15 mg, 3.1 mg to 3.35 mg, 3.3 mg to 3.5 mg, 3.5 mg to 3.75 mg, 3.7 mg to 4.0 mg, 4.0 mg to 4.5 mg, 4.5 mg to 5.0 mg, 5.0 mg to 5.5 mg, 5.5 mg to 6.0 mg, 6.0 mg to 6.5 mg, 6.5 mg to 7.0 mg, 7.0 mg to 7.5 mg, 7.5 mg to 8.0 mg, 8.0 mg to 8.5 mg, 8.5 mg to 9.0 mg, 9.0 mg to 9.5 mg, or 9.5 mg to 10.0 mg. In some embodiments, the amount of one or more or total impurity or degradation products of niraparib is less than about or about 0.01 mg, 0.05 mg, 0.1 mg, 0.2 mg, 0.25 mg, 0.5 mg, 0.7 mg, 0.9 mg, 1.1 mg, 1.3 mg, 1.5 mg, 1.7 mg, 1.9 mg, 2. mg, 2.3 mg, 2.5 mg, 2.75 mg, 3.0 mg, 3.1 mg, 3.3 mg, 3.5 mg, 3.7 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, or 10.0 mg.

In some embodiments, the invention provides an oral dosage form comprising niraparib and a pharmaceutically acceptable carrier, wherein the dosage form exhibits less than 1.5%, 1.4%, 1.3%, 1.2% 1.1%, 1.0%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01% 0.005%, or 0.001% by weight of formation of one or more degradation products after storage for 1 month, 3 months, 6 months, 9 months, 12 months, 24 months, or 36 months at 5° C. In some embodiments, the invention provides an oral dosage form comprising niraparib and a pharmaceutically acceptable carrier, wherein the dosage form exhibits less than 1.5%, 1.4%, 1.3%, 1.2% 1.1%, 1.0%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01% 0.005%, or 0.001% by weight of formation of one or more degradation products after storage for 1 month, 3 months, 6 months, 9 months, 12 months, 24 months, or 36 months at 25° C. and 60% relative humidity (RH). In some embodiments, the invention provides an oral dosage form comprising niraparib and a pharmaceutically acceptable carrier, wherein the dosage form exhibits less than 1.5%, 1.4%, 1.3%, 1.2% 1.1%, 1.0%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01% 0.005%, or 0.001% by weight of formation of one or more degradation products after storage for 1 month, 3 months, 6 months, 9 months, 12 months, 24 months, or 36 months at 30° C. and 65% relative humidity (RH). In some embodiments, the invention provides an oral dosage form comprising niraparib and a pharmaceutically acceptable carrier, wherein the dosage form exhibits less than 1.5%, 1.4%, 1.3%, 1.2% 1.1%, 1.0%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01% 0.005%, or 0.001% by weight of formation of one or more degradation products after storage for 1 month, 3 months, 6 months, 9 months, 12 months, 24 months, or 36 months at 40° C. and 75% relative humidity (RH).

In some embodiments, the invention provides an oral dosage form comprising niraparib and a pharmaceutically acceptable carrier, wherein the dosage form exhibits less than 1.5%, 1.4%, 1.3%, 1.2% 1.1%, 1.0%, 0.9%, 0.8%, 0.7%, 0.6%, 0.5%, 0.4%, 0.3%, 0.2%, 0.1%, 0.05%, 0.025%, or 0.001% by weight of formation of any single degradation product, after storage for 1 month, 3 months, 6 months, 9 months, 12 months, 24 months, or 36 months at 5° C. In some embodiments, the invention provides an oral dosage form comprising niraparib and a pharmaceutically acceptable carrier, wherein the dosage form exhibits less than 1.5%, 1.4%, 1.3%, 1.2% 1.1%, 1.0%, 0.9%, 0.8%, 0.7%, 0.6%, 0.5%, 0.4%, 0.3%, 0.2%, 0.1%, 0.05%, 0.025%, or 0.001% by weight of formation of any single degradation product, after storage for 1 month, 3 months, 6 months, 9 months, 12 months, 24 months, or 36 months at 25° C. and 60% relative humidity (RH). In some embodiments, the invention provides an oral dosage form comprising niraparib and a pharmaceutically acceptable carrier, wherein the dosage form exhibits less than 1.5%, 1.4%, 1.3%, 1.2% 1.1%, 1.0%, 0.9%, 0.8%, 0.7%, 0.6%, 0.5%, 0.4%, 0.3%, 0.2%, 0.1%, 0.05%, 0.025%, or 0.001% by weight of formation of any single degradation product, after storage for 1 month, 3 months, 6 months, 9 months, 12 months, 24 months, or 36 months at 30° C. and 65% relative humidity (RH). In some embodiments, the invention provides an oral dosage form comprising niraparib and a pharmaceutically acceptable carrier, wherein the dosage form exhibits less than 1.5%, 1.4%, 1.3%, 1.2% 1.1%, 1.0%, 0.9%, 0.8%, 0.7%, 0.6%, 0.5%, 0.4%, 0.3%, 0.2%, 0.1%, 0.05%, 0.025%, or 0.001% by weight of formation of any single degradation product, after storage for 1 month, 3 months, 6 months, 9 months, 12 months, 24 months, or 36 months at 40° C. and 75% relative humidity (RH).

In some embodiments, the invention provides an oral dosage form comprising niraparib and a pharmaceutically acceptable carrier, wherein the dosage form exhibits less than 1.5%, 1.4%, 1.3%, 1.2% 1.1%, 1.0%, 0.9%, 0.8%, 0.7%, 0.6%, 0.5%, 0.4%, 0.3%, 0.2%, 0.1%, 0.05%, 0.025%, or 0.001% by weight of formation of total degradation products, including niraparib degradation products after storage for 1 month, 3 months, 6 months, 9 months, 12 months, 24 months, or 36 months at 5° C. In some embodiments, the invention provides an oral dosage form comprising niraparib and a pharmaceutically acceptable carrier, wherein the dosage form exhibits less than 1.5%, 1.4%, 1.3%, 1.2% 1.1%, 1.0%, 0.9%, 0.8%, 0.7%, 0.6%, 0.5%, 0.4%, 0.3%, 0.2%, 0.1%, 0.05%, 0.025%, or 0.001% by weight of formation of total degradation products, including niraparib degradation products after storage for 1 month, 3 months, 6 months, 9 months, 12 months, 24 months, or 36 months at 25° C. and 60% relative humidity (RH). In some embodiments, the invention provides an oral dosage form comprising niraparib and a pharmaceutically acceptable carrier, wherein the dosage form exhibits less than 1.5%, 1.4%, 1.3%, 1.2% 1.1%, 1.0%, 0.9%, 0.8%, 0.7%, 0.6%, 0.5%, 0.4%, 0.3%, 0.2%, 0.1%, 0.05%, 0.025%, or 0.001% by weight of formation of total degradation products, including total niraparib degradation products after storage for 1 month, 3 months, 6 months, 9 months, 12 months, 24 months, or 36 months at 30° C. and 65% relative humidity (RH). In some embodiments, the invention provides an oral dosage form comprising niraparib and a pharmaceutically acceptable carrier, wherein the dosage form exhibits less than 1.5%, 1.4%, 1.3%, 1.2% 1.1%, 1.0%, 0.9%, 0.8%, 0.7%, 0.6%, 0.5%, 0.4%, 0.3%, 0.2%, 0.1%, 0.05%, 0.025%, or 0.001% by weight of formation of total degradation products, including niraparib degradation products after storage for 1 month, 3 months, 6 months, 9 months, 12 months, 24 months, or 36 months at 40° C. and 70% relative humidity (RH).

In some embodiments, the composition comprises less than 10% by weight of water. In some embodiments, the composition comprises less than 10% by weight of water after storage for 1 month at 40° C. and 75% relative humidity (RH). In some embodiments, the composition comprises less than 10% by weight of water after storage for 2 months at 40° C. and 75% relative humidity (RH).

In some embodiments, the composition comprises less than 30%, 25%, 20%, 15%, 10%, 9%, 8%, 7%, 6%, 5%, 4%, 3%, 2%, 1%, 0.5%, or 0.1% by weight of water. In some embodiments, the composition comprises about 30%, 25%, 20%, 15%, 10%, 9%, 8%, 7%, 6%, 5%, 4%, 3%, 2%, 1%, 0.5%, or 0.1% by weight of water. In some embodiments, the composition comprises less than 30%, 25%, 20%, 15%, 10%, 9%, 8%, 7%, 6%, 5%, 4%, 3%, 2%, 1%, 0.5%, or 0.1% by weight of water after storage for 1 month at 40° C. and 75% relative humidity (RH). In some embodiments, the composition comprises about 30%, 25%, 20%, 15%, 10%, 9%, 8%, 7%, 6%, 5%, 4%, 3%, 2%, 1%, 0.5%, or 0.1% by weight of water after storage for 1 month at 40° C. and 75% relative humidity (RH). In some embodiments, the composition comprises less than 30%, 25%, 20%, 15%, 10%, 9%, 8%, 7%, 6%, 5%, 4%, 3%, 2%, 1%, 0.5%, 0.1% by weight of water after storage for 2 months at 40° C. and 75% relative humidity (RH). In some embodiments, the composition comprises about 30%, 25%, 20%, 15%, 10%, 9%, 8%, 7%, 6%, 5%, 4%, 3%, 2%, 1%, 0.5%, or 0.1% by weight of water after storage for 2 months at 40° C. and 75% relative humidity (RH). In some embodiments, the composition comprises less than 30%, 25%, 20%, 15%, 10%, 9%, 8%, 7%, 6%, 5%, 4%, 3%, 2%, 1%, 0.5%, or 0.1% by weight of water after storage for 3 months, 6 months, 9 months, 12 months, 24 months, or 36 months at 40° C. and 75% relative humidity (RH). In some embodiments, the composition comprises about 30%, 25%, 20%, 15%, 10%, 9%, 8%, 7%, 6%, 5%, 4%, 3%, 2%, 1%, 0.5%, or 0.1% by weight of water after storage for 3 months, 6 months, 9 months, 12 months, 24 months, or 36 months at 40° C. and 75% relative humidity (RH).

Tablets

In some embodiments, the pharmaceutical composition is formulated into solid oral pharmaceutical dosage forms. Solid oral pharmaceutical dosage forms include, but are not limited to, tablets, capsules, powders, granules and sachets. For example, the solid oral pharmaceutical dosage form can be a tablet.

In some embodiments, a therapeutically effective amount of niraparib or a pharmaceutically acceptable salt thereof administered to a subject via a solid dosage form is in the range of about 1 mg to about 2000 mg. In some embodiments, a therapeutically effective amount of niraparib or a pharmaceutically acceptable salt thereof administered to a subject via a solid dosage form is in the range of about 1 mg to about 1000 mg. In some embodiments, a therapeutically effective amount of niraparib or a pharmaceutically acceptable salt thereof administered to a subject via a solid dosage form is in the range of from about 50 mg to about 300 mg. In some embodiments, a niraparib formulation is administered as a solid dosage form at a concentration of about 50 mg to about 100 mg. In some embodiments, the niraparib formulation is administered as a solid dosage form at concentration of about 100 mg to about 300 mg. For example, a therapeutically effective amount of niraparib or a pharmaceutically acceptable salt thereof administered to a subject via a solid dosage form can be from about 1 mg to 5 mg, 5 mg to 10 mg, 10 mg to 20 mg, 20 mg to 25 mg, 35 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, or 950 mg to 1000 mg, 1000 mg to 1050 mg, 1050 mg to 1100 mg, 1100 mg to 1150 mg, 1150 mg to 1200 mg, 1200 mg to 1250 mg, 1250 mg to 1300 mg, 1300 mg to 1350 mg, 1350 mg to 1400 mg, 1400 mg to 1450 mg, 1450 mg to 1500 mg, 1500 mg to 1550 mg, 1550 mg to 1600 mg, 1600 mg to 1650 mg, 1650 mg to 1700 mg, 1700 mg to 1750 mg, 1750 mg to 1800 mg, 1800 mg to 1850 mg, 1850 mg to 1900 mg, 1900 mg to 1950 mg, or 1950 mg to 2000 mg. For example, a therapeutically effective amount of niraparib tosylate monohydrate administered to a subject via a solid dosage form can be from about 1 mg to about 2000 mg, for example, from about 1 mg to 5 mg, 5 mg to 10 mg, 10 mg to 20 mg, 20 mg to 25 mg, 35 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, 950 mg to 1000 mg, 1000 mg to 1050 mg, 1050 mg to 1100 mg, 1100 mg to 1150 mg, 1150 mg to 1200 mg, 1200 mg to 1250 mg, 1250 mg to 1300 mg, 1300 mg to 1350 mg, 1350 mg to 1400 mg, 1400 mg to 1450 mg, 1450 mg to 1500 mg, 1500 mg to 1550 mg, 1550 mg to 1600 mg, 1600 mg to 1650 mg, 1650 mg to 1700 mg, 1700 mg to 1750 mg, 1750 mg to 1800 mg, 1800 mg to 1850 mg, 1850 mg to 1900 mg, 1900 mg to 1950 mg, or 1950 mg to 2000 mg. In some aspects, the solid oral dosage form can be administered one (s.i.d.), two (b.i.d.), or three times a day (t.i.d.).

For example, a therapeutically effective amount of niraparib or a pharmaceutically acceptable salt thereof administered to a subject via a solid dosage form can be from about 1 mg to 5 mg, 5 mg to 10 mg, 10 mg to 20 mg, 20 mg to 25 mg, 25 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, 950 mg to 1000 mg, 1000 mg to 1050 mg, 1050 mg to 1100 mg, 1100 mg to 1150 mg, 1150 mg to 1200 mg, 1200 mg to 1250 mg, 1250 mg to 1300 mg, 1300 mg to 1350 mg, 1350 mg to 1400 mg, 1400 mg to 1450 mg, 1450 mg to 1500 mg, 1500 mg to 1550 mg, 1550 mg to 1600 mg, 1600 mg to 1650 mg, 1650 mg to 1700 mg, 1700 mg to 1750 mg, 1750 mg to 1800 mg, 1800 mg to 1850 mg, 1850 mg to 1900 mg, 1900 mg to 1950 mg, or 1950 mg to 2000 mg. In some aspects, the solid oral dosage form can be administered one (s.i.d.), two (b.i.d.), or three times a day (t.i.d.).

For example, a therapeutically effective amount of niraparib or a pharmaceutically acceptable salt thereof administered to a subject via a solid dosage form can be about 1 mg to 5 mg, 5 mg to 10 mg, 10 mg to 20 mg, 20 mg to 25 mg, 25 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, 950 mg to 1000 mg, 1000 mg to 1050 mg, 1050 mg to 1100 mg, 1100 mg to 1150 mg, 1150 mg to 1200 mg, 1200 mg to 1250 mg, 1250 mg to 1300 mg, 1300 mg to 1350 mg, 1350 mg to 1400 mg, 1400 mg to 1450 mg, 1450 mg to 1500 mg, 1500 mg to 1550 mg, 1550 mg to 1600 mg, 1600 mg to 1650 mg, 1650 mg to 1700 mg, 1700 mg to 1750 mg, 1750 mg to 1800 mg, 1800 mg to 1850 mg, 1850 mg to 1900 mg, 1900 mg to 1950 mg, or 1950 mg to 2000 mg. For example, a therapeutically effective amount of niraparib tosylate monohydrate administered to a subject via a solid dosage form can be about 1 mg to 5 mg, 5 mg to 10 mg, 10 mg to 20 mg, 20 mg to 25 mg, 35 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, 950 mg to 1000 mg, 1000 mg to 1050 mg, 1050 mg to 1100 mg, 1100 mg to 1150 mg, 1150 mg to 1200 mg, 1200 mg to 1250 mg, 1250 mg to 1300 mg, 1300 mg to 1350 mg, 1350 mg to 1400 mg, 1400 mg to 1450 mg, 1450 mg to 1500 mg, 1500 mg to 1550 mg, 1550 mg to 1600 mg, 1600 mg to 1650 mg, 1650 mg to 1700 mg, 1700 mg to 1750 mg, 1750 mg to 1800 mg, 1800 mg to 1850 mg, 1850 mg to 1900 mg, 1900 mg to 1950 mg, or 1950 mg to 2000 mg. In some embodiments, a therapeutically effective amount of niraparib tosylate monohydrate administered to a subject via a solid dosage form is about 79.7 mg. In some embodiments, a therapeutically effective amount of niraparib tosylate monohydrate administered to a subject via a solid dosage form is about 159.4 mg. In some embodiments, a therapeutically effective amount of niraparib tosylate monohydrate administered to a subject via a solid dosage form is about 318.8 mg. In some embodiments, a therapeutically effective amount of niraparib tosylate monohydrate administered to a subject via a solid dosage form is about 478.0 mg. In some aspects, the solid oral dosage form can be administered one (s.i.d.), two (b.i.d.), or three times a day (t.i.d.).

Contemplated compositions of the present invention provide a therapeutically effective amount of niraparib or a pharmaceutically acceptable salt thereof over an interval of about 30 minutes to about 8 hours after administration, enabling, for example, once-a-day, twice-a-day, three times a day, and etc. administration if desired.

In some embodiments, the tablet is formed using materials which include, but are not limited to, natural or synthetic gelatin, pectin, casein, collagen, protein, modified starch, polyvinylpyrrolidone, acrylic polymers, cellulose derivatives, or combinations thereof. In some embodiments, the tablet is formed using preservatives, coloring and opacifying agents, flavorings and sweeteners, sugars, gastroresistant substances, or combinations thereof. In some embodiments, the tablet is coated. In some embodiments, the coating covering the tablet includes, but is not limited to, immediate release coatings, protective coatings, enteric or delayed release coatings, sustained release coatings, barrier coatings, seal coatings, or combinations thereof. The term "coating" means a process by which an outer layer of coating material is applied to the surface of a dosage form in order to confer specific benefits over uncoated variety. It involves application of a coat, including sugar or polymeric coats, on the dosage form. The advantages of tablet coating are taste masking, odor masking, physical and chemical protection, protection of the drug in the stomach, and to control its release profile. Coating may be applied to a wide range of oral solid dosage form, such as particles, powders, granules, crystals, pellets and tablets. When coating composition is applied to a batch of tablets in a coating pan, the tablet surfaces become covered with a polymeric film.

Film Coatings

In some embodiments, the tablets may further comprise an optional film coating. In some embodiments, the film coating comprises water-soluble polymer(s) and does not affect the immediate release or tamper resistant properties of the composition.

In some embodiments, the film coating comprises a polymer, pigment, plasticizer, flavors, surfactants, adhesion enhancers, vehicle(s) and any combination thereof. In some embodiments, the film coating comprises a polymer, pigment and a plasticizer.

In some embodiments, the film coating comprises a saccharide, polydextrose, maltodextrin, lactose, waxes, cellulose derivatives, cellulose ethers, acrylic polymers and copolymers, polyethylene glycols, polyvinyl pyrrolidone, polyvinyl alcohol, hydroxyethylcellulose, hydroxypropylcellulose, hydroxypropylmethylcellulose, methylcellulose and any combination thereof. In some embodiments, the film coating comprises polyethylene glycol, polyvinyl pyrrolidone, polyvinyl alcohol and any combination thereof.

In some embodiments, the film coating comprises polyols such as glycerol, propylene glycol, macrogols, organic esters such as phthalate esters, dibutyl sebacetate, citrate esters, triacetin, oils/glycerides such as castor oil, acetylated monoglycerides, fractionated coconut oil and any combination thereof.

In some embodiments, the film coating comprises polyvinyl alcohol, titanium dioxide, polyethylene glycol, talc, ferrosoferric oxide and any combination thereof.

In some embodiments, the film coating comprises polyvinyl alcohol, titanium dioxide, polyethylene glycol, talc, FD&C Blue #2/Indigo Carmine Aluminum Lake and any combination thereof.

In some embodiments, the film coating comprises polyvinyl alcohol, titanium dioxide, polyethylene glycol, talc, FD&C Blue #1/Brilliant Blue FCF Aluminum Lake and any combination thereof.

In some embodiments, the film coating comprises organic dyes and their lakes, inorganic colors, natural colors and any combination thereof.

In some embodiments, the film coating comprises, Opadry®, Opadry® II, Opadry® QX, Opadry® SGR, Opadry® AMB, Opadry® fx™, Opadry® ns-g, Opadry® NS, Opadry® tm, Opalux®, Opadry® EZ and any combination thereof.

In some embodiments, the film coating comprises a dispersion prepared using different solvents such as water, alcohols, ketones, esters, chlorinated hydrocarbons and any combination thereof. In some embodiments, the dispersion comprises water and alcohols. In some embodiments, the dispersion comprises water.

In some embodiments, the film coating comprises Opadry® II. In some embodiments, the Opadry® II is present in an amount of about 0.1% to about 10% by weight. In some embodiments, the Opadry® II is present in an amount of about 0.1% to about 5% by weight. In some embodiments, the Opadry® II is present in an amount of about 0.1%, about 0.2%, about 0.3%, about 0.4%, about 0.5%, about 0.6, about 0.7%, about 0.8%, about 0.9%, about 1%, about 1.5%, about 2%, about 2.5%, about 3%, about 3.5%, about 4%, about 4.5%, or about 5% by weight.

In some embodiments, the tablet is broken such that the particulates are sprinkled on soft foods and swallowed without chewing. In some embodiments, the shape and size of the tablet also vary. In some embodiments, the pharmaceutical composition disclosed herein (e.g., tablet) is swallowed as a whole. In some embodiments, the pharmaceutical composition disclosed herein is not a film. In some embodiments, the pharmaceutical composition disclosed herein is not for buccal administration. In some embodiments, the pharmaceutical composition disclosed herein (e.g., tablet) dissolves in stomach or intestine.

In one aspect provided herein is a composition comprising a tablet comprising: an effective amount of niraparib to inhibit polyadenosine diphosphate ribose polymerase (PARP) when administered to a subject in need thereof; wherein the tablet has at least one of the following: a) a net weight of at least 200, 500, or 800 mg; b) a thickness of at least 4.0 mm; and c) a friability of less than 2%; wherein the effective amount of niraparib is from about 50 mg to about 350 mg based on the niraparib free base.

In some embodiments, the effective amount of niraparib is from about 75 mg to about 125 mg based on the niraparib free base. In some embodiments, the effective amount of niraparib is about 50 mg, about 100 mg, or about 150 mg based on the niraparib free base. In some embodiments, the effective amount of niraparib is about 100 mg based on the niraparib free base.

In some embodiments, the tablet disclosed herein has a net weight of at least 200 mg, at least 210 mg, at least 220 mg, at least 230 mg, at least 240 mg, at least 250 mg, at least 260 mg, at least 270 mg, at least 280 mg, at least 290 mg, at least 300 mg, at least 310 mg, at least 320 mg, at least 330 mg, at least 340 mg, at least 350 mg, at least 360 mg, at least 370 mg, at least 380 mg, at least 390 mg, at least 400 mg, at least 410 mg, at least 420 mg, at least 430 mg, at least 440 mg, at least 450 mg, at least 460 mg, at least 470 mg, at least 480 mg, at least 490 mg, or at least 500 mg. In some embodiments, the tablet disclosed herein has a net weight of at least 300 mg.

In some embodiments, the effective amount of niraparib is from about 175 mg to about 225 mg based on the niraparib free base. In some embodiments, the effective amount of niraparib is about 150 mg, about 200 mg, or about 250 mg based on the niraparib free base. In some embodiments, the effective amount of niraparib is about 200 mg based on the niraparib free base.

In some embodiments, the tablet disclosed herein has a net weight of at least 500 mg, at least 510 mg, at least 520 mg, at least 530 mg, at least 540 mg, at least 550 mg, at least 560 mg, at least 570 mg, at least 580 mg, at least 590 mg, at least 600 mg, at least 610 mg, at least 620 mg, at least 630 mg, at least 640 mg, at least 650 mg, at least 660 mg, at least 670 mg, at least 680 mg, at least 690 mg, at least 700 mg, at least 710 mg, at least 720 mg, at least 730 mg, at least 740 mg, at least 750 mg, at least 760 mg, at least 770 mg, at least 780 mg, at least 790 mg, or at least 800 mg. In some embodiments, the tablet has a net weight of at least 600 mg.

In some embodiments, the effective amount of niraparib is from about 275 mg to about 325 mg based on the niraparib free base. In some embodiments, the effective amount of niraparib is about 250 mg, about 300 mg, or about 350 mg based on the niraparib free base. In some embodiments, the effective amount of niraparib is about 300 mg based on the niraparib free base.

In some embodiments, the tablet disclosed herein has a net weight of at least 800 mg, at least 810 mg, at least 820 mg, at least 830 mg, at least 840 mg, at least 850 mg, at least 860 mg, at least 870 mg, at least 880 mg, at least 890 mg, at least 900 mg, at least 910 mg, at least 920 mg, at least 930 mg, at least 940 mg, at least 950 mg, at least 960 mg, at least 970 mg, at least 980 mg, at least 990 mg, at least 1000 mg, at least 1010 mg, at least 1020 mg, at least 1030 mg, at least 1040 mg, at least 1050 mg, at least 1060 mg, at least 1070 mg, at least 1080 mg, at least 1090 mg, at least 1100 mg, at least 1110 mg, at least 1120 mg, at least 1130 mg, at least 1140 mg, at least 1150 mg, at least 1160 mg, at least 1170 mg, at least 1180 mg, at least 1190 mg, or at least 1200 mg.

In some embodiments, the tablet disclosed herein has a net weight of about 900 mg, about 910 mg, about 920 mg, about 930 mg, about 940 mg, about 950 mg, about 960 mg, about 970 mg, about 980 mg, about 990 mg, about 1000 mg, about 1010 mg, about 1020 mg, about 1030 mg, about 1040 mg, about 1050 mg, about 1060 mg, about 1070 mg, about 1080 mg, about 1090 mg, about 1100 mg, about 1110 mg, about 1120 mg, about 1130 mg, about 1140 mg, about 1150 mg, about 1160 mg, about 1170 mg, about 1180 mg, about 1190 mg, or about 1200 mg. In some embodiments, the tablet has a net weight of at least 1000.

In some embodiments, the tablet disclosed herein has a thickness of at least 4.0 mm, at least 4.1 mm, at least 4.2 mm, at least 4.3 mm, at least 4.4 mm, at least 4.5 mm, at least 4.6 mm, at least 4.7 mm, at least 4.8 mm, at least 4.9 mm, at least 5.0 mm, at least 5.1 mm, at least 5.2 mm, at least 5.3 mm, at least 5.4 mm, at least 5.5 mm, at least 5.6 mm, at least 5.7 mm, at least 5.8 mm, at least 5.9 mm, at least 6.0 mm, at least 6.1 mm, at least 6.2 mm, at least 6.3 mm, at least 6.4 mm, at least 6.5 mm, at least 6.6 mm, at least 6.7 mm, at least 6.8, at least 6.9 mm, at least 7.0 mm, at least 7.1 mm, at least 7.2 mm, at least 7.3 mm, at least 7.4 mm, at least 7.5 mm, at least 7.6 mm, at least 7.7 mm, at least 7.8 mm, at least 7.9 mm, at least 8.0 mm, at least 8.5 mm, at least 9.0 mm, at least 9.5 mm, or at least 10 mm. In some embodiments, the tablet disclosed herein has a thickness of about 4.5 mm, about 4.6 mm, about 4.7 mm, about 4.8 mm, about 4.9 mm, about 5.0 mm, about 5.1 mm, about 5.2 mm, about 5.3 mm, about 5.4 mm, about 5.5 mm, about 5.6 mm, about 5.7 mm, about 5.8 mm, about 5.9 mm, about 6.0 mm, about 6.1 mm, about 6.2 mm, about 6.3 mm, about 6.4 mm, about 6.5 mm, about 6.6 mm, about 6.7 mm, about 6.8, about 6.9 mm, about 7.0 mm, about 7.1 mm, about 7.2 mm, about 7.3 mm, about 7.4 mm, about 7.5 mm, about 7.6 mm, about 7.7 mm, about 7.8 mm, about 7.9 mm, about 8.0 mm, about 8.5 mm, about 9.0 mm, about 9.5 mm, or about 10 mm.

In some embodiments, the tablet disclosed herein has a friability of less than 2%, less than 1.9%, less than 1.8%, less than 1.7%, less than 1.6%, less than 1.5%, less than 1.4%, less than 1.3%, less than 1.2%, less than 1.1%, less than 1.0%, less than 0.9%, less than 0.8%, less than 0.7%, less than 0.6%, less than 0.5%, less than 0.4%, less than 0.3%, less than 0.2%, or less than 0.1%.

In some embodiments, a tablet disclosed herein has a net weight ranging from about 1 mg to 5 mg, 5 mg to 10 mg, 10 mg to 20 mg, 20 mg to 25 mg, 35 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, 950 mg to 1000 mg, 1000 mg to 1050 mg, 1050 mg to 1100 mg, 1100 mg to 1150 mg, 1150 mg to 1200 mg, 1200 mg to 1250 mg, 1250 mg to 1300 mg, 1300 mg to 1350 mg, 1350 mg to 1400 mg, 1400 mg to 1450 mg, 1450 mg to 1500 mg, 1500 mg to 1550 mg, 1550 mg to 1600 mg, 1600 mg to 1650 mg, 1650 mg to 1700 mg, 1700 mg to 1750 mg, 1750 mg to 1800 mg, 1800 mg to 1850 mg, 1850 mg to 1900 mg, 1900 mg to 1950 mg, or 1950 mg to 2000 mg. For example, a tablet disclosed herein can have a net weight ranging from about 50 mg to 150 mg, from about 75 mg to about 125 mg, about 90 mg to about 110 mg, about 93 mg to about 107 mg, about 94 mg to about 106 mg, or about 95 mg to about 105 mg. In other instances, a tablet disclosed herein has a net weight ranging from about 850 mg to 900 mg, from about 900 mg to about 950 mg, from about 950 mg to 1000 mg, from about 1000 mg to about 1050 mg, from about 1050 mg to about 1100 mg, from about 1100 mg to 1150 mg, from about 1150 mg to 1200 mg, from about 1200 mg to 1250 mg, from about 1250 mg to 1300 mg, from about 1300 mg to 1350 mg, from about 1350 mg to 1400 mg, from about 1400 mg to 1450 mg, from about 1450 mg to 1500 mg, from about 1500 mg to 1550 mg, from about 1550 mg to 1600 mg, from about 1600 mg to 1650 mg, from about 1650 mg to 1700 mg, from about 1700 to about 1750 mg, from about 1750 mg to 1800 mg, from about 1800 mg to about 1850 mg, from about 1850 mg to 1900 mg, from about 1900 mg to about 1950 mg, or from about 1950 mg to 2000 mg.

In some embodiments, a tablet disclosed herein has a net weight of about 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, or 2000 mg. For example, a tablet disclosed herein can have a net weight of about 100 mg, about 98 mg, about 96 mg, about 94 mg, about 92 mg, about 90 mg, about 80 mg, about 70 mg, about 60 mg, or about 50 mg. In other instances, a tablet disclosed herein has a net weight ranging from about 1050 mg, 1040 mg, 1030 mg, 1020 mg, 1010 mg, about 1000 mg, about 990 mg, about 980 mg, about 970 mg, about 960 mg, about 950 mg, or about 940 mg.

In some embodiments, the niraparib comprises niraparib free base or a pharmaceutically acceptable salt thereof. In some embodiments, the pharmaceutically acceptable salt of niraparib is niraparib tosylate.

The method can comprise administration of a niraparib composition in 1, 2, 3, or 4 tablets once, twice, or three times daily; for example 1 or 2 or 3 tablets.

In some embodiments, the weight ratio of an active pharmaceutical ingredient (e.g., niraparib or a pharmaceutically acceptable salt thereof such as niraparib tosylate monohydrate) to a non-active pharmaceutical ingredient (e.g., lactose monohydrate, lactose anhydrous, mannitol, or calcium phosphate dibasic) is from about 1:10 to about 10:1, respectively, for example about 1:2, about 1:3, about 1:4, about 1:5, about 1:6, about 1:7, about 1:8, about 1:9, about 1:10, about 10:1, about 9:1, about 8:1, about 7:1, about 6:1, about 5:1, about 4:1, about 3:1, or about 2:1. In some embodiments, the weight ratio of an active pharmaceutical ingredient (e.g., niraparib or a pharmaceutically acceptable salt thereof such as niraparib tosylate monohydrate) to a non-active pharmaceutical ingredient (e.g., microcrystalline cellulose, starch, polyethylene oxide, or hydroxypropyl methylcellulose (HPMC)) is from about 1:10 to about 10:1, respectively, for example about 1:2, about 1:3, about 1:4, about 1:5, about 1:6, about 1:7, about 1:8, about 1:9, about 1:10, about 10:1, about 9:1, about 8:1, about 7:1, about 6:1, about 5:1, about 4:1, about 3:1, or about 2:1. In some embodiments, the weight ratio of an active pharmaceutical ingredient (e.g., niraparib or a pharmaceutically acceptable salt thereof such as niraparib tosylate monohydrate) to a non-active pharmaceutical ingredient (e.g., povidone, hydroxylpropyl cellulose, or hydroxypropyl methylcellulose) is from about 10:1 to about 100:1, respectively, for example about 10:1, about 20:1, about 30:1, about 40:1, about 50:1, about 60:1, about 70:1, about 80:1, or about 90:1. In some embodiments, the weight ratio of an active pharmaceutical ingredient (e.g., niraparib or a pharmaceutically acceptable salt thereof such as niraparib tosylate monohydrate) to a non-active pharmaceutical ingredient (e.g., magnesium stearate) is from about 10:1 to about 100:1, respectively, for example about 10:1, about 20:1, about 30:1, about 40:1, about 50:1, about 60:1, about 70:1, about 80:1, or about 90:1. In some embodiments, the weight ratio of a non-active pharmaceutical ingredient to an active pharmaceutical ingredient (e.g., niraparib or a pharmaceutically acceptable salt thereof such as niraparib tosylate monohydrate) to is from about 3:2 to about 11:1, from about 3:1 to about 7:1, from about 1:1 to about 5:1, from about 9:2 to about 11:2, from about 4:2 to about 6:2, about 5:1, or about 2.5:1. In some embodiments, the weight ratio of an active pharmaceutical ingredient (e.g., niraparib or a pharmaceutically acceptable salt thereof such as niraparib tosylate monohydrate) to a non-active pharmaceutical ingredient is about 1:1.6. In some embodiments, the weight ratio of an active pharmaceutical ingredient (e.g., niraparib or a pharmaceutically acceptable salt thereof such as niraparib tosylate monohydrate) to a non-active pharmaceutical ingredient is about 1:2. In some embodiments, the weight ratio of an active pharmaceutical ingredient (e.g., niraparib or a pharmaceutically acceptable salt thereof such as niraparib tosylate monohydrate) to a non-active pharmaceutical ingredient is about 1:1.1. In some embodiments, the weight ratio of an active pharmaceutical ingredient (e.g., niraparib or a pharmaceutically acceptable salt thereof such as niraparib tosylate monohydrate) to a non-active pharmaceutical ingredient is about 1:1. In some embodiments, the weight ratio of niraparib or a pharmaceutically acceptable salt thereof such as niraparib tosylate monohydrate to lactose monohydrate is about 48:20, for example, 47.8:20.4 In some embodiments, the weight ratio of niraparib or a pharmaceutically acceptable salt thereof such as niraparib tosylate monohydrate to lactose monohydrate is about 48:19, for example, 47.8:19.4. In some embodiments, the weight ratio of niraparib or a pharmaceutically acceptable salt thereof such as niraparib tosylate monohydrate to lactose monohydrate is about 48:18, for example, 47.8:17.9. In some embodiments, the weight ratio of niraparib or a pharmaceutically acceptable salt thereof such as niraparib tosylate monohydrate to magnesium stearate is about 48:1, for example, 47.8:1.

In some embodiments, the weight ratio of a first non-active pharmaceutical ingredient to a second non-active pharmaceutical ingredient is from about 1:1 to about 200:1, respectively, for example about 1:1, about 2:1, about 3:1, about 4:1, about 5:1, about 10:1, about 15:1, about 20:1, about 25:1, about 30:1, about 40:1, about 50:1, about 60:1, about 70:1, about 75:1, about 80:1, about 90:1, about 100:1, about 110:1, about 120:1, about 130:1, about 140:1, about 150:1, about 160:1, about 170:1, about 180:1, about 190:1, or about 200:1. In some embodiments, the weight ratio of lactose monohydrate to magnesium stearate is about 120:1 to about 125:1. In some embodiments, the weight ratio of lactose monohydrate to magnesium stearate is about 122.36:1. In some embodiments, the weight ratio of lactose monohydrate to magnesium stearate is about 20:1. In some embodiments, the weight ratio of lactose monohydrate to magnesium stearate is about 10:1

Indications Suitable for Treatment

Any subject having cancer, including breast cancer, ovarian cancer, cervical cancer, epithelial ovarian cancer, fallopian tube cancer, primary peritoneal cancer, endometrial cancer, prostate cancer, testicular cancer, pancreatic cancer, esophageal cancer, head and neck cancer, gastric cancer, bladder cancer, lung cancer (e.g., adenocarcinoma, NSCLC and SCLC), bone cancer (e.g., osteosarcoma), colon cancer, rectal cancer, thyroid cancer, brain and central nervous system cancers, glioblastoma, neuroblastoma, neuroendocrine cancer, rhabdoid cancer, keratoacanthoma, epidermoid carcinoma, seminoma, melanoma, sarcoma (e.g., liposarcoma), bladder cancer, liver cancer (e.g., hepatocellular carcinoma), kidney cancer (e.g., renal cell carcinoma), myeloid disorders (e.g., AML, CML, myelodysplastic syndrome and promyelocytic leukemia), and lymphoid disorders (e.g., leukemia, multiple myeloma, mantle cell lymphoma, ALL, CLL, B-cell lymphoma, T-cell lymphoma, Hodgkin's lymphoma, non-Hodgkin's lymphoma, hairy cell lymphoma) may be treated with compounds and methods described herein.

In some embodiments, the methods of the invention treat subjects with ovarian cancer. In some embodiments, the methods of the invention treat subjects with epithelial ovarian cancer. In some embodiments, the methods of the invention treat subjects with fallopian tube cancer. In some embodiments, the methods of the invention treat subjects with primary peritoneal cancer.

In some embodiments, the methods of the invention treat subjects with recurrent ovarian cancer. In some embodiments, the methods of the invention treat subjects with recurrent epithelial ovarian cancer. In some embodiments, the methods of the invention treat subjects with recurrent fallopian tube cancer. In some embodiments, the methods of the invention treat subjects with recurrent primary peritoneal cancer.

In some embodiments, the methods of the invention treat subjects with recurrent ovarian cancer following a complete or partial response to a chemotherapy, such as a platinum-based chemotherapy. In some embodiments, the methods of the invention treat subjects with recurrent epithelial ovarian cancer following a complete or partial response to a chemotherapy, such as a platinum-based chemotherapy. In some embodiments, the methods of the invention treat subjects with recurrent fallopian tube cancer following a complete or partial response to a chemotherapy, such as a platinum-based chemotherapy. In some embodiments, the methods of the invention treat subjects with recurrent primary peritoneal cancer following a complete or partial response to a chemotherapy, such as a platinum-based chemotherapy.

In some embodiments, the methods of the invention treat subjects with recurrent ovarian cancer, recurrent epithelial ovarian cancer, recurrent fallopian tube cancer and/or recurrent primary peritoneal cancer following a complete or partial response to a platinum-based chemotherapy, wherein the subjects begin the treatment no later than 8 weeks after their most recent platinum-containing regimen. For example, subjects can begin treatment with niraparib about 7 weeks after their most recent platinum-containing regimen. For example, subjects can begin treatment with niraparib about 6 weeks after their most recent platinum-containing regimen. For example, subjects can begin treatment with niraparib about 6 weeks after their most recent platinum-containing regimen. For example, subjects can begin treatment with niraparib about 5 weeks after their most recent platinum-containing regimen. For example, subjects can begin treatment with niraparib about 4 weeks after their most recent platinum-containing regimen. For example, subjects can begin treatment with niraparib about 3 weeks after their most recent platinum-containing regimen. For example, subjects can begin treatment with niraparib about 2 weeks after their most recent platinum-containing regimen. For example, subjects can begin treatment with niraparib about 1 week after their most recent platinum-containing regimen.

In some embodiments, the methods of the invention treat subjects with prostate cancer.

In some embodiments, the methods of the invention treat subjects with a pediatric cancer. Exemplary pediatric cancers include, but are not limited to adrenocortical carcinoma, astrocytoma, atypical teratoid rhabdoid tumor, brain tumors, chondroblastoma, choroid plexus tumor, craniopharyngioma, desmoid tumor, dysembryplastic neuroepithelial tumor (DNT), ependymoma, fibrosarcoma, germ cell tumor of the brain, glioblastoma multiforme, diffuse pontine glioma, low grade glioma, gliomatosis cerebri, hepatoblastoma, histiocytosis, kidney tumor, acute lymphoblastic leukemia (ALL), acute myeloid leukemia (AML), chronic myelogenous leukemia (CML), liposarcoma, liver cancer, Burkitt lymphoma, Hodgkin lymphoma, non-Hodgkin lymphoma, malignant fibrous histiocytoma, melanoma, myelodysplastic syndrome, nephroblastoma, neuroblastoma, neurofibrosarcoma, osteosarcoma, pilocytic astrocytoma, retinoblastoma, rhabdoid tumor of the kidney, rhabdomyosarcoma, Ewing sarcoma, soft tissue sarcoma, synovial sarcoma, spinal cord tumor and Wilm's tumor.

In some embodiments, the methods of the invention treat subjects with a cancer with a dosage of 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, or 2000 mg of niraparib or pharmaceutically acceptable salt thereof once-daily, twice-daily, or thrice-daily. In some embodiments, the methods of the invention treat subjects with a cancer with a dosage of 150 mg to 175 mg, 170 mg to 195 mg, 190 mg to 215 mg, 210 mg to 235 mg, 230 mg to 255 mg, 250 mg to 275 mg, 270 to 295 mg, 290 mg to 315 mg, 310 mg to 335 mg, 330 mg to 355 mg, 350 mg to 375 mg, or 370 mg to 400 mg of niraparib or pharmaceutically acceptable salt thereof once-daily, twice-daily, or thrice-daily. In some embodiments, the methods of the invention treat subjects with a cancer with a dosage of 5 mg, 7.5 mg, 10 mg, 12.5 mg, 15 mg. 17.5 mg, 20 mg, 22.5 mg, 25 mg, 27.5 mg, 30 mg, 35 mg, 40 mg, 45 mg, 50 mg, 55 mg, 60 mg, 65 mg, 70 mg, 75 mg, 80 mg, 85 mg, 90 mg, 95 mg, or 100 mg of niraparib or pharmaceutically acceptable salt thereof once-daily, twice-daily, or thrice-daily.

In some embodiments, the methods of the invention treat subjects with a cancer with a dosage of from about 1 mg to 5 mg, 5 mg to 10 mg, 10 mg to 20 mg, 20 mg to 25 mg, 35 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, 950 mg to 1000 mg, 1000 mg to 1050 mg, 1050 mg to 1100 mg, 1100 mg to 1150 mg, 1150 mg to 1200 mg, 1200 mg to about 1250 mg, 1250 mg to 1300 mg, 1300 mg to 1350 mg, 1350 mg to 1400 mg, 1400 mg to 1450 mg, 1450 mg to 1500 mg, 1500 mg to 1550 mg, 1550 mg to 1600 mg, 1600 mg to 1650 mg, 1650 mg to 1700 mg, 1700 mg to 1750 mg, 1750 mg to 1800 mg, 1800 mg to 1850 mg, 1850 mg to 1900 mg, 1900 mg to 1950 mg, or 1950 mg to 2000 mg of niraparib or pharmaceutically acceptable salt thereof once-daily, twice-daily, or thrice-daily. In some embodiments, the methods of the invention treat subjects with a cancer with a dosage of from about 5 mg to 7.5 mg, 7 mg to 9.5 mg, 9 mg to 11.5 mg, 11 mg to 13.5 mg, 13 mg to 15.5 mg, 15 mg to 17.5 mg, 17 to 19.5 mg, 19 mg to 21.5 mg, 21 mg to 23/5 mg, 23 mg to 25.5 mg, 25 mg to 27.5 mg, 27 mg to 30 mg, 30 mg to 35 mg, 35 mg to 40 mg, 40 mg to 45 mg, 45 mg to 50 mg, 50 mg to 55 mg, 55 mg to 60 mg, 60 to 65 mg, 65 mg to 70 mg, 70 mg to 75 mg, 75 mg to 80 mg, 80 mg to 85 mg, 85 mg to 90 mg, 90 mg to 95 mg, or 95 mg to 100 mg of niraparib or pharmaceutically acceptable salt thereof once-daily, twice-daily, or thrice-daily.

Administration of the Compositions

One of the recommended dosages the niraparib described herein (e.g., as monotherapy) is three 100 mg doses taken orally once daily, equivalent to a total daily dose of 300 mg. Patients may be encouraged to take their dose at approximately the same time each day. Bedtime administration may be a potential method for managing nausea.

As described herein, doses of 1 to 2000 mg of niraparib or a pharmaceutically acceptable salt thereof may be administered for treatment of subjects, and methods and compositions described herein may comprise once-daily, twice-daily, or thrice-daily administration of a dose of up to 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, or 2000 mg once-daily, twice-daily, or thrice-daily. In some embodiments, the dose of niraparib or pharmaceutically acceptable salt thereof is from 1 mg to 5 mg, 5 mg to 10 mg, 10 mg to 20 mg, 20 mg to 25 mg, 35 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, 950 mg to 1000 mg, 1000 mg to 1050 mg, 1050 mg to 1100 mg, 1100 mg to 1150 mg, 1150 mg to 1200 mg, 1200 mg to 1250 mg, 1250 mg to 1300 mg, 1300 mg to 1350 mg, 1350 mg to 1400 mg, 1400 mg to 1450 mg, 1450 mg to 1500 mg, 1500 mg to 1550 mg, 1550 mg to 1600 mg, 1600 mg to 1650 mg, 1650 mg to 1700 mg, 1700 mg to 1750 mg, 1750 mg to 1800 mg, 1800 mg to 1850 mg, 1850 mg to 1900 mg, 1900 mg to 1950 mg, or 1950 mg to 2000 mg, once-daily, twice-daily, or thrice-daily. In some embodiments, the methods of the invention treat subjects with a cancer with a dosage of 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, or 2000 mg of niraparib or pharmaceutically acceptable salt thereof once-daily, twice-daily, or thrice-daily.

In some embodiments, a total daily dose of niraparib or a pharmaceutically acceptable salt thereof of 1 mg to 2000 mg. In some embodiments, a total daily dose of niraparib or a pharmaceutically acceptable salt thereof of 1 mg to 1000 mg, for example, or 50 to 300 mg, is administered. In some embodiments, the total daily dose of niraparib or a pharmaceutically acceptable salt thereof administered exceeds 100 mg per day. In some embodiments, the total daily dose of niraparib or a pharmaceutically acceptable salt thereof administered exceeds 200 mg per day. In some embodiments, the total daily dose of niraparib or a pharmaceutically acceptable salt thereof administered exceeds 300 mg per day. In some embodiments, the total daily dose of niraparib or a pharmaceutically acceptable salt thereof administered exceeds 400 mg per day. In some embodiments, the total daily dose of niraparib or a pharmaceutically acceptable salt thereof administered exceeds 500 mg per day.

In some embodiments, the total daily dose of niraparib or a pharmaceutically acceptable salt thereof administered does not exceed 500 mg per day. In some embodiments, the total daily dose of niraparib or a pharmaceutically acceptable salt thereof administered does not exceed 300 mg per day. In some embodiments, the total daily dose of niraparib or a pharmaceutically acceptable salt thereof administered does not exceed 100 mg per day. In some embodiments, the total daily dose of niraparib or a pharmaceutically acceptable salt thereof administered does not exceed 50 mg per day. In some embodiments, the total daily dose of niraparib or pharmaceutically acceptable salt thereof is from about 1 mg to 5 mg, 5 mg to 10 mg, 10 mg to 20 mg, 20 mg to 25 mg, 35 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, or 950 mg to 1000 mg, 1000 mg to 1050 mg, 1050 mg to 1100 mg, 1100 mg to 1150 mg, 1150 mg to 1200 mg, 1200 mg to 1250 mg, 1250 mg to 1300 mg, 1300 mg to 1350 mg, 1350 mg to 1400 mg, 1400 mg to 1450 mg, 1450 mg to 1500 mg, 1500 mg to 1550 mg, 1550 mg to 1600 mg, 1600 mg to 1650 mg, 1650 mg to 1700 mg, 1700 mg to 1750 mg, 1750 mg to 1800 mg, 1800 mg to 1850 mg, 1850 mg to 1900 mg, 1900 mg to 1950 mg, or 1950 mg to 2000 mg the total daily dose of niraparib or a pharmaceutically acceptable salt thereof is about 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

A therapeutically effective dose of niraparib or a pharmaceutically acceptable salt thereof may be about 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg per day. In some embodiments, the amount of niraparib or a pharmaceutically acceptable salt thereof administered daily is from about 1 mg to 5 mg, 5 mg to 10 mg, 10 mg to 20 mg, 20 mg to 25 mg, 35 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, 950 mg to 1000 mg, 1000 mg to 1050 mg, 1050 mg to 1100 mg, 1100 mg to 1150 mg, 1150 mg to 1200 mg, 1200 mg to 1250 mg, 1250 mg to 1300 mg, 1300 mg to 1350 mg, 1350 mg to 1400 mg, 1400 mg to 1450 mg, 1450 mg to 1500 mg, 1500 mg to 1550 mg, 1550 mg to 1600 mg, 1600 mg to 1650 mg, 1650 mg to 1700 mg, 1700 mg to 1750 mg, 1750 mg to 1800 mg, 1800 mg to 1850 mg, 1850 mg to 1900 mg, 1900 mg to 1950 mg, or 1950 mg to 2000 mg per day.

In some embodiments, the amount of niraparib or a pharmaceutically acceptable salt thereof administered one time daily is 1 mg to 5 mg, 5 mg to 10 mg, 10 mg to 20 mg, 20 mg to 25 mg, 35 mg to 50 mg, 50 mg to 75 mg, 70 mg to 95 mg, 90 mg to 115 mg, 110 mg to 135 mg, 130 mg to 155 mg, 150 mg to 175 mg, 170 mg to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, or 950 mg to 1000 mg, 1000 mg to 1050 mg, 1050 mg to 1100 mg, 1100 mg to 1150 mg, 1150 mg to 1200 mg, 1200 mg to 1250 mg, 1250 mg to 1300 mg, 1300 mg to 1350 mg, 1350 mg to 1400 mg, 1400 mg to 1450 mg, 1450 mg to 1500 mg, 1500 mg to 1550 mg, 1550 mg to 1600 mg, 1600 mg to 1650 mg, 1650 mg to 1700 mg, 1700 mg to 1750 mg, 1750 mg to 1800 mg, 1800 mg to 1850 mg, 1850 mg to 1900 mg, 1900 mg to 1950 mg, or 1950 mg to 2000 mg. In some embodiments, the amount of naraparib or a pharmaceutically acceptable salt thereof administered one time daily is 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, the amount of niraparib or a pharmaceutically acceptable salt thereof administered two times daily is 1 mg to 5 mg, 5 mg to 10 mg, 10 mg to 20 mg, 20 mg to 25 mg, 35 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, 950 mg to 1000 mg, 1000 mg to 1050 mg, 1050 mg to 1100 mg, 1100 mg to 1150 mg, 1150 mg to 1200 mg, 1200 mg to 1250 mg, 1250 mg to 1300 mg, 1300 mg to 1350 mg, 1350 mg to 1400 mg, 1400 mg to 1450 mg, 1450 mg to 1500 mg, 1500 mg to 1550 mg, 1550 mg to 1600 mg, 1600 mg to 1650 mg, 1650 mg to 1700 mg, 1700 mg to 1750 mg, 1750 mg to 1800 mg, 1800 mg to 1850 mg, 1850 mg to 1900 mg, 1900 mg to 1950 mg, or 1950 mg to 2000 mg. In some embodiments, the amount of niraparib or a pharmaceutically acceptable salt thereof administered two times daily is 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, the amount of niraparib or a pharmaceutically acceptable salt thereof administered three times daily is 1 mg to 5 mg, 5 mg to 10 mg, 10 mg to 20 mg, 20 mg to 25 mg, 35 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, 950 mg to 1000 mg, 1000 mg to 1050 mg, 1050 mg to 1100 mg, 1100 mg to 1150 mg, 1150 mg to 1200 mg, 1200 mg to 1250 mg, 1250 mg to 1300 mg, 1300 mg to 1350 mg, 1350 mg to 1400 mg, 1400 mg to 1450 mg, 1450 mg to 1500 mg, 1500 mg to 1550 mg, 1550 mg to 1600 mg, 1600 mg to 1650 mg, 1650 mg to 1700 mg, 1700 mg to 1750 mg, 1750 mg to 1800 mg, 1800 mg to 1850 mg, 1850 mg to 1900 mg, 1900 mg to 1950 mg, or 1950 mg to 2000 mg. In some embodiments, the amount of niraparib or a pharmaceutically acceptable salt thereof administered three times daily is 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, the niraparib or a pharmaceutically acceptable salt thereof is present at a dose from about 1 mg to about 2000 mg, including, but not limited to, about 1 mg, 5 mg, 10.0 mg, 10.5 mg, 11.0 mg, 11.5 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 30.5 mg, 31 mg, 31.5 mg, 32 mg, 32.5 mg, 33 mg, 33.5 mg, 34 mg, 34.5 mg, 35 mg, 35.5 mg, 36 mg, 36.5 mg, 37 mg, 37.5 mg, 38 mg, 38.5 mg, 39 mg, 39.5 mg, 40 mg, 40.5 mg, 41 mg, 41.5 mg, 42 mg, 42.5 mg, 43 mg, 43.5 mg, 44 mg, 44.5 mg, 45 mg, 45.5 mg, 46 mg, 46.5 mg, 47 mg, 47.5 mg, 48 mg, 48.5 mg, 49 mg, 49.5 mg, 50 mg, 55 mg, 60 mg, 65 mg, 70 mg, 75 mg, 80 mg, 85 mg, 90 mg, 95 mg, 100, 105 mg, 110 mg, 115 mg, 120 mg, 120.5 mg, 121 mg, 121.5 mg, 122 mg, 122.5 mg, 123 mg, 123.5 mg, 124 mg, 124.5 mg, 125 mg, 125.5 mg, 126 mg, 126.5 mg, 127 mg, 127.5 mg, 128 mg, 128.5 mg, 129 mg, 129.5 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, the niraparib or a pharmaceutically acceptable salt thereof is present at a dose from about 1 mg to 5 mg, 5 mg to 10 mg, 10 mg to 20 mg, 20 mg to 25 mg, 25 mg to 100 mg, 35 mg to 140 mg, 70 mg to 140 mg, 80 mg to 135 mg, 10 mg to 25 mg, 25 mg to 50 mg, 50 mg to 100 mg, 100 mg to 150 mg, 150 mg to 200 mg, 10 mg to 35 mg, 35 mg to 70 mg, 70 mg to 105 mg, 105 mg to 140 mg, 140 mg to 175 mg, or 175 mg to 200 mg, 35 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, or 950 mg to 1000 mg, 1000 mg to 1050 mg, 1050 mg to 1100 mg, 1100 mg to 1150 mg, 1150 mg to 1200 mg, 1200 mg to 1250 mg, 1250 mg to 1300 mg, 1300 mg to 1350 mg, 1350 mg to 1400 mg, 1400 mg to 1450 mg, 1450 mg to 1500 mg, 1500 mg to 1550 mg, 1550 mg to 1600 mg, 1600 mg to 1650 mg, 1650 mg to 1700 mg, 1700 mg to 1750 mg, 1750 mg to 1800 mg, 1800 mg to 1850 mg, 1850 mg to 1900 mg, 1900 mg to 1950 mg, or 1950 mg to 2000 mg.

Frequency of Administration

In some embodiments, a composition disclosed herein is administered to an individual in need thereof once. In some embodiments, a composition disclosed herein is administered to an individual in need thereof more than once. In some embodiments, a first administration of a composition disclosed herein is followed by a second administration of a composition disclosed herein. In some embodiments, a first administration of a composition disclosed herein is followed by a second and third administration of a composition disclosed herein. In some embodiments, a first administration of a composition disclosed herein is followed by a second, third, and fourth administration of a composition disclosed herein. In some embodiments, a first administration of a composition disclosed herein is followed by a second, third, fourth, and fifth administration of a composition disclosed herein. In some embodiments, a first administration of a composition disclosed herein is followed by a drug holiday.

The number of times a composition is administered to an individual in need thereof depends on the discretion of a medical professional, the disorder, the severity of the disorder, and the individual's response to the formulation. In some embodiments, a composition disclosed herein is administered once to an individual in need thereof with a mild acute condition. In some embodiments, a composition disclosed herein is administered more than once to an individual in need thereof with a moderate or severe acute condition. In the case wherein the patient's condition does not improve, upon the doctor's discretion the administration of niraparib may be administered chronically, that is, for an extended period of time, including throughout the duration of the patient's life in order to ameliorate or otherwise control or limit the symptoms of the patient's disease or condition.

In some embodiments, the composition is administered at predetermined time intervals over an extended period of time. In some embodiments, the niraparib composition is administered once every day. In some embodiments, the niraparib composition is administered every other day. In some embodiments, the niraparib composition is administered over 1 week, 2 weeks, 1 month, 2 months, 3 months, 6 months, 1 year, 2 years, 3 years, 4 years, 5 years, 6 years, 7 years, 8 years, 9 years, 10 years, 11 years, or 12-15 years.

In some embodiments, the niraparib composition is administered in doses having a dose-to-dose niraparib concentration variation of less than 50%, less than 40%, less than 30%, less than 20%, less than 10%, or less than 5%.

In the case wherein the patient's status does improve, upon the doctor's discretion the administration of the niraparib may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. A first or second dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%. For example, a first or second dose reduction during a drug holiday may be a dose reduced from 5 mg to 1 mg, 10 mg to 5 mg, 20 mg to 10 mg, 25 mg to 10 mg, 50 mg to 25 mg, 75 mg to 50 mg, 75 mg to 25 mg, 100 mg to 50 mg, 150 mg to 75 mg, 100 mg to 25 mg, 200 mg to 100 mg, 200 to 50 mg, 250 mg to 100 mg, 300 mg to 50 mg, 300 mg to 100 mg, 300 mg to 200 mg, 400 mg to 50 mg, 400 mg to 100 mg, 400 mg to 200 mg, 500 mg to 50 mg, 500 mg to 100 mg, 500 mg to 250 mg, 1000 mg to 50 mg, 1000 mg to 100 mg, or 1000 mg to 500 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, 950 mg to 1000 mg, 1000 mg to 1050 mg, 1050 mg to 1100 mg, 1100 mg to 1150 mg, 1150 mg to 1200 mg, 1200 mg to 1250 mg, 1250 mg to 1300 mg, 1300 mg to 1350 mg, 1350 mg to 1400 mg, 1400 mg to 1450 mg, 1450 mg to 1500 mg, 1500 mg to 1550 mg, 1550 mg to 1600 mg, 1600 mg to 1650 mg, 1650 mg to 1700 mg, 1700 mg to 1750 mg, 1750 mg to 1800 mg, 1800 mg to 1850 mg, 1850 mg to 1900 mg, 1900 mg to 1950 mg, or 1950 mg to 2000 mg. For example, a first or second dose reduction during a drug holiday may be a dose reduced by 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, or 2000 mg.

Once improvement of the patient's condition has occurred, a maintenance niraparib dose is administered if necessary. Subsequently, the dosage or the frequency of administration, or both, is optionally reduced, as a function of the symptoms, to a level at which the improved disease, disorder or condition is retained. In certain embodiments, patients require intermittent treatment on a long-term basis upon any recurrence of symptoms.

Combination Therapies

Niraparib tablet compositions described herein can be useful as monotherapy or in combination therapy with the administration of one or more additional therapeutic agents or lines of therapy.

For example, a tablet composition described herein can be administered in combination with surgery, a radiotherapy, a chemotherapy, an immunotherapy, an anti-angiogenic agent, or an anti-inflammatory agent.

Where a niraparib tablet composition is administered in combination with one or more different therapeutic agents (e.g., as described herein), administering of the niraparib tablet composition can occur sequentially with the administering of the one or more different therapeutic agents. For example, administration of the niraparib tablet composition occurs before administration of the one or more different therapeutic agents. In embodiments, administration of the niraparib tablet composition occurs after administration of the one or more different therapeutic agents. In other embodiments, administering of the niraparib tablet composition occurs simultaneously with the administering of the one or more different therapeutic agents.

In embodiments, a tablet composition described herein is administered in combination with one or more immune checkpoint inhibitors. In embodiments, a checkpoint inhibitor is an agent capable of inhibiting any of the following: PD-1 (e.g., inhibition via anti-PD-1, anti-PD-L1, or anti-PD-L2 therapies), CTLA-4, TIM-3, TIGIT, LAGs (e.g., LAG-3), CEACAM (e.g., CEACAM-1, -3 and/or -5), VISTA, BTLA, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, TGFR (e.g., TGFR beta), B7-H1, B7-H4 (VTCN1), OX-40, CD137, CD40, IDO, or CSF-1R. In embodiments, a checkpoint inhibitor is a small molecule, a nucleic acid, a polypeptide (e.g., an antibody), a carbohydrate, a lipid, a metal, or a toxin. In embodiments, a checkpoint inhibitor is an antibody, an antibody conjugate, or an antigen-binding fragment thereof.

In embodiments, an immune checkpoint inhibitor is a PD-1 inhibitor. In embodiments, a PD-1 inhibitor is a small molecule, a nucleic acid, a polypeptide (e.g., an antibody, an antibody conjugate, or an antigen-binding fragment thereof), a carbohydrate, a lipid, a metal, or a toxin. In embodiments, a PD-1 inhibitor is a PD-1 binding agent (e.g., an antibody, an antibody conjugate, or an antigen-binding fragment thereof). In embodiments, a PD-1 binding agent is an antibody, an antibody conjugate, or an antigen-binding fragment thereof. In embodiments, a PD-1 binding agent is TSR-042, nivolumab, pembrolizumab, atezolizumab, durvalumab, avelumab, PDR-001, tislelizumab (BGB-A317), cemiplimab (REGN2810), LY-3300054, JNJ-63723283, MGA012, BI-754091, IBI-308, camrelizumab (HR-301210), BCD-100, JS-001, CX-072, BGB-A333, AMP-514 (MEDI-0680), AGEN-2034, CS1001, Sym-021, SHR-1316, PF-06801591, LZMO09, KN-035, AB122, genolimzumab (CBT-501), FAZ-053, CK-301, AK 104, or GLS-010. In embodiments, a PD-1 inhibitor is a PD-L1 or PD-L2 binding agent such as durvalumab, atezolizumab, avelumab, BGB-A333, SHR-1316, FAZ-053, CK-301, or, PD-L1 millamolecule, or derivatives thereof. In embodiments, an anti-PD-1 agent is pembrolizumab. In embodiments, an anti-PD-1 agent is nivolumab. In some embodiments, a PD-1 antibody agent is as disclosed in International Patent Application Publication Nos. WO2014/179664, WO 2018/085468, or WO 2018/129559. In further embodiments, a PD-1 antibody agent is administered according to a method disclosed in International Patent Application Publication Nos. WO2014/179664, WO 2018/085468, or WO 2018/129559. In embodiments, an anti-PD-1 agent is TSR-042.

In embodiments, an immune checkpoint inhibitor is a TIM-3 inhibitor. In embodiments, a TIM-3 inhibitor is a small molecule, a nucleic acid, a polypeptide (e.g., an antibody, an antibody conjugate, or an antigen-binding fragment thereof), a carbohydrate, a lipid, a metal, or a toxin. In embodiments, a TIM-3 inhibitor is a TIM-3 binding agent (e.g., an antibody, an antibody conjugate, or an antigen-binding fragment thereof). In embodiments, a TIM-3 binding agent is an antibody, an antibody conjugate, or an antigen-binding fragment thereof. In some embodiments, a TIM-3 antibody agent is MBG453, LY3321367, Sym023, TSR-022, or a derivative thereof. In some embodiments, a TIM-3 antibody agent is as disclosed in International Patent Application Publication Nos. WO2016/161270, WO 2018/

085469, or WO 2018/129553. In some embodiments, a TIM-3 antibody agent is administered as disclosed in International Patent Application Publication Nos. WO2016/161270, WO 2018/085469, or WO 2018/129553. In some embodiments, a TIM-3 antibody agent is TSR-022.

In embodiments, an immune checkpoint inhibitor is a LAG-3 inhibitor. In embodiments, an anti-LAG-3 agent is an antibody, an antibody conjugate, or an antigen-binding fragment thereof. In embodiments, an anti-LAG-3 agent is a small molecule, a nucleic acid, a polypeptide (e.g., an antibody), a carbohydrate, a lipid, a metal, or a toxin. In embodiments, an anti-LAG-3 agent is a small molecule. In embodiments, an anti-LAG-3 agent is a LAG-3 binding agent. In embodiments, an anti-LAG-3 agent is an antibody, an antibody conjugate, or an antigen-binding fragment thereof. In embodiments, an anti-LAG-3 agent is IMP321, relatlimab (BMS-986016), BI 754111, GSK2831781 (IMP-731), Novartis LAG525 (IMP701), REGN3767, MK-4280, MGD-013, GSK-2831781, FS-118, XmAb22841, INCAGN-2385, FS-18, ENUM-006, AVA-017, AM-0003, Avacta PD-L1/LAG-3 bispecific affamer, iOnctura anti-LAG-3 antibody, Arcus anti-LAG-3 antibody, or Sym022, or TSR-033. In some embodiments, a LAG-3 antibody agent is as disclosed in International Patent Application Publication WO2016/126858 or in in International Patent Application No. PCT/US18/30027. In some embodiments, a LAG-3 antibody agent is administered as disclosed in International Patent Application Publication WO2016/126858 or in in International Patent Application No. PCT/US18/30027. In embodiments, a LAG-3 antibody agent is TSR-033.

In embodiments, a niraparib tablet composition is administered in combination with a PD-1 inhibitor (e.g., TSR-042, pembrolizumab, or nivolumab). In embodiments, a niraparib tablet composition is administered in combination with a TIM-3 inhibitor (e.g., TSR-022). In embodiments, a niraparib tablet composition is administered in combination with a LAG-3 inhibitor (e.g., TSR-033). In embodiments, a niraparib tablet composition is administered in combination with a PD-1 inhibitor (e.g., TSR-042, pembrolizumab, or nivolumab) and a TIM-3 inhibitor (e.g., TSR-022). In embodiments, a niraparib tablet composition is administered in combination with a PD-1 inhibitor (e.g., TSR-042, pembrolizumab, or nivolumab) and a LAG-3 inhibitor (e.g., TSR-033). In embodiments, a niraparib tablet composition is administered in combination with a TIM-3 inhibitor (e.g., TSR-022) and a LAG-3 inhibitor (e.g., TSR-033). In embodiments, a niraparib tablet composition is administered in combination with a PD-1 inhibitor (e.g., TSR-042, pembrolizumab, or nivolumab), a TIM-3 inhibitor (e.g., TSR-022), and a LAG-3 inhibitor (e.g., TSR-033).

In embodiments, a niraparib tablet composition is administered in combination with one or more chemotherapy agents.

In embodiments, a niraparib tablet composition is administered in combination with a platinum-based chemotherapy agent (e.g., one or more of cisplatin, carboplatin, oxaliplatin, nedaplatin, triplatin tetranitrate, phenanthriplatin, picoplatin, and satraplatin).

In embodiments, a niraparib tablet composition is administered in combination with a chemotherapy agent that is aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, or vinorelbine.

In embodiments, a niraparib tablet composition is administered in combination with a second agent that is a regulatory T cell (Treg) inhibitory agent, a macrophage inhibitory agent, an antigen specific immune response enhancer agent, antigen specific immune response enhancer agent, anti-angiogenic agent, a chemotherapy agent or a combination thereof. In embodiments, a second agent is any second agent described in International Application No. PCT/US18/33437, herein incorporated by reference in its entirety.

In embodiments, a macrophage inhibitory agent is selected from the group consisting of a macrophage recruitment inhibitory agent (e.g., an anti-CCL2/CCR2 agent, an anti-IL6 agent, an anti-M-CSFR agent, and combinations thereof), an M2 macrophage antisurvival agent, an M1 macrophage enhancing agent, an M2 to M1 polarizing agent, a macrophage activity inhibitor agent and combinations thereof. In embodiments, a macrophage recruitment inhibitory agent is selected from the group consisting of trabectedin, RS102895, PF-04136309, CNTO888, MLN1202, siltuximab, JNJ-28312141, GW2580, IMC-CS4 (LY3022855), emactuzumab, AMG820, pexidartinib, linifanib, OSI-930, CEP-32496, PLX7846, BLZ945, ARRY-382, JNJ-40346527, MCS110, PLX3397, PLX6134, PD-0360324, FPA008, and combinations thereof. In embodiments, a M2 macrophage antisurvival agent is selected from the group consisting of an MMP inhibitor, clodronate, zoledronic acid, dichloromethylene bisphosphonate, trabectedin, dasatinib, retinoic acid, attenuated bacteria (e.g., *Shigella flexneri, Salmonella typhimurium, Listeria monocytogens, Chlamydia psittaci, Legionella pneumophila*), and combinations thereof. In embodiments, a M1 macrophage enhancing agent or the M2 to M1 polarizing agent is selected from the group consisting of an anti-CD40 agent, an anti-IL-10R agent, a CD47 antagonist (e.g., Hu5F9-G4, CC-90002, and CD47-Fc fusion protein TTI-621), PolyI:C, LPS, monophosphoryl A, imiquimod, R-848, CpG-ODN, IFN-α, IFN-β, IFN-γ, GM-CSF, IL-12, IL-2, IL-15, Tα1, ibrutinib, EF-022 and combinations thereof. In embodiments, macrophage activity inhibitory agent is selected from the group consisting of a STAT3 inhibitor, a STATE inhibitor, or an anti-tumor drug agent (e.g., a macrophage activity inhibitory agent is WP1066, sunitinib, sorafenib, STA-21, IS3 295, S3I-M2001, AS1517499, leflunomide, TMC-264, histidine-rich glycoprotein (HRG), copper chelate (CuNG), 5,6-dimethylxanthenone-4-acetic acid (MDXAA), vadimezan (ASA404), cisplatin, silibinin, proton pump inhibitor pantoprazole (PPZ), or CNI-1493, or combinations thereof). In embodiments, a macrophage inhibitor agent is an anti-IL-1α agent (e.g., xilonix).

In embodiments a regulatory T cell (Treg) inhibitory agent is selected from the group consisting of a Treg ablating agent, a Treg migration inhibitor agent, a Treg function inhibitor agent, and combinations thereof. In embodiments, a Treg ablating agent is selected from the group consisting of cyclophosphamide, paclitaxel, imatinib, sunitinib, sorafenib, dasatinib, temozolomide, daclizumab, denileukin diftitox, and combinations thereof. In embodiments, a Treg migration inhibitor agent is selected from the group consisting of AMD3100, mogamulizumab, casuarinin, fucoidan, and combinations thereof. In embodiments, a Treg function inhibitor agent is selected from the group consisting of an anti-CTLA4 agent (e.g., ipilimumab, tremelimumab), an anti-OX40 agent, an anti-GITR agent, an adenosine receptor antagonist (e.g., caffeine, theophylline, theobromine, and 8-phenylxanthines), P60, and combinations thereof.

In embodiments, an antigen specific immune response enhancer agent is selected from the group consisting of an anti-PD-1 agent, an anti-PD-L1 agent, a GITR (glucocorticoid-induced TNFR-related protein) stimulating agent, an anti-CTLA4 agent, an anti-TIM-3 agent, an anti-LAG-3 agent, an anti-IDO agent, an agent that enhances tumor antigen presentation (e.g., personalized cancer vaccine, autologous antigen presenting cell, autologous dendritic cells, artificial antigen presenting cell), a chemokine signaling agent, an anti-VEGF agent, a cytokine signal stimulating agent, and combinations thereof.

In embodiments, a GITR stimulating agent is selected from the group consisting of DTA-1, mGITRL, pGITRL, and combinations thereof. In embodiments, an anti-CTLA4 agent is selected from the group consisting of ipilimumab, tremelimumab, and combinations thereof. In embodiments, a chemokine signaling agent is selected from the group consisting of CXCL16, a CXCR6 chemokine receptor (CD186) agonist, and combinations thereof. In embodiments, an anti-VEGF agent is selected from the group consisting of bevacizumab, pazopanib, sunitinib, sorafenib, axitinib, ponatinib, regorafenib, cabozantinib, vandetanib, ramucirumab, lenvatinib, ziv-aflibercept, and combinations thereof. In embodiments, a cytokine signal stimulating agent is an interleukin or an interferon. In embodiments, an interleukin is selected from the group consisting of IL-2, IL-1, IL-7, IL-15, IL-12, IL-18 and combinations thereof. In embodiments, an interferon is IFN alpha.

In embodiments, an antigen specific immune response enhancer agent is selected from the group consisting of a flavonoid (e.g., flavonoid glycoside), lidocaine, lamotrigine, sulfamethoxazole, phenytoin, carbamazepine, sulfamethoxazole, phenytoin, allopurinol, paracetamol, mepivacaine, p-phenylenediamine, ciprofloxacin and moxifloxacin.

In embodiments, an anti-angiogenic agent is TNP-470, platelet factor 4, thrombospondin-1, tissue inhibitors of metalloproteases (TIMP1 and TIMP2), prolactin, angiostatin, endostatin, bFGF soluble receptor, transforming growth factor beta, interferon alpha, soluble KDR and FLT-1 receptors, placental proliferin-related protein, and combinations thereof. In embodiments, an anti-angiogenic agent reduces the production of a pro-angiogenic factor, inhibits an interaction between a pro-angiogenic factor and a pro-angiogenic receptor, inhibits a function of a pro-angiogenic factor, inhibits a function of a pro-angiogenic factor receptor, reduces of blood flow by disruption of blood vessels, inhibits vessel sprouting, or any combinations thereof. In embodiments, an anti-angiogenic agent is a small organic or inorganic molecule; a saccharine; an oligosaccharide; a polysaccharide; a carbohydrate; a peptide; a protein; a peptide analog; a peptide derivative; a lipid; an antibody; an antibody fragment, a peptidomimetic; a nucleic acid; a nucleic acid analog; a nucleic acid derivative; an extract made from biological materials; a naturally occurring or synthetic composition; a metal; a toxin; or any combination thereof. In embodiments, an anti-angiogenic agent is selected from the group consisting of bevacizumab, itraconazole, carboxyamidotriazole, TNP-470, fumagillin, CM101, IL-12, platelet factor-4, suramin, SU5416, thrombospondin, angiostatic steroids, heparin, cartilage-derived angiogenesis inhibitory factor, matrix metalloproteinase inhibitor, angiostatin, endostatin, 2-methoxyestradiol, tecogalan, tetrathiomolybdate, thrombospondin, thalidomide, prolactin, αVβ3 inhibitor, lenalidomide, linomide, ramucirumab, tasquinimod, ranibizumab, sorafenib, sunitinib, pazopanib, everolimus, tissue inhibitors of metalloproteases (TIMP1 and TIMP2), bFGF soluble receptor, transforming growth factor beta, interferon alpha, soluble KDR and FLT-1 receptors, placental proliferin-related protein, pazopanib, sunitinib, sorafenib, axitinib, ponatinib, cabozantinib, regorafenib, vandetanib, lenvatinib, semaxanib, SU6668, vatalanib, tivozanib, cediranib, protamine, heparin, steroids, ascorbic acid ethers, sulfated polysaccharide DS 4152, fumagillin, AGM 12470, neovastat, RO4929097, MRK-003, MK-0752, PF03084014, MEDI0639, curcumin, 3,3'-diindolylmethane (DIM), resveratrol, 3,5-bis(2,4-difluorobenzylidene)-4-piperidone (DiFiD) and epigallocatechin-3-gallate (EGCG), honokiol, OMP-21M18, navicixizumab (OMP-305B83), Flt2-11, CBO-P11, Je-11, V1, and any combination thereof.

In some embodiments, an anti-angiogenic agent inhibits a DLL4/Notch signaling pathway.

In some embodiments, the angiogenesis inhibitor inhibiting the DLL4/Notch signaling pathway is a gamma-secretase inhibitor (GSI), a siRNA, or a monoclonal antibody against a Notch receptor or ligand. In some embodiments, an anti-angiogenic agent is selected from the group consisting of RO4929097, MRK-003, MK-0752, PF03084014, MEDI0639, curcumin, 3,3'-diindolylmethane (DIM), resveratrol, 3,5-bis(2,4-difluorobenzylidene)-4-piperidone (DiFiD) and epigallocatechin-3-gallate (EGCG), honokiol, and any combination thereof.

In some embodiments, an anti-angiogenic agent inhibits a vascular endothelial growth factor (VEGF)/vascular endothelial growth factor receptor (VEGFR) pathway. In some embodiments, an anti-angiogenic agent is selected from the group consisting of Akt Inhibitor, calcineurin autoinhibitory peptide, ET-18-OCH3, Go 6983, NG-Nitro-L-arginine methyl ester, p21-activated kinase Inhibitor, cPLA2a inhibitor, PI-103, PP2, SB 203580, U0126, VEGFR tyrosine kinase inhibitor V, VEGFR2 kinase inhibitor VI, VEGFR2 kinase inhibitor III, ZM 336372, and any combination thereof.

In some embodiments, an anti-angiogenic agent inhibits a VEGF family protein and/or a VEGFR family protein. In some embodiments, the VEGF family protein comprises VEGF-A, VEGF-B, VEGF-C, VEGF-D, P1GF (placental growth factor), VEGF-E (Orf-VEGF), *Trimeresurus flavoviridis* svVEGF, or any combination thereof. In some embodiments, an anti-angiogenic agent is bevacizumab, ranibizumab, OPT-302, ziv-aflibercept, or any combinations thereof. thereof. In some embodiments, an anti-angiogenic agent is Flt2-11, CBO-P11, Je-11, V1, or any combination thereof. In some embodiments, an anti-angiogenic agent is pazopanib, sunitinib, sorafenib, axitinib, ponatinib, cabozantinib, regorafenib, vandetanib, lenvatinib, semaxanib, SU6668, vatalanib, tivozanib, cediranib, or any combination thereof.

Methods of Making Niraparib Formulations

Provided herein are methods of manufacturing niraparib tablet compositions for treating cancers. Also described herein are niraparib tablet formulations containing niraparib tosylate monohydrate and at least one pharmaceutically acceptable excipient formed by disclosed methods, and the therapeutic use of such formulation orally. In some embodiments, the formulation comprises niraparib; a first diluent selected from lactose monohydrate, lactose anhydrous, mannitol, and calcium phosphate dibasic, magnesium stearate; a second diluent selected from microcrystalline cellulose, starch, polyethylene oxide, and hydroxypropyl methylcellulose (HPMC); and a binder selected from povidone, hydroxypropyl cellulose, and hydroxypropyl methylcellulose. In some embodiments, the formulation comprises the active niraparib tosylate (monohydrate) at about 35% w/w to about 60% w/w. In some embodiments, the formulation comprises the active niraparib tosylate (monohydrate) at about 40% w/w to about 55% w/w. In some embodiments, the formulation comprises the active niraparib tosylate (monohydrate) at about 45% w/w to about 50% w/w. In some embodiments, the formulation comprises the active niraparib tosylate (monohydrate) at about 46% w/w to about 48% w/w.

In some embodiments, the pharmaceutical composition of the present invention is prepared by blending the niraparib with excipients. The blending of above components can preferably be carried out in a mixer, for example in a tumble blender. Bulk density and tapped density can be determined according to USP 24, Test 616 "Bulk Density and Tapped Density".

In some embodiments, the solid dosage forms of the present invention may be in the form of a powder (including a sterile packaged powder, a dispensable powder, or an effervescent powder), a capsule (including both soft or hard capsules, e.g., capsules made from animal-derived gelatin or plant-derived HPMC, or "sprinkle capsules"), or a tablet. In some embodiments, the pharmaceutical formulation is in the form of a powder. Additionally, pharmaceutical formulations of the present invention may be administered as a single capsule or in multiple capsule dosage form. In some embodiments, the pharmaceutical formulation is administered in one, or two, or three, or four, capsules. In some embodiments, the solid dosage forms disclosed herein are in the form of tablet. In some embodiments, the pharmaceutical formulations disclosed herein are administered as a single tablet or in multiple tablet dosage forms. In some embodiments, the pharmaceutical formulation is administered in one, or two, or three, or four tablets.

In some embodiments, solid dosage forms, are prepared by mixing niraparib particles with one or more pharmaceutical excipients to form a bulk blend composition. When referring to these bulk blend compositions as homogeneous, it is meant that the niraparib particles are dispersed evenly throughout the composition so that the composition may be readily subdivided into equally effective unit dosage forms, such as capsules or tablets. The individual unit dosages may also comprise film coatings, which disintegrate upon oral ingestion or upon contact with diluents.

Non-limiting pharmaceutical techniques for preparation of solid dosage forms include, e.g., one or a combination of methods: (1) dry mixing, (2) direct compression, (3) milling, (4) dry or non-aqueous granulation, (5) wet or dry granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

The invention should not be considered limited to these particular conditions for combining the components and it will be understood, based on this disclosure that the advantageous properties can be achieved through other conditions provided the components retain their basic properties and substantial homogeneity of the blended formulation components of the formulation is otherwise achieved without any significant segregation.

In one embodiment for preparing the blend, the components are weighed and placed into a blending container. Blending is performed for a period of time to produce a homogenous blend using suitable mixing equipment. Optionally, the blend is passed through a mesh screen to delump the blend. The screened blend may be returned to the blending container and blended for an additional period of time. Lubricant may then be added and the blend mixed for an additional period of time.

In the pharmaceutical industry, milling is often used to reduce the particle size of solid materials. Many types of mills are available including pin mills, hammer mills and jet mills. One of the most commonly used types of mill is the hammer mill. The hammer mill utilizes a high-speed rotor to which a number of fixed or swinging hammers are attached. The hammers can be attached such that either the knife face or the hammer face contacts the material. As material is fed into the mill, it impacts on the rotating hammers and breaks up into smaller particles. A screen is located below the hammers, which allows the smaller particles to pass through the openings in the screen. Larger particles are retained in the mill and continue to be broken up by the hammers until the particles are fine enough to flow through the screen. The material may optionally be screened. In screening, material is placed through a mesh screen or series of mesh screens to obtain the desired particle size.

Wet Granulation

In some embodiments, wet granulation is used to prepare the formulations disclosed herein.

Disclosed herein in one aspect is a method of making a composition comprising a tablet from wet granulation comprising niraparib comprising: a) forming an intragranular phase comprising i) combining niraparib, a first diluent (e.g., lactose monohydrate, lactose anhydrous, mannitol, and calcium phosphate dibasic), and a second diluent (e.g., microcrystalline cellulose-microcrystalline cellulose, starch, polyethylene oxide, and hydroxypropyl methylcellulose (HPMC)) to form a composition comprising niraparib, the first diluent, and the second diluent; and ii) wet granulating the composition comprising niraparib, the first diluent, and second diluent to form granules; b) forming an extragranular phase comprising iii) combining the granules with at least one pharmaceutically acceptable excipient to form a mixture; and c) forming a tablet by compressing the mixture obtained from step iii).

Also disclosed herein is a method of making a composition comprising a tablet from wet granulation comprising niraparib comprising: a) forming an intragranular phase comprising i) combining niraparib, lactose monohydrate, and microcrystalline cellulose to form a composition comprising niraparib, lactose monohydrate, and microcrystalline cellulose; and ii) wet granulating the composition comprising niraparib, lactose monohydrate, and microcrystalline cellulose to form granules; b) forming an extragranular phase comprising iii) combining the granules with at least one pharmaceutically acceptable excipient to form a mixture; and c) forming a tablet by compressing the mixture obtained from step iii).

In some embodiments, the wet granulating from step ii) further comprises adding a binder. In some embodiments, the binder is a liquid binder. In some embodiments, the liquid binder is dissolved povidone. In some embodiments, the liquid binder is dissolved starch, dissolved hydroxypropyl cellulose (HPC), dissolved hydroxypropyl methylcellulose (HPMC), or liquid polyethylene glycol (PEG). In some embodiments, the liquid binder is a melted binder. In some embodiments, the melted binder is a hydrophilic polyethylene glycol (PEG), poloxamer, hydrophobic fatty acid, fatty alcohol, wax, hydrogenated vegetable oil, or glyceride. In some embodiments, the binder is a dry binder. In some embodiments, the dry binder is hydroxypropyl cellulose (HPC). In some embodiments, the dry binder is hydroxypropyl methylcellulose (HPMC). In some embodiments, the dry binder is povidone (PVP) or starch. In some embodiments, the wet granulating from step ii) further comprises wet-sieving. In some embodiments, the wet granulating from step ii) further comprises drying and dry sieving.

Moisture-Activated Dry Granulation

In some embodiments, moisture-activated dry granulation is used to prepare the formulation described herein.

Provided herein in another aspect is a method of making a composition comprising a tablet from moisture-activated dry granulation comprising niraparib comprising: (a) forming an intragranular phase comprising i) combining niraparib, a first diluent (e.g., lactose monohydrate, lactose anhydrous, mannitol, and calcium phosphate dibasic), and a second diluent (e.g., microcrystalline cellulose microcrystalline cellulose, starch, polyethylene oxide, and hydroxypropyl methylcellulose (HPMC)) to form a composition comprising niraparib, the first diluent, and the second diluent; ii) granulating the composition comprising niraparib, the first diluent, and the second diluent to form granules; and (b) forming an extragranular phase comprising iii) combining the granules with at least one pharmaceutically acceptable excipient to form a mixture; and (c) forming a tablet by compressing the mixture obtained from step iii). A method as provided herein where the combining step i) further comprises combining with an adsorbant or absorbant.

Provided herein in another aspect is a method of making a composition comprising a tablet from moisture-activated dry granulation comprising niraparib comprising: (a) forming an intragranular phase comprising i) combining niraparib, lactose monohydrate, and microcrystalline cellulose to form a composition comprising niraparib, lactose monohydrate, and microcrystalline cellulose; ii) granulating the composition comprising niraparib, lactose monohydrate, and microcrystalline cellulose to form granules; and (b) forming an extragranular phase comprising iii) combining the granules with at least one pharmaceutically acceptable excipient to form a mixture; and (c) forming a tablet by compressing the mixture obtained from step iii).

In some embodiments, the granulating from step ii) further comprises adding a binder. In some embodiments, the binder is a liquid binder. In some embodiments, the liquid binder is dissolved povidone. In some embodiments, the liquid binder is water, dissolved starch, dissolved hydroxypropyl cellulose (HPC), dissolved hydroxypropyl methylcellulose (HPMC), or liquid polyethylene glycol (PEG). In some embodiments, the composition further comprises a dry binder. In some embodiments, water is added to the composition comprising the dry binder. In some embodiments, the granulating from step ii) further comprises drying and dry sieving. In some embodiments, drying comprises the addition of a glidant. In some embodiments, the glidant is silicon dioxide. In some embodiments, the glidant is silicon dioxide, tribasic calcium phosphate, calcium silicate, cellulose, magnesium silicate, magnesium trisilicate, starch, talc, or mixtures thereof Dry Granulation In some embodiments, dry granulation is used to prepare the formulations described herein.

Provided in another aspect is a method of making a composition comprising a tablet from dry granulation comprising niraparib comprising: a) forming an intragranular phase comprising i) combining niraparib, a first diluent (e.g., lactose monohydrate, lactose anhydrous, mannitol, and calcium phosphate dibasic), a second diluent (e.g., microcrystalline cellulose microcrystalline cellulose, starch, polyethylene oxide, and hydroxypropyl methylcellulose (HPMC)), and a lubricant (e.g., magnesium stearate) to form a composition comprising niraparib, the first diluent, the second diluent, and the lubricant; and ii) dry granulating the composition comprising niraparib, the first diluent, the second diluent, and the lubricant to form granules; b) forming an extragranular phase comprising iii) combining the granules with at least one pharmaceutically acceptable excipient to form a mixture; and c) forming a tablet by compressing the mixture obtained from step iii).

In some embodiments, the composition further comprises a dry binder. In some embodiments, water is added to the composition comprising the dry binder. In some embodiments, combining niraparib, the first diluent, the second diluent, and the lubricant to form a composition comprising niraparib, the first diluent, the second diluent, and the lubricant from step i) further comprises blending the niraparib, the first diluent, the second diluent, and the lubricant. In some embodiments, dry granulating from step ii) comprises slugging and milling. In some embodiments, the ribbon thickness is from about 0.1 mm to about 3.5 mm. In some embodiments, the ribbon thickness is about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3, about 1.4 mm, about 1.5 mm, about 1.6 mm, about 1.7 mm, about 1.8 mm, about 1.9 mm, about 2.0 mm, about 2.1 mm, about 2.2 mm about 2.3 mm, about 2.4 mm, about 2.5 mm, about 2.6 mm, about 2.7 mm, about 2.8 mm, about 2.9 mm, about 3.0 mm, about 3.1 mm, about 3.2 mm, about 3.3 mm, about 3.4 mm, or about 3.5 mm.

Provided in another aspect is a method of making a composition comprising a tablet from dry granulation comprising niraparib comprising: a) forming an intragranular phase comprising i) combining niraparib, a diluent selected from mannitol and calcium phosphate dibasic, microcrystalline cellulose, and magnesium stearate to form a composition comprising niraparib, the diluent selected from mannitol and calcium phosphate dibasic, microcrystalline cellulose, and magnesium stearate; and ii) dry granulating the composition comprising niraparib, the diluent selected from mannitol and calcium phosphate dibasic, microcrystalline cellulose, and magnesium stearate to form granules; b) forming an extragranular phase comprising iii) combining the granules with at least one pharmaceutically acceptable excipient to form a mixture; and c) forming a tablet by compressing the mixture obtained from step iii).

In some embodiments, the composition further comprises a dry binder. In some embodiments, water is added to the composition comprising the dry binder. In some embodiments, combining niraparib, a diluent selected from mannitol and calcium phosphate dibasic, microcrystalline cellulose, and magnesium stearate to form a composition comprising niraparib, the diluent selected from mannitol and calcium phosphate dibasic, microcrystalline cellulose, and magnesium stearate from step i) further comprises blending the niraparib, a diluent selected from mannitol and calcium phosphate dibasic, microcrystalline cellulose, and magnesium stearate. In some embodiments, dry granulating from step ii) comprises slugging and milling. In some embodiments, the ribbon thickness is from about 0.1 mm to about 2 mm.

In some embodiments, the composition from step i) further comprises a glidant (e.g., silicon dioxide). In some embodiments, the at least one pharmaceutically acceptable excipient for combining the granules with at least one pharmaceutically acceptable excipient to form a mixture from step iii) is a glidant (e.g., silicon dioxide). In some embodiments, the at least one pharmaceutically acceptable excipient for combining the granules with at least one pharmaceutically acceptable excipient to form a mixture from step iii) is a lubricant (e.g., magnesium stearate). In some embodiments, combining the granules with at least one pharmaceutically acceptable excipient to form a mixture from step iii) comprises blending the granules with at least one pharmaceutically acceptable excipient. In some embodiments, the composition from step i) is a blend composition.

In some embodiments, the composition from step i) further comprises silicon dioxide. In some embodiments, the at least one pharmaceutically acceptable excipient for combining the granules with at least one pharmaceutically acceptable excipient to form a mixture from step iii) is silicon dioxide. In some embodiments, the at least one pharmaceutically acceptable excipient for combining the granules with at least one pharmaceutically acceptable excipient to form a mixture from step iii) is magnesium stearate. In some embodiments, combining the granules with at least one pharmaceutically acceptable excipient to form a mixture from step iii) comprises blending the granules with at least one pharmaceutically acceptable excipient. In some embodiments, the composition from step i) is a blend composition.

In some embodiments, the amount of components used to form the intragranular phase is about 50% to about 98% by weight of the tablet composition. In some embodiments, the amount of components used to form the intragranular phase is about 85% to about 98% by weight of the tablet composition. In some embodiments, the amount of components used to form the intragranular phase is about 90% to about 98% by weight of the tablet composition. In some embodiments, the amount of components used to form the intragranular phase is about 92.5% to about 97.5% by weight of the tablet composition. In some embodiments, the amount of components used to form the intragranular phase is about 95% by weight of the tablet composition.

In some embodiments, the amount of components used to form the extragranular phase is about 2% to about 50% by weight of the tablet composition. In some embodiments, the amount of components used to form the extragranular phase is about 2% to about 15% by weight of the tablet composition. In some embodiments, the amount of components used to form the extragranular phase is about 2% to about 10% by weight of the tablet composition. In some embodiments, the amount of components used to form the extragranular phase is about 2.5% to about 7.5% by weight of the tablet composition. In some embodiments, the amount of components used to form the extragranular phase is about 5% by weight of the tablet composition.

In some embodiments, the granules have a bulk density of about 0.10 to about 0.99 g/cm$^3$. In some embodiments, the granules have a bulk density of about 0.10 to about 0.90 g/cm$^3$. In some embodiments, the granules have a bulk density of about 0.10 to about 0.80 g/cm$^3$. In some embodiments, the granules have a bulk density of about 0.10 to about 0.70 g/cm$^3$. In some embodiments, the granules have a bulk density of about 0.10 to about 0.60 g/cm$^3$. In some embodiments, the granules have a bulk density of about 0.10 to about 0.50 g/cm$^3$. In some embodiments, the granules have a bulk density of about 0.10 to about 0.40 g/cm$^3$. In some embodiments, the granules have a bulk density of about 0.10 to about 0.30 g/cm$^3$. In some embodiments, the granules have a bulk density of about 0.10 to about 0.20 g/cm$^3$. In some embodiments, the granules have a bulk density of about 0.20 to about 0.99 g/cm$^3$. In some embodiments, the granules have a bulk density of about 0.20 to about 0.90 g/cm$^3$. In some embodiments, the granules have a bulk density of about 0.20 to about 0.80 g/cm$^3$. In some embodiments, the granules have a bulk density of about 0.20 to about 0.70 g/cm$^3$. In some embodiments, the granules have a bulk density of about 0.20 to about 0.60 g/cm$^3$. In some embodiments, the granules have a bulk density of about 0.20 to about 0.50 g/cm$^3$. In some embodiments, the granules have a bulk density of about 0.20 to about 0.40 g/cm$^3$. In some embodiments, the granules have a bulk density of about 0.20 to about 0.30 g/cm$^3$.

In some embodiments, the granules have a bulk density of about 0.10, about 0.11, about 0.12, about 0.13, about 0.14, about 0.15, about 0.16, about 0.17, about 0.18, about 0.19, about 0.20, about 0.21, about 0.22, about 0.23, about 0.24, about 0.25, about 0.26, about 0.27, about 0.28, about 0.29, about 0.30, about 0.31, about 0.32, about 0.33, about 0.34, about 0.35, about 0.36, about 0.37, about 0.38, about 0.39, about 0.40, about 0.41, about 0.42, about 0.43, about 0.44, about 0.45, about 0.46, about 0.47, about 0.48, about 0.49, about 0.50, about 0.51, about 0.52, about 0.53, about 0.54, about 0.55, about 0.56, about 0.57, about 0.58, about 0.59, about 0.60, about 0.61, about 0.62, about 0.63, about 0.64, about 0.65, about 0.66, about 0.67, about 0.68, about 0.69, about 0.70, about 0.71, about 0.72, about 0.73, about 0.74, about 0.75, about 0.76, about 0.77, about 0.78, about 0.79, about 0.80, about 0.81, about 0.82, about 0.83, about 0.84, about 0.85, about 0.86, about 0.87, about 0.88, about 0.89, about 0.90, about 0.91, about 0.92, about 0.93, about 0.94, about 0.95, about 0.96, about 0.97, about 0.98, or about 0.99 g/cm$^3$.

In some embodiments, the granules have a tapped density of about 0.10 to about 0.99 g/cm$^3$. In some embodiments, the granules have a tapped density of about 0.10 to about 0.90 g/cm$^3$. In some embodiments, the granules have a tapped density of about 0.10 to about 0.80 g/cm$^3$. In some embodiments, the granules have a tapped density of about 0.10 to about 0.70 g/cm$^3$. In some embodiments, the granules have a tapped density of about 0.10 to about 0.60 g/cm$^3$. In some embodiments, the granules have a tapped density of about 0.10 to about 0.50 g/cm$^3$. In some embodiments, the granules have a tapped density of about 0.10 to about 0.40 g/cm$^3$. In some embodiments, the granules have a tapped density of about 0.10 to about 0.30 g/cm$^3$. In some embodiments, the granules have a tapped density of about 0.10 to about 0.20 g/cm$^3$. In some embodiments, the granules have a tapped density of about 0.20 to about 0.99 g/cm$^3$. In some embodiments, the granules have a tapped density of about 0.20 to about 0.90 g/cm$^3$. In some embodiments, the granules have a tapped density of about 0.20 to about 0.80 g/cm$^3$. In some embodiments, the granules have a tapped density of about 0.20 to about 0.70 g/cm$^3$. In some embodiments, the granules have a tapped density of about 0.20 to about 0.60 g/cm$^3$.

In some embodiments, the granules have a tapped density of about 0.20 to about 0.50 g/cm$^3$. In some embodiments, the granules have a tapped density of about 0.20 to about 0.40 g/cm$^3$. In some embodiments, the granules have a tapped density of about 0.20 to about 0.30 g/cm$^3$. In some embodiments, the granules have a tapped density of about 0.30 to about 0.99 g/cm$^3$. In some embodiments, the granules have a tapped density of about 0.30 to about 0.90 g/cm$^3$. In some embodiments, the granules have a tapped density of about 0.30 to about 0.80 g/cm$^3$. In some embodiments, the granules have a tapped density of about 0.30 to about 0.70 g/cm$^3$. In some embodiments, the granules have a tapped density of about 0.30 to about 0.60 g/cm$^3$. In some embodiments, the granules have a tapped density of about 0.30 to about 0.50 g/cm$^3$. In some embodiments, the granules have a tapped density of about 0.30 to about 0.40 g/cm$^3$.

In some embodiments, the granules have a tapped density of about 0.10, about 0.11, about 0.12, about 0.13, about 0.14, about 0.15, about 0.16, about 0.17, about 0.18, about 0.19, about 0.20, about 0.21, about 0.22, about 0.23, about 0.24, about 0.25, about 0.26, about 0.27, about 0.28, about 0.29, about 0.30, about 0.31, about 0.32, about 0.33, about 0.34, about 0.35, about 0.36, about 0.37, about 0.38, about 0.39, about 0.40, about 0.41, about 0.42, about 0.43, about 0.44, about 0.45, about 0.46, about 0.47, about 0.48, about 0.49, about 0.50, about 0.51, about 0.52, about 0.53, about 0.54, about 0.55, about 0.56, about 0.57, about 0.58, about 0.59, about 0.60, about 0.61, about 0.62, about 0.63, about 0.64, about 0.65, about 0.66, about 0.67, about 0.68, about 0.69, about 0.70, about 0.71, about 0.72, about 0.73, about 0.74, about 0.75, about 0.76, about 0.77, about 0.78, about 0.79, about 0.80, about 0.81, about 0.82, about 0.83, about 0.84, about 0.85, about 0.86, about 0.87, about 0.88, about 0.89, about 0.90, about 0.91, about 0.92, about 0.93, about 0.94, about 0.95, about 0.96, about 0.97, about 0.98, or about 0.99 g/cm$^3$.

Intragranular Phase/Extragranular Phase Distribution

In another aspect, provided herein is method of preparing formulations with specific distributions of intragranular phase and extragranular phase components. Provided in one aspect is a method of making a composition comprising a tablet comprising niraparib comprising: a) forming an intragranular phase comprising i) combining niraparib and at least one pharmaceutically acceptable excipient to form a composition comprising niraparib and at least one pharmaceutically acceptable excipient; and ii) granulating the composition comprising niraparib and at least one pharmaceutically acceptable excipient to form granules; b) forming an extragranular phase comprising iii) combining the granules with at least one pharmaceutically acceptable excipient to form a mixture; and c) forming a tablet by compressing the mixture obtained from step iii); wherein the tablet has at least one of the following: (1) the amount of components used to form the intragranular phase is about 50% to about 98% by weight of the tablet composition; and (2) the amount of components used to form the extragranular phase is about 2% to about 50% by weight of the tablet composition.

In some embodiments, the amount of components used to form the intragranular phase is about 50% to about 98% by weight of the tablet composition. In some embodiments, the amount of components used to form the intragranular phase is about 85% to about 98% by weight of the tablet composition. In some embodiments, the amount of components used to form the intragranular phase is about 90% to about 98% by weight of the tablet composition. In some embodiments, the amount of components used to form the intragranular phase is about 92.5% to about 97.5% by weight of the tablet composition. In some embodiments, the amount of components used to form the intragranular phase is about 95% by weight of the tablet composition. In some embodiments, the amount of components used to form the extragranular phase is about 2% to about 50% by weight of the tablet composition. In some embodiments, the amount of components used to form the extragranular phase is about 2% to about 15% by weight of the tablet composition. In some embodiments, the amount of components used to form the extragranular phase is about 2% to about 10% by weight of the tablet composition. In some embodiments, the amount of components used to form the extragranular phase is about 2.5% to about 7.5% by weight of the tablet composition. In some embodiments, the amount of components used to form the extragranular phase is about 5% by weight of the tablet composition.

In some embodiments, the at least one pharmaceutically acceptable excipient from step i) is a second diluent (e.g., microcrystalline cellulose, starch, polyethylene oxide, and hydroxylpropyl methylcellulose (HPMC). In some embodiments, the at least one pharmaceutically acceptable excipient from step i) is a first diluent (e.g., lactose monohydrate, lactose anhydrous, mannitol, and calcium phosphate dibasic). In some embodiments, the at least one pharmaceutically acceptable excipient from step i) is a lubricant (e.g., magnesium stearate). In some embodiments, the at least one pharmaceutically acceptable excipient is a glidant (e.g., silicon dioxide).

In some embodiments, the at least one pharmaceutically acceptable excipient from step i) is microcrystalline cellulose. In some embodiments, the at least one pharmaceutically acceptable excipient from step i) is lactose monohydrate, lactose anhydrous, mannitol, or calcium phosphate dibasic. In some embodiments, the at least one pharmaceutically acceptable excipient from step i) is magnesium stearate. In some embodiments, the at least one pharmaceutically acceptable excipient from step i) is silicon dioxide In some embodiments, the granulating from step ii) is wet granulating. In some embodiments, the wet granulating further comprises adding a binder. In some embodiments, the binder is a liquid binder. In some embodiments, the liquid binder is dissolved povidone. In some embodiments, the liquid binder is dissolved starch, dissolved hydroxypropyl cellulose (HPC), dissolved hydroxypropyl methylcellulose (HPMC), or liquid polyethylene glycol (PEG). In some embodiments, the liquid binder is a melted binder. In some embodiments, the melted binder is a hydrophilic polyethylene glycol (PEG), poloxamer, hydrophobic fatty acid, fatty alcohol, wax, hydrogenated vegetable oil, or glyceride. In some embodiments, the binder is a dry binder. In some embodiments, the dry binder is hydroxypropyl cellulose (HPC). In some embodiments, the dry binder is hydroxypropyl methylcellulose (HPMC). In some embodiments, the dry binder is povidone (PVP) or starch. In some embodiments, the wet-granulating from step ii) further comprises wet-sieving. In some embodiments, the wet granulating from step ii) further comprises drying and dry sieving. In some embodiments, wherein drying comprises the addition of a glidant. In some embodiments, the glidant is silicon dioxide.

In some embodiments, the granulating from step ii) is dry-granulating. In some embodiments, dry-granulating comprises slugging and milling.

In some embodiments, the at least one pharmaceutically acceptable excipient for combining the granules with at least one pharmaceutically acceptable excipient to form a mixture from step iii) is silicon dioxide. In some embodiments, the at least one pharmaceutically acceptable excipient for combining the granules with at least one pharmaceutically acceptable excipient to form a mixture from step iii) is magnesium stearate.

Dosage Form Coating

The term "coating" means a process by which an outer layer of coating material is applied to the surface of a dosage form in order to confer specific benefits over uncoated variety. It involves application of a coat, including sugar or polymeric coats, on the dosage form. The advantages of tablet coating are taste masking, odor masking, physical and chemical protection, enhancing safety of dosage form handling, protection of the drug in chemically challenging environments (e.g. stomach), and to control its release profile. The coating may provide moisture protection, enhanced appearance, increased mechanical integrity, improved swallowability, improved taste, and/or masking of odors. Coating may be applied to a wide range of oral solid dosage form, such as particles, powders, granules, crystals, pellets and tablets. When coating composition is applied to a batch of tablets in a coating pan, the tablet surfaces become covered with a polymeric film. In some embodiments, a solid dosage form may comprise a coating systems of polyvinyl alcohol (PVA) with polyethylene glycol (PEG/Macrogol) as a plasticizer. In some embodiments, coating systems may comprise: i) PVA, ii) HPMC with glycerol triacetate (triacetin) as a plasticizer, iii) ethylcellulose with a plasticizer agent, iv) Eudragit with a plasticizer agent and v) acrylates. Commercial coating systems are also available in the art and may be used with any of the solid dosage forms disclosed herein.

Dose-to-Dose Uniformity

In some embodiments, the composition has a dose-to-dose niraparib concentration variation of less than 50%. In some embodiments, the composition has a dose-to-dose niraparib concentration variation of less than 40%. In some embodiments, the composition has a dose-to-dose niraparib concentration variation of less than 30%. In some embodiments, the composition has a dose-to-dose niraparib concentration variation of less than 20%. In some embodiments, the composition has a dose-to-dose niraparib concentration variation of less than 10%. In some embodiments, the composition has a dose-to-dose niraparib concentration variation of less than 5%. Specific standards for dosage uniformity may be found at: 1) Ph. Eur. 2.9.40. Uniformity of Dosage Units, 2) JP 6.02 Uniformity of Dosage Units, and 3) USP General Chapter Uniformity of Dosage Units each of which is incorporated by reference herein.

In some embodiments, the dose-to-dose niraparib concentration variation is based on 10 consecutive doses. In some embodiments, the dose-to-dose niraparib concentration variation is based on 8 consecutive doses. In some embodiments, the dose-to-dose niraparib concentration variation is based on 5 consecutive doses. In some embodiments, the dose-to-dose niraparib concentration variation is based on 3 consecutive doses. In some embodiments, the dose-to-dose niraparib concentration variation is based on 2 consecutive doses.

Kits/Articles of Manufacture

If desired, the niraparib may be provided in a kit. The kits include a therapeutically effective dose of niraparib for treating diseases and conditions, such as cancer. The dosage forms may be packaged on blister cards for daily administration convenience and to improve adherence.

The disclosure also provides kits for preventing, treating or ameliorating the symptoms of a disease or disorder in a mammal. Such kits generally will comprise one or more of niraparib compositions or devices disclosed herein, and instructions for using the kit. The disclosure also contemplates the use of one or more of niraparib compositions, in the manufacture of medicaments for treating, abating, reducing, or ameliorating the symptoms of a disease, dysfunction, or disorder in a mammal, such as a human that has, is suspected of having, or at risk for developing cancer.

In some embodiments, a kit includes one or more additional containers, each with one or more of various materials (such as reagents, optionally in concentrated form, and/or devices) desirable from a commercial and user standpoint for use of a formulation described herein. Non-limiting examples of such materials include, but not limited to, buffers, diluents, filters, needles, syringes; carrier, package, container, vial and/or tube labels listing contents and/or instructions for use and package inserts with instructions for use. A set of instructions is optionally included. In a further embodiment, a label is on or associated with the container. In yet a further embodiment, a label is on a container when letters, numbers or other characters forming the label are attached, molded or etched into the container itself; a label is associated with a container when it is present within a receptacle or carrier that also holds the container, e.g., as a package insert. In other embodiments a label is used to indicate that the contents are to be used for a specific therapeutic application. In yet another embodiment, a label also indicates directions for use of the contents, such as in the methods described herein.

In certain embodiments, the pharmaceutical compositions are presented in a pack or dispenser device which contains one or more unit dosage forms containing a compound provided herein. In another embodiment, the pack for example contains metal or plastic foil, such as a blister pack. In a further embodiment, the pack or dispenser device is accompanied by instructions for administration. In yet a further embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. In another embodiment, such notice, for example, is the labeling approved by the U.S. Food and Drug Administration for prescription drugs, or the approved product insert. In yet another embodiment, compositions containing a compound provided herein formulated in a compatible pharmaceutical carrier are also prepared, placed in an appropriate container, and labeled for treatment of an indicated condition.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed with invention as defined in the claims which follow. The invention disclosed herein is further illustrated by the following examples which in no way should be construed as being limiting.

Example 1—Tablet Formulations Prepared from Wet Granulation

The following formulations shown in Tables 13-14 were prepared through wet granulation as shown in FIG. 1.

TABLE 13

| Formulation 1 (300 mg Niraparib) | | |
|---|---|---|
| Component | Amount (mg) | % |
| Intragranular Phase | | |
| Niraparib Tosylate Monohydrate | 478.0 | 47.8 |
| Lactose Monohydrate | 203.5 | 20.4 |
| Microcrystalline Cellulose | 203.5 | 20.4 |
| Crospovidone | 40.0 | 4.0 |
| Povidone | 20.0 | 2.0 |
| Purified water | | N/A |
| Total (intragranular phase) | 945.0 | 94.5 |
| Extragranular Phase | | |
| Crospovidone | 40.0 | 4.0 |
| Silicon Dioxide | 5.0 | 0.5 |
| Magnesium Stearate | 10.00 | 1.0 |
| Total (extragranular phase) | 55.0 | 5.5 |

TABLE 14

| Formulation 2 (300 mg Niraparib) | | |
|---|---|---|
| Component | Amount (mg) | % |
| Intragranular Phase | | |
| Niraparib Tosylate Monohydrate | 478.0 | 47.8 |
| Lactose Monohydrate | 193.5 | 19.4 |
| Microcrystalline Cellulose | 193.50 | 19.4 |
| Croscarmellose | 40.0 | 4.0 |
| Hydroxypropyl cellulose | 40.0 | 4.0 |
| Purified water | | N/A |
| Total (intragranular phase) | 945.0 | 94.5 |
| Extragranular Phase | | |
| Croscarmellose Sodium | 40.0 | 4.0 |
| Silicon Dioxide | 5.00 | 0.5 |
| Magnesium Stearate | 10.00 | 1.0 |
| Total (extragranular phase) | 55.00 | 5.5 |

Figure 2:
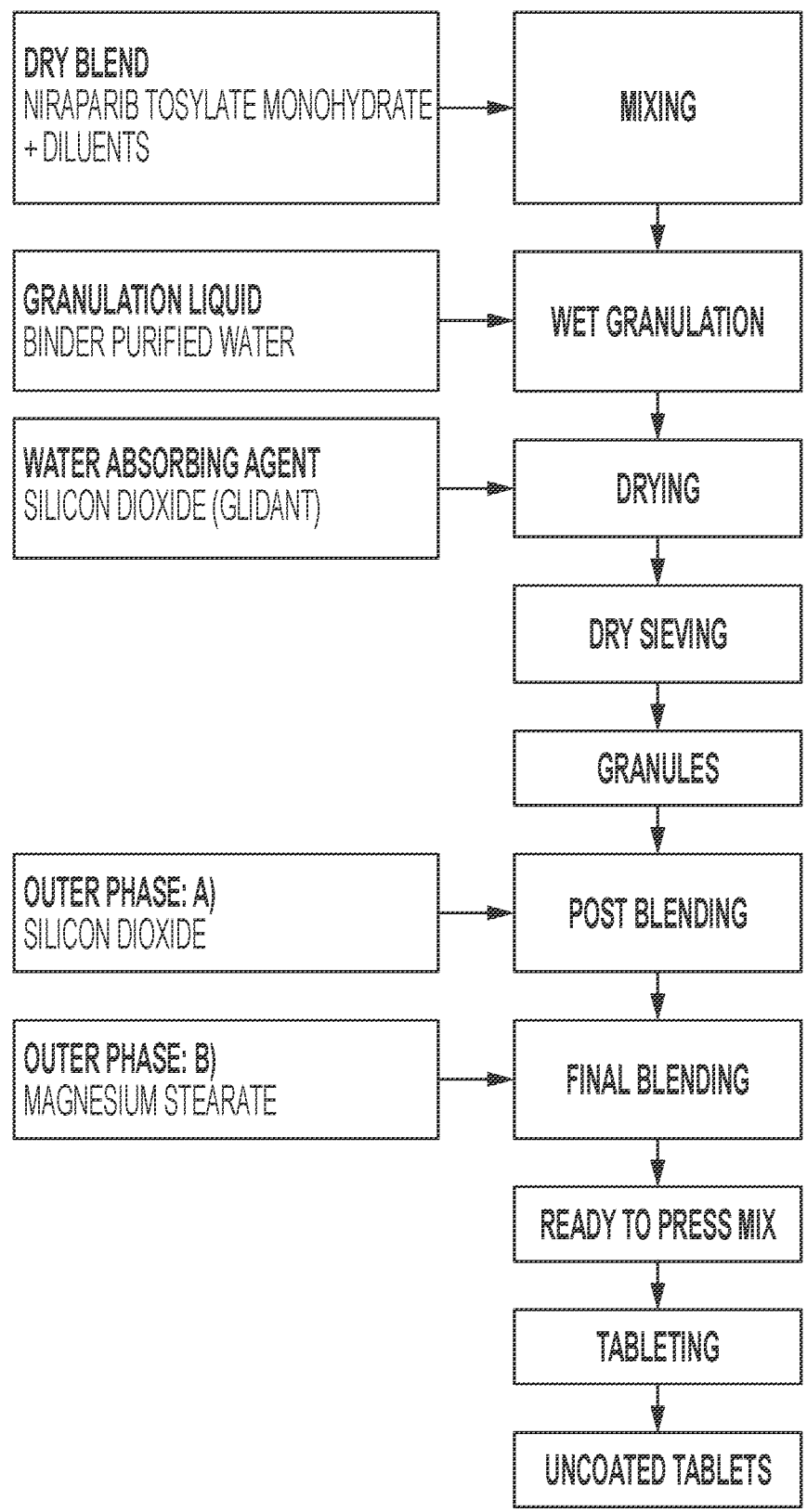
FIG. 2 is schematic of an exemplary moisture-activated dry granulation (MADG) manufacturing process of the niraparib tablet.

Example 2—Tablet Formulations Prepared from Moisture-Activated Dry Granulation The following formulations shown in Table 15 were prepared through moisture-activated dry granulation as shown in FIG. 2.

TABLE 15

| Formulation 3 (300 mg Niraparib) | | |
|---|---|---|
| Component | Amount (mg) | % |
| Intragranular Phase | | |
| Niraparib Tosylate Monohydrate | 478.0 | 47.8 |
| Lactose Monohydrate | 178.5 | 17.9 |
| Microcrystalline Cellulose | 178.5 | 17.9 |
| Crospovidone | 40.0 | 4.0 |
| Povidone | 40.0 | 4.0 |
| Purified water | | N/A |
| Silicon Dioxide | 25.0 | 2.5 |
| Total (intragranular phase) | 940.0 | 94.0 |
| Extragranular Phase | | |
| Crospovidone | 40.0 | 4.0 |
| Silicon Dioxide | 10.0 | 1.0 |
| Magnesium Stearate | 10.00 | 1.0 |
| Total (extragranular phase) | 60.00 | 6.00 |

Example 3—Tablet Formulations Prepared from Dry Granulation

Figure 3:
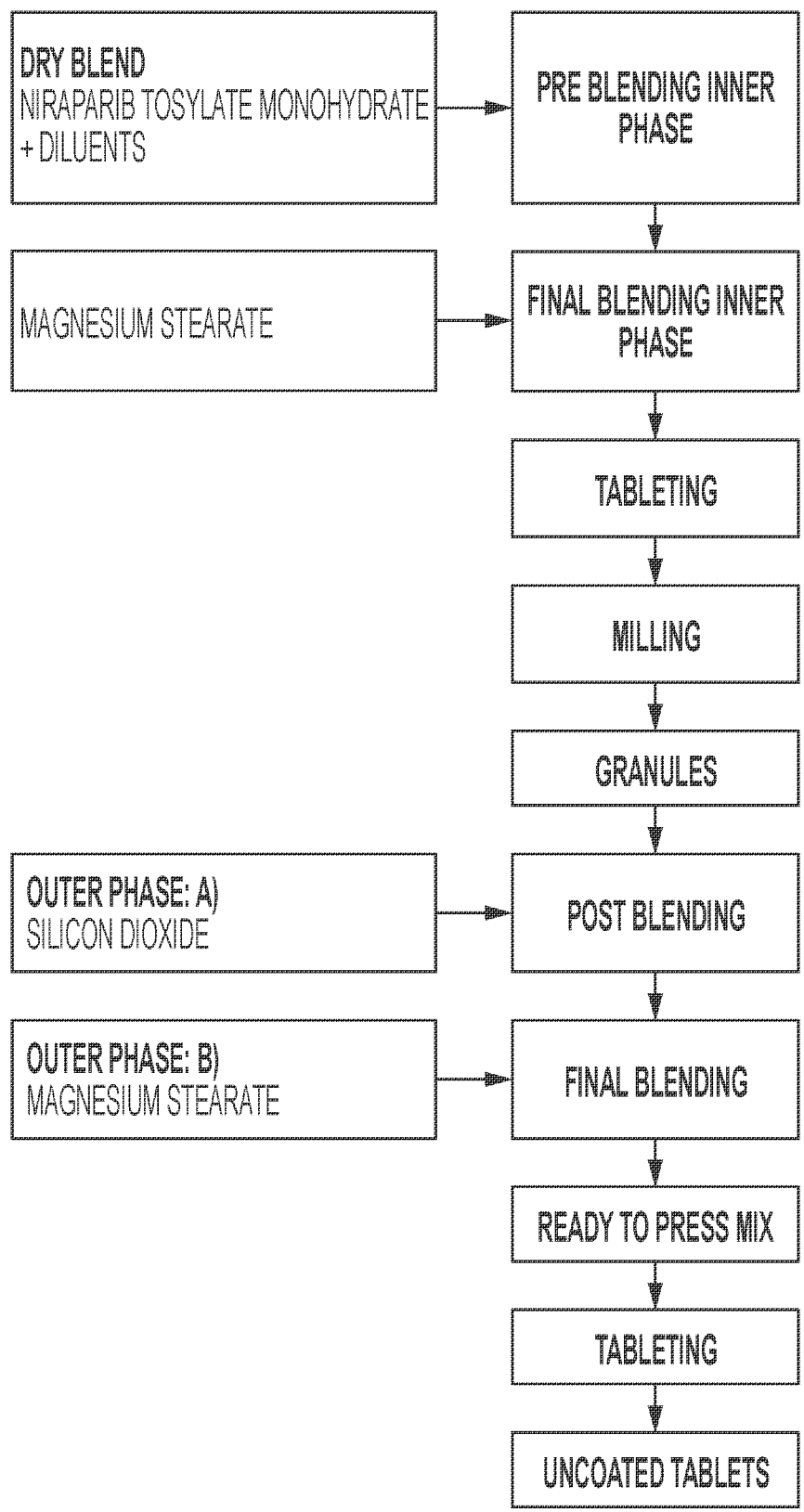
FIG. 3 is schematic of an exemplary dry granulation manufacturing process of the niraparib tablet.

The following formulations shown in Tables 16-18 were prepared through dry granulation as shown in FIG. 3.

TABLE 16

| Formulation 4 (300 mg Niraparib) | | |
|---|---|---|
| Component | Amount (mg) | % |
| Intragranular Phase | | |
| Niraparib Tosylate Monohydrate | 478.0 | 47.8 |
| Microcrystalline Cellulose | 201.0 | 20.1 |
| Calcium phosphate dibasic | 201.0 | 20.1 |
| Crospovidone | 40.0 | 4.0 |
| Povidone | 20.0 | 2.0 |
| Magnesium Stearate | 5.0 | 0.5 |
| Total (intragranular phase) | 945.0 | 94.5 |

TABLE 16-continued

Formulation 4 (300 mg Niraparib)

| Component | Amount (mg) | % |
|---|---|---|
| Extragranular Phase | | |
| Crospovidone | 40.0 | 4.0 |
| Silicon Dioxide | 5.0 | 0.5 |
| Magnesium Stearate | 10.00 | 1.0 |
| Total (extragranular phase) | 55.0 | 5.5 |

TABLE 17

Formulation 5 (300 mg Niraparib)

| Component | Amount (mg) | % |
|---|---|---|
| Intragranular Phase | | |
| Niraparib Tosylate Monohydrate | 478.0 | 47.8 |
| Microcrystalline Cellulose | 201.0 | 20.1 |
| Mannitol | 201.0 | 20.1 |
| Croscarmellose Sodium | 40.0 | 4.0 |
| Hydroxypropyl cellulose | 20.0 | 2.0 |
| Magnesium Stearate | 5.0 | 0.5 |
| Total (intragranular phase) | 945.0 | 94.5 |
| Extragranular Phase | | |
| Croscarmellose Sodium | 40.0 | 4.0 |
| Silicon Dioxide | 5.0 | 0.5 |
| Magnesium Stearate | 10.00 | 1.0 |
| Total (extragranular phase) | 55.0 | 5.5 |

TABLE 18

Formulation 6 (300 mg Niraparib)

| Component | Amount (mg) | % |
|---|---|---|
| Intragranular Phase | | |
| Niraparib Tosylate Monohydrate | 478.0 | 47.8 |
| Microcrystalline Cellulose | 201.0 | 20.1 |
| Mannitol | 201.0 | 20.1 |
| Crospovidone | 40.0 | 4.0 |
| Povidone | 20.0 | 2.0 |
| Magnesium Stearate | 5.0 | 0.5 |
| Total (intragranular phase) | 945.0 | 94.5 |
| Extragranular Phase | | |
| Crospovidone | 40.0 | 4.0 |
| Silicon Dioxide | 5.0 | 0.5 |
| Magnesium Stearate | 10.00 | 1.0 |
| Total (extragranular phase) | 55.0 | 5.5 |

Example 4—Clinical Studies

The safety and efficacy of niraparib as maintenance therapy was studied in a Phase 3 randomized, double-blind, placebo-controlled trial (NOVA) in patients with platinum-sensitive recurrent epithelial ovarian, fallopian tube, or primary peritoneal cancer. All patients had received at least two prior platinum-containing regimens and were in response (complete or partial) to their most recent platinum-based regimen.

Eligible patients were assigned to one of two cohorts based on the results of a germline BRCA mutation test. Women who were hereditary germline BRCA mutation carriers were assigned to the germline BRCA mutated (gBRCAmut) cohort (n=203) and women who did not carry a hereditary germline BRCA mutation were assigned to the non-gBRCAmut cohort (n=350). Within each cohort, patients were randomized using a 2:1 allocation of niraparib to placebo. Randomization occurred within 8 weeks of the last dose of the most recent platinum-containing regimen.

Randomization within each cohort was stratified by time to progression after the penultimate platinum therapy (6 to <12 months and >12 months); use of bevacizumab in conjunction with the penultimate or last platinum regimen (yes/no); and best response during the most recent platinum regimen (complete response and partial response).

Patients began treatment on Cycle 1/Day 1 with niraparib 300 mg or matched placebo administered QD in continuous 28-day cycles. Clinic visits occurred each cycle (4 weeks±3 days). Patients randomized to placebo were not allowed to cross over to niraparib treatment at any time.

The primary endpoint, PFS (progression-free survival), was determined by central independent assessment per RECIST (Response Evaluation Criteria in Solid Tumors, version 1.1) or clinical signs and symptoms and increased CA-125. PFS as defined in the NOVA study was measured from the time of randomization (which occurred up to 2 months after completion of the most recent chemotherapy regimen) to disease progression or death.

Prior to unblinding of the study, tumors of patients randomized to the non-gBRCAmut cohort were tested for the presence of homologous recombination deficiency (HRD) using the Myriad myChoice® HRD test, which evaluates three independent biomarkers of tumor genome instability: loss of heterozygosity, telomeric allelic imbalance, and large-scale state transitions. Tumors with homologous recombination deficiencies and those with somatic BRCA mutations were defined as HRD positive (HRDpos).

The primary efficacy analysis for PFS was prospectively defined and assessed for the gBRCAmut cohort. The primary efficacy analysis for PFS was prospectively defined and assessed for the non-gBRCAmut cohort with a hierarchical testing schema. In the first step, PFS was assessed in the group of patients with HRDpos tumors and if significant, PFS was assessed in the overall non-gBRCAmut cohort.

Secondary efficacy endpoints included chemotherapy-free interval (CFI), time to first subsequent therapy (TFST), PFS after the first subsequent therapy (PFS2), time to second subsequent therapy (TSST) and OS (overall survival).

Table 19 shows the results for the PFS primary endpoint for each of the primary efficacy populations (gBRCAmut cohort, the overall non-gBRCAmut cohort and the HRDpos group in the non-gBRCAmut cohort).

PFS was significantly longer for patients who received niraparib compared to those who received placebo for all three primary efficacy populations.

Within the gBRCAmut cohort, the median PFS from time of randomization was 21.0 months with niraparib versus 5.5 months with placebo.

In the overall non-gBRCAmut cohort, the median PFS from time of randomization was 9.3 months with niraparib versus 3.9 months with placebo.

PFS was also significantly longer with niraparib than with placebo in the HRDpos group of the non-gBRCAmut cohort: 12.9 months versus 3.8 months.

TABLE 19

PFS Primary Endpoints

|  | gBRCAmut Cohort | | non-gBRCAmut Cohort | | HRDpos* | |
| --- | --- | --- | --- | --- | --- | --- |
|  | Niraparib (N = 138) | Placebo (N = 65) | Niraparib (N = 234) | Placebo (N = 116) | Niraparib (N = 106) | Placebo (N = 56) |
| PFS Median | 21.0 | 5.5 | 9.3 | 3.9 | 12.9 | 3.8 |
| (95% CI)† | (12.9, NR) | (3.8, 7.2) | (7.2, 11.2) | (3.7, 5.5) | (8.1, 15.9) | (3.5, 5.7) |
| p-value | <0.0001 | | <0.0001 | | <0.0001 | |
| Hazard Ratio (HR) | 0.27 | | 0.45 | | 0.38 | |
| (95% CI) | (0.173, 0.410) | | (0.338, 0.607) | | (0.243, 0.586) | |

*HRDpos represents a prospectively defined subgroup of the non-gBRCAmut cohort.
†Progression-free survival is defined as the time in months from the date of randomization to disease progression or death.

Figure 4:
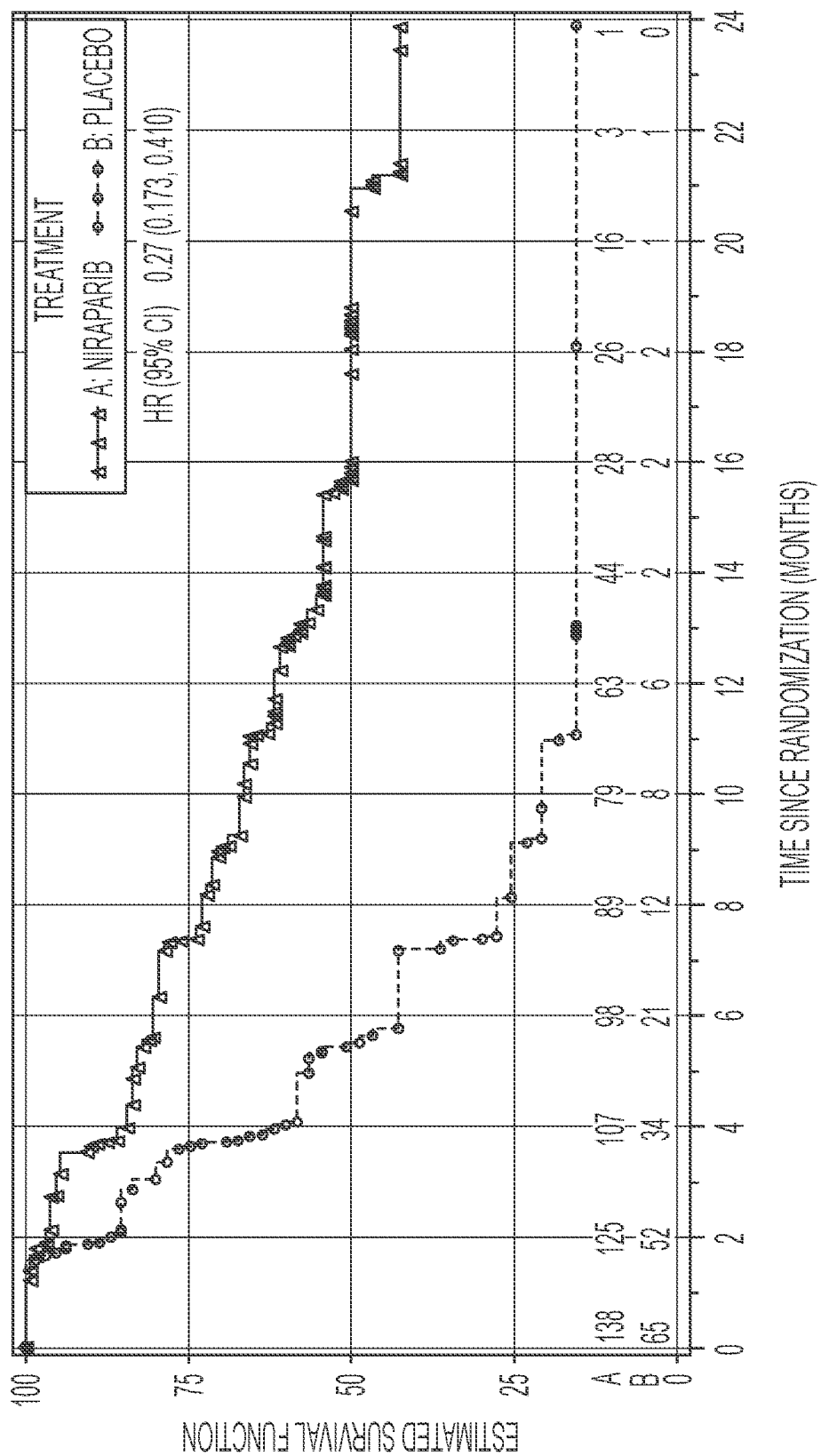
FIG. 4 is an exemplary Kaplan-Meier plot for progression-free survival in the gBRCAmut cohort based on IRC assessment (ITT Population, N=203).

The Kaplan-Meier curves for the 2 treatment arms in the gBRCAmut cohort show early divergence of the curves with the niraparib curve consistently above that of placebo and sustained separation in the curves throughout the observation period (FIG. 4).

Figure 5:
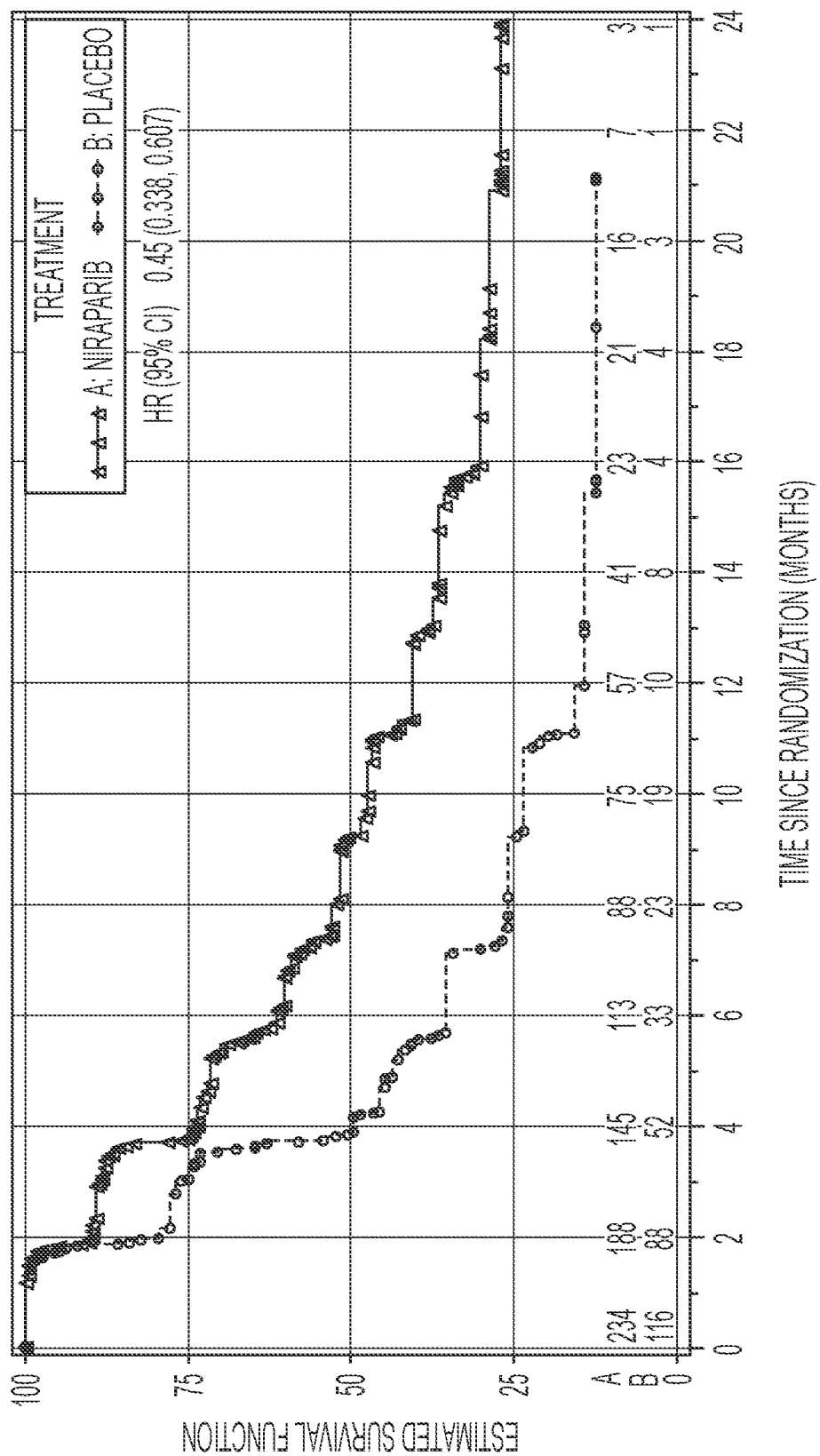
FIG. 5 is an exemplary Kaplan-Meier for progression-free survival in the Non-gBRCAmut cohort overall based on IRC assessment (ITT Population, N=350).

The Kaplan-Meier curves for the 2 treatment arms in the overall non-gBRCAmut cohort show early divergence of the curves with the niraparib curve consistently above that of placebo and sustained separation in the curves throughout the observation period (FIG. 5).

The secondary endpoints CFI and TFST demonstrated a persistent treatment effect in favor of the niraparib treatment arm in the gBRCAmut cohort: Median CFI was 22.8 months (95% CI: 17.9, NE) in the niraparib arm compared to 9.4 months (95% CI: 7.9, 10.6) in the placebo arm with a HR of 0.26 (95% CI: 0.166, 0.409) (p<0.0001). Median TFST was 21.0 months (95% CI: 17.5, NE) in the niraparib arm compared to 8.4 months (95% CI: 6.6, 10.6) in the placebo arm with a HR of 0.31 (95% CI: 0.205, 0.481) (p<0.0001).

In the non-gBRCAmut cohort: Median CFI was 12.7 months (95% CI: 11.0, 14.7) in the niraparib arm compared to 8.6 months (95% CI: 6.9, 10.0) in the placebo arm with an HR of 0.50 (95% CI: 0.370, 0.666) (p<0.0001). Median TFST was 11.8 months (95% CI: 9.7, 13.1) in the niraparib arm compared to 7.2 months (95% CI: 5.7, 8.5) in the placebo arm with an HR of 0.55 (95% CI: 0.412, 0.721) (p<0.0001).

At the time of the analysis, the secondary endpoint results for PFS2, OS and TSST were not mature enough to evaluate. However, no detrimental effect was observed at the time of data cutoff for any of the endpoints.

Example 5—Tablet Stability Under Storage Conditions

The stability of the tablets disclosed herein, such as those disclosed in Examples 1-3, is evaluated under storage in HDPE bottles 'open dish' under accelerated conditions, such as at 40° C. and 75% relative humidity (RH). Stability may be evaluated, for example, for 1 3, 6, 9, 12, 24 or 36 months.

The tablets corresponding to Formulations 1-6 were evaluated for the amount of total impurities at 40° C. and 75% relative humidity (RH) after storage for 0, 1, and 2 months, and the total impurity measured for each of the tablets was less than 0.2%.

The tablets corresponding to Formulations 1-6 were also evaluated for water content at 40° C. and 75% relative humidity (RH) after storage for 0, 1, and 2 months, and the results are summarized in Table 20.

TABLE 20

Water Content (%)

| Tablet | Water Content at 0 months [%] | Water Content at 1 month (40° C./75 RH) [%] | Water Content at 2 months (40° C./75 RH) [%] |
| --- | --- | --- | --- |
| Formulation 1 | 5.0 | 7.2 | 6.0 |
| Formulation 2 | 4.3 | 6.4 | 5.7 |
| Formulation 3 | 7.7 | 7.6 | 7.0 |
| Formulation 4 | 4.3 | 6.4 | 6.0 |
| Formulation 5 | 3.4 | 5.1 | 4.1 |
| Formulation 6 | 4.2 | 6.0 | 4.9 |

Example 6—Clinical Study of Tablet Compositions

The study is a multicenter, open label study in patients with advanced solid tumors and is a 2-stage, randomized-sequence, single-crossover study to assess the relative bioavailability (BA) and bioequivalence (BE) of niraparib tablet formulation relative to the capsule formulation.

Niraparib will be provided as niraparib tosylate monohydrate, with the specified amounts relating to the equivalent amount of the niraparib free base.

The first phase of the study is a study of the pharmacokinetics (PK). In the PK phase, a patient can receive a single dose of the formulation (e.g., a single 300 mg tablet or three 100 mg capsules) followed by a 7-day (+1 day) Washout/PK period for stage 1 of the study and a 14-day (+/−4 day) Washout/PK period for stage 2 of the study, followed by a dose of the alternate formulation also in a fasted state, followed by a 7-day Washout/PK period. Patients receiving the tablet in the first treatment period will receive the capsules in the second treatment period and vice versa.

The PK parameters that will be estimated include area under the plasma concentration-time curve (AUC) from time 0 to the time of the last quantifiable concentration ($AUC_{0-t}$), area under the plasma concentration-time curve from time 0 extrapolated to infinity ($AUC_{0-\infty}$), apparent total body clearance (CL/F), $C_{max}$, $t_{max}$, termination elimination half-life ($t_{1/2}$), apparent terminal volume of distribution (Vz/F), and bioavailability/bioequivalence of the tablet formulation relative to the capsule formulation.

In embodiments, the 90% confidence interval of the ratio of geometric least-squares means of a PK parameter for a tablet composition is about 80-125% or about 90-110% of the same PK parameter for a capsule formulation to provide the equivalent administered dose of niraparib.

When patients complete the PK Phase of the study (at least 7 days from the beginning of PK period 2), they may be eligible to participate in the Extension Phase and continue to receive niraparib. A tumor assessment can be performed prior to the first dose of the Extension (pre-Extension Phase).

The starting dose of niraparib in the Extension Phase can be based on the patient's baseline actual body weight or platelet count. Patients with a baseline actual body weight of >77 kg and screening platelet count of >150,000/4, (obtained after completion of the PK phase, as part of Extension Phase screening) will take one 300 mg strength tablet or 3×100 mg capsules at each dose administration (QD). Patients with a baseline actual body weight of <77 kg and/or screening platelet count of <150,000/4, will take one 200 mg strength tablet or 2×100 mg capsules at each dose administration (QD). For patients whose initial starting dose is 200 mg QD, escalation to 300 mg QD is permitted after 2 cycles of therapy if no treatment interruption or discontinuation was required during the first 2 cycles of Extension Phase therapy. Should a patient start Extension Phase at 100 mg, consideration may be given to escalate to 200 mg after 2 cycles, therapy if no treatment interruption or discontinuation was required during the first 2 cycles of Extension Phase therapy and after approval from the Sponsor. A patient can remain on the same formulation (tablet versus capsule) throughout the extension phase.

Patients will return on the first day of every treatment cycle (28±7 days) to receive study drug and for safety assessments. Visits will continue approximately every 4 weeks until treatment discontinuation. In line with the niraparib US PI, dose interruption (no longer than 28 days) will be allowed based on adverse events (AEs). In addition, dose reductions to 200 mg QD and subsequently to 100 mg QD will be allowed based on AEs.

For example, Table 21 provides exemplary dose modifications based on non-hematologic toxicities.

TABLE 21

Niraparib Dose Reductions for Non-Hematologic Toxicities

| Event | Dose[1] |
|---|---|
| Initial dose | 300 mg QD |
| First dose reduction for treatment-related NCI-CTCAE v.4.03 Grade 3 or 4 AE or SAE where prophylaxis is not considered feasible | 200 mg QD |
| Second dose reduction for NCI-CTCAE v.4.03 Grade 3 or 4 AE or SAE where prophylaxis is not considered feasible | 100 mg QD |
| Continued treatment-related CTCAE Grade 3 or 4 AE or SAE ≥28 days | Discontinue study medication |

Abbreviations:
AE = adverse event;
CTCAE = Common Terminology Criteria for Adverse Events;
NCI-CTCAE = National Cancer Institute CTCAE;
SAE = serious adverse event;
QD = once daily
[1]Dose not to be decreased below 100 mg daily.

Example 7—Stability Data

Stability data for an exemplary niraparib formulation as provided in 100 and 300 mg tablets are summarized in Table 22 and FIGS. 6-9. As shown by these data, formulations described herein can feature desirable stability.

TABLE 22

Stability Data for Niraparib Tablets

| Lot Number and Dosage Strength | Storage Conditions | Storage Time (Months) | Corresponding FIG. |
|---|---|---|---|
| LOT A (100 mg) | 25° C./60% RH | T = 6 | FIG. 6 |
| | 40° C./75% RH | T = 6 | FIG. 7 |
| LOT B (300 mg) | 25° C./60% RH | T = 6 | FIG. 8 |
| | 40° C./75% RH | T = 6 | FIG. 9 |

What is claimed is:

1. A pharmaceutical composition in the form of a tablet comprising the following components on a weight percentage basis:
   (i) in an intragranular portion:
      (a) 40-50% of 2-{4-[(3S)-piperidin-3-yl]phenyl}-2H-indazole 7-carboxamide 4-methylbenzenesulfonate monohydrate;
      (b) 9-11% of a first diluent;
      (c) 30-40% of a second diluent;
      (d) 1-3% of a binder;
      (e) 0.1-2% of a disintegrant;
      (f) 2-4% of a glidant, adsorbent, or absorbent; and
      (g) 0.1-2% of a lubricant; and
   (ii) in an extragranular portion:
      (a) 0.1-2% of a disintegrant;
      (b) 0.1-2% of a glidant, adsorbent, or absorbent; and
      (c) 0.1-2% of a lubricant.

2. The pharmaceutical composition according to claim 1, wherein the first diluent is lactose monohydrate.

3. The pharmaceutical composition according to claim 1, wherein the second diluent is microcrystalline cellulose.

4. The pharmaceutical composition according to claim 1, wherein the binder is povidone.

5. The pharmaceutical composition according to claim 1, wherein the intragranular disintegrant is crospovidone.

6. The pharmaceutical composition according to claim 1, wherein the intragranular glidant, adsorbent, or absorbent is silicon dioxide.

7. The pharmaceutical composition according to claim 1, wherein the intragranular lubricant is magnesium stearate.

8. The pharmaceutical composition according to claim 1, wherein the extragranular phase disintegrant is crospovidone.

9. The pharmaceutical composition according to claim 1, wherein the extragranular glidant, adsorbent, or absorbent is silicon dioxide.

10. The pharmaceutical composition according to claim 1, wherein the extragranular lubricant is magnesium stearate.

11. The pharmaceutical composition according to claim 1, wherein:
(i) the first diluent of the intragranular portion is lactose monohydrate;
(ii) the second diluent of the intragranular portion is microcrystalline cellulose;
(iii) the binder of the intragranular portion is povidone;
(iv) the disintegrant of the intragranular portion is crospovidone;
(v) the glidant, adsorbent, or absorbent of the intragranular portion is silicon dioxide;
(vi) the lubricant of the intragranular portion is magnesium stearate;
(vii) the disintegrant of the extragranular portion is crospovidone;
(viii) the glidant, adsorbent, or absorbent of the extragranular portion is silicon dioxide; and
(ix) the lubricant of the extragranular portion is magnesium stearate.

12. The pharmaceutical composition according to claim 1, further comprising a film coating.

13. The pharmaceutical composition according to claim 1, wherein the amount of 2-{4-[(3S)-piperidin-3-yl]phenyl}-2H-indazole 7-carboxamide 4-methylbenzenesulfonate monohydrate in the tablet is about 100 mg based on niraparib free base.

14. The pharmaceutical composition according to claim 1, wherein the amount of 2-{4-[(3S)-piperidin-3-yl]phenyl}-2H-indazole 7-carboxamide 4-methylbenzenesulfonate monohydrate in the tablet is about 200 mg based on niraparib free base.

15. The pharmaceutical composition according to claim 1, wherein the amount of 2-{4-[(3S)-piperidin-3-yl]phenyl}-2H-indazole 7-carboxamide 4-methylbenzenesulfonate monohydrate in the tablet is about 300 mg based on niraparib free base.

* * * * *

UNITED STATES PATENT AND TRADEMARK OFFICE
CERTIFICATE OF CORRECTION

| | | |
|---|---|---|
| PATENT NO. | : 11,730,725 B2 | Page 1 of 1 |
| APPLICATION NO. | : 16/650948 | |
| DATED | : August 22, 2023 | |
| INVENTOR(S) | : McGurk et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 121 days.

Signed and Sealed this
Twelfth Day of November, 2024

Katherine Kelly Vidal
*Director of the United States Patent and Trademark Office*